US009861483B2

(12) United States Patent
Vogt

(10) Patent No.: US 9,861,483 B2
(45) Date of Patent: Jan. 9, 2018

(54) PLANAR BONE REPLACEMENT MATERIAL AND METHOD FOR PRODUCING A POROUS BODY

(71) Applicant: Heraeus Medical GmbH, Wehrheim (DE)

(72) Inventor: Sebastian Vogt, Erfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 1 day.

(21) Appl. No.: 15/144,192

(22) Filed: May 2, 2016

(65) Prior Publication Data

US 2016/0331540 A1 Nov. 17, 2016

(30) Foreign Application Priority Data

May 13, 2015 (DE) ........................ 10 2015 107 599

(51) Int. Cl.
*A61F 2/28* (2006.01)
*A61F 2/34* (2006.01)
*A61F 2/30* (2006.01)

(52) U.S. Cl.
CPC ................. *A61F 2/34* (2013.01); *A61F 2/28* (2013.01); *A61F 2002/305* (2013.01);
(Continued)

(58) Field of Classification Search
CPC ................. A61F 2/28; A61F 2/30; A61F 2/34
See application file for complete search history.

(56) References Cited

U.S. PATENT DOCUMENTS

| 2,717,437 A | 9/1955 | De Mestral |
| 3,408,705 A | 11/1968 | Kayser et al. |

(Continued)

FOREIGN PATENT DOCUMENTS

| CH | 295638 A | 1/1954 |
| DE | 1625396 A1 | 6/1970 |

(Continued)

OTHER PUBLICATIONS

Rueger, J.M.; "Bone Replacement Materials—Current Status and Future Outlook"; Der Orthopaede; 1998, pp. 72-83; Springer-Verlag; Germany.

(Continued)

*Primary Examiner* — Jason-Dennis Stewart
(74) *Attorney, Agent, or Firm* — Norris McLaughlin & Marcus P.A.

(57) ABSTRACT

Planar alloplastic bone replacement material and methods comprise at least one plate for augmentation of bone defects, whereby the bone replacement material consists of a biocompatible plastic material, a biocompatible metal and/or a biocompatible metal alloy, whereby the at least one plate comprises a planar structure and comprises a plurality of pins extending outwards from the planar structure of the at least one plate, whereby the pins each comprise at least one connecting element, whereby the pins are deformable elastically and are arranged sufficiently close to each other such that pressing the surfaces of multiple plates onto each other causes the connecting elements of different plates to interlock with and/or snap into each other and the mutually interlocked and/or snapped-in plates form an open-pored body of mutually interlocked and/or snapped-in plates.

29 Claims, 37 Drawing Sheets

Figure 1:
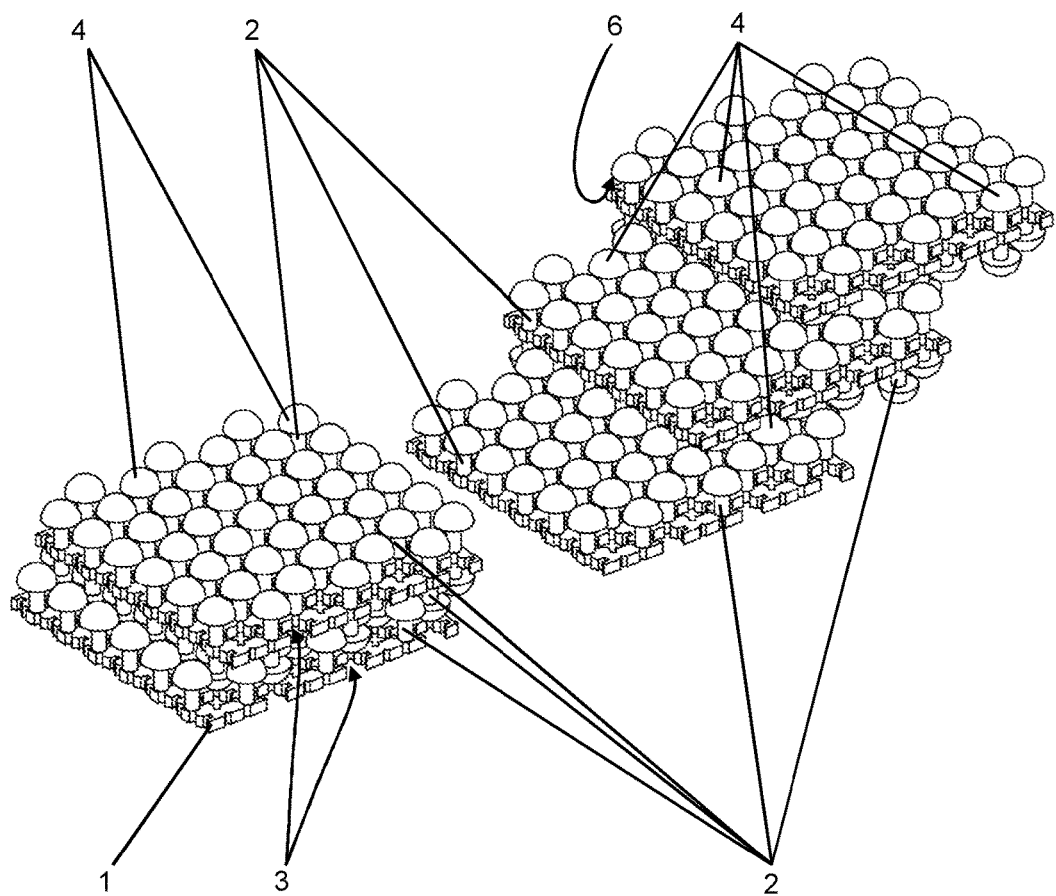

(52) U.S. Cl.
CPC .......... *A61F 2002/3006* (2013.01); *A61F 2002/30299* (2013.01); *A61F 2002/30467* (2013.01); *A61F 2002/30489* (2013.01); *A61F 2002/30677* (2013.01); *A61F 2002/30785* (2013.01); *A61F 2002/30841* (2013.01); *A61F 2002/30971* (2013.01); *A61F 2002/30973* (2013.01); *A61F 2002/3411* (2013.01); *A61F 2310/00011* (2013.01)

(56) References Cited

U.S. PATENT DOCUMENTS

| | | | |
|---|---|---|---|
| 4,290,174 | A | 9/1981 | Kalleberg |
| 5,077,870 | A | 1/1992 | Melbye et al. |
| 8,999,000 | B2 | 4/2015 | Hodorek et al. |
| 2005/0112397 | A1 | 5/2005 | Rolfe et al. |
| 2008/0244878 | A1 | 10/2008 | Hoehe et al. |
| 2010/0001152 | A1 | 1/2010 | Golle et al. |

FOREIGN PATENT DOCUMENTS

| | | |
|---|---|---|
| DE | 1610318 A1 | 10/1970 |
| DE | 10006822 A1 | 8/2001 |
| DE | 102004048464 A1 | 4/2006 |
| DE | 102006015100 A1 | 10/2007 |
| DE | 102006015145 A1 | 10/2007 |
| DE | 102006015148 A1 | 10/2007 |
| EP | 2832320 A1 | 4/2015 |
| WO | 2013/074909 A1 | 5/2013 |

OTHER PUBLICATIONS

German Office Action for corresponding German Application No. 10 2015 107 559.7 dated Jan. 12, 2016.

Australian Office Action for corresponding Australian Application No. 2016202848 dated Mar. 17, 2016.

PLANAR BONE REPLACEMENT MATERIAL AND METHOD FOR PRODUCING A POROUS BODY

This application claims priority of German patent application DE 10 2015 107 599.7 filing date May 13, 2015, the entire contents of which German patent application are incorporated herein by reference.

The invention relates to an alloplastic bone replacement material. The invention also relates to a method for producing a porous body from an alloplastic bone replacement material.

Accordingly, the subject of the invention is an alloplastic bone replacement material intended for filling and stabilising bone cavities. Moreover, the invention proposes a method for producing a free-formed porous body.

Bone replacement materials have been known for a long time and are used extensively in clinical applications (J. M. Rueger: Knochenersatzmittel, Orthopäde 27 (1998) 72-79.). The bone replacement materials used thus far are generally stable in volume, but not stable in shape. One notable exception is a bone replacement material that is distributed by the name of "Trabecular Metal™" by Zimmer and is known, for example from WO 2013/074 909 A1. Said material has a porous structure made to imitate the structure of human cancellous bone (sponge tissue). Said material consists of tantalum and is commercial in defined shapes and sizes. The material cannot be changed in shape and size in a surgical theatre. It cannot be processed with conventional tools in a surgical theatre. Therefore, the individual anatomical situation of the patient can be taken into account only to a limited degree. The medical user is left to attempt to adapt the implant bed to the given geometry or to insert an approximately fitting implant and to close the existing gaps with allogenic bone material or other volume fillers.

Especially in the reconstruction of acetabular roof defects in the scope of septic revision surgeries of infected hip prostheses, it is extremely important to substitute and bridge the missing bone substance in mechanically stable manner such that so-called revision acetabulum cups can be implanted.

Accordingly, it is the object of the invention to overcome the disadvantages of the prior art. Specifically, a bone replacement material for augmentation is to be developed that is well-suited for filling and bridging bone defects and can be formed for said purpose. The bone replacement material is to form a shape-stable porous body once it is formed without any need for chemical curing reactions, such as, for example, radical polymerisations. The bone replacement material is to possess open porosity and is to be mechanically stable after the forming process. In this context, the porosity and the size of the pores shall be sufficient and appropriate such that human bone of a patient treated with the bone replacement material can grow into the pores of the bone replacement material. Another aim is to have the bone replacement material, in the formed state, be as load-bearing as possible. Moreover, the bone replacement material must be biocompatible such that it can be inserted into the body of a patient.

The objects of the invention are met by a planar alloplastic bone replacement material comprising at least one plate, preferably comprising multiple plates, for augmentation of bone defects, whereby the bone replacement material consists of a biocompatible plastic material, a biocompatible metal and/or a biocompatible metal alloy, whereby the at least one plate comprises a planar structure and comprises a plurality of pins extending outwards from the planar structure of the at least one plate, whereby the pins each comprise at least one connecting element, whereby the pins are deformable elastically and are arranged sufficiently close to each other such that pressing the surfaces of multiple plates onto each other causes the connecting elements of different plates to interlock with and/or snap into each other and the plates that are interlocked with and/or snapped into each other form an open-pored body of plates that are interlocked with and/or snapped into each other.

According to the invention, biocompatible metals or biocompatible metal alloys are preferred for producing the plates of the bone replacement material.

Interlocking means that projections of the connecting elements of the pins of the plates engage projections, gripping surfaces or undercuts of connecting elements on pins of neighbouring plates such that the pins then are still mobile with respect to each other by pressing the plates further together, but can no longer be readily separated from each other. Snapping-in means that the connecting elements of the pins of the plates appropriately engage connecting elements of pins of neighbouring plates such that the plates can no longer be separated from each other, but can also not be moved towards each other any longer by pressing the plates further together. Accordingly, the connecting elements can be provided by means of hooks, grooves, undercuts, snap-in means and/or opposite snap-in means and/or by hooks, grooves, undercuts and/or snap-in elements.

According to the invention, the at least one plate and the three-dimensional body formed by multiple plates are preferably osteoconductive.

Theoretically, a single plate, for example one that can be folded once or multiple times to produce the desired three-dimensional body, can be sufficient. However, according to the invention, the bone replacement material comprises multiple plates that can be joined. Particularly preferably, the bone replacement material comprises multiple plates of different shapes that can be joined. The selection of the shape of the plates in this context is governed by the treatment scenario.

The term, "planar", shall be understood to mean planar bodies and bodies derived from planar bodies that are each formed from one closed or, preferably, one perforated, plate-like base body. Perforated planar structures are preferred in this context because bone tissue can grow into the surface through said perforations and/or the pores formed by the perforation. It is particularly advantageous and preferred according to the invention to have one perforation and/or one pore arranged in the plate next to each pin. In this case, the interlocking and/or the snapping-in of multiple plates, i.e. of multiple planar augmentation materials, leads to the formation of an open porous body that is osteoconductive if the material is selected properly, such as, for example, tantalum.

According to the invention, the plates of the bone replacement material contacting each other form a mechanically stable composite upon exposure to a pressure.

The invention can provide the connecting elements of bone replacement materials according to the invention to be mushrooms, hooks, undercuts and/or snap-in elements, preferably mushrooms, hooks, undercuts, snap-in means and/or opposite snap-in means.

Said connecting elements are particularly well-suited for snapping into and/or interlocking with each other. Textile connecting elements, such as hook and loop fasteners with easily deformable fibers, however, are not suitable according to the invention, since no dimensionally stable and pressure-resistant bodies can be built up by them.

The invention can also provide the distance between the connecting elements and the planar structure of the at least one plate to be between 0.3 mm and 2 mm, preferably to be between 0.5 mm and 1 mm.

This can ensure that the pores remaining free between the interlocked or snapped-in connecting elements possess a sufficient diameter for an open-pored structure. As a result, the three-dimensional body made of bone replacement material thus produced is osteoconductive.

Moreover, the invention can provide the pins of the at least one plate to extend perpendicular or at an angle between 60° and 90°, preferably at an angle between 80° and 90°, out of the planar structure of the at least one plate.

As a result, the plates are particularly easy to connect to each other later on. Moreover, the load bearing capacity of the bone replacement material is thus made to be uniform.

The invention also proposes the connecting elements to be provided at the jacket surface of the pins.

As a result, a stable connection of the pins, and thus of the plates, to each other can be attained.

Preferred bone replacement materials can be provided appropriately such that plates pressed into each other interlock and/or snap-in irreversibly.

This ensures that no particles of the fully formed bone replacement material detach from the body thus formed. This prevents irritation of the treated body at the site of treatment.

A refinement of the present invention proposes the thickness of the at least one plate without projecting pins to be at most 1.5 mm, preferably the thickness to be between 0.25 mm and 1.5 mm, particularly preferably the thickness to be between 0.5 mm and 1 mm.

The thickness of the at least one plate is the dimension of the plate without the pins that are arranged perpendicular to the planar structure of the plate. As a result, the plates can be bent and/or deformed sufficiently such that they can be adapted to the treatment scenario.

Moreover, the invention can provide the at least one plate to be produced with a generative 3D printing method.

As a result, the plates, and thus the bone replacement material, can be produced inexpensively.

According to a preferred embodiment, the invention can provide at least one of the at least one connecting elements per pin to have a truncated cone shape, whereby the longitudinal axes of the pins form the longitudinal axes of the cones and whereby the jacket of the cones faces toward the outer side that faces away from the planar structure of the at least one plate.

As a result, the at least one plate can be connected in particularly stable manner by means of the connecting elements shaped as truncated cones. Moreover, said shaping prevents surrounding soft tissue and bone tissue from being injured after the implantation of the bone replacement material.

Moreover, the invention can provide at least one of the at least one connecting elements per pin in the form of a hook and/or as a mushroom head.

The hooks and/or the mushroom heads provide for stable and non-detachable connection of the plates to each other. If the connecting elements are mushroom head-shaped, they can possess, for example, a collar at the mushroom head edge provided in the direction of the planar structure such that hook-shaped connecting elements of other plates can engage this thus generated undercut, whereby an irreversible, non-detachable interlocked or snapped-in connection between the plates is produced. It is also feasible, and preferred according to the invention, that at least one plate contains various connecting elements or various pins with different connecting elements. Accordingly, a plate can simultaneously possess hooks and mushroom heads as connecting elements, both on the same pin and on different pins.

In a preferred embodiment, the connecting elements are provided as mushroom heads. In a particularly preferred embodiment, the mushroom heads are shaped appropriately such that the mushroom heads comprise a conical undercut on the side facing the surface of the at least one plate. As a result, hook-shaped snap-in elements can be interlocked irreversibly and non-detachably with said mushroom heads. If the shapes of the undercuts and of the mushroom heads match properly, further propulsion of the mushroom heads can be prevented such that the mushroom heads snap into the undercuts.

Particularly preferred bone replacement materials can be provided appropriately such that the pins contain a circumferential groove as additional connecting element between the planar structure of one plate and at least one of the at least one connecting elements, whereby connecting elements of other plates can interlock with or snap into said groove, preferably snap-in appropriately such that no further motion of the connecting elements along the pins is possible.

This also facilitates particularly stable connection of plates to each other. Moreover, it is advantageous in this context that this attains defined and unoccupied hollow spaces as open pores after snap-in connection of the plates in the body thus formed from the bone replacement material. Namely, further closure of the open-pored structure by further propulsion of the pins between the pins of an appended plate is prevented and the pores are thus kept open.

A refinement of the present invention proposes at least two connecting elements to be arranged in succession on the jacket surface of the pins, particularly preferably at least three connecting elements to be arranged in succession on the jacket surface of the pins.

As a result, plates can be interlocked and/or snapped-in at different distances from each other. This attains higher flexibility during the forming of the bone replacement material.

The invention can also provide the at least one plate to have the shape of a square, rectangle, trapezoid, parallelepiped and/or polygon.

By means of these shapes, the bodies made of the bone replacement material can be adapted particularly well to the bones to be filled and/or to be treated.

Moreover, the invention can provide the planar structure of the at least one plate to contain through-going pores, whereby the pores are rounded, in particular the pores comprise no sharp-edged contours, whereby the pores in the planar structure of the plate preferably have a free cross-section between 0.25 mm and 1 mm, particularly preferably between 0.3 mm and 0.9 mm.

This ensures that the pores extend in all directions into the three-dimensional body thus formed so that the bone growth can proceed specifically into the planar structure of the at least one plate.

Moreover, the invention can provide the planar structure of the at least one plate to contain through-going pores, whereby the depth of the pores perpendicular to the planar structure of the at least one plate is at least 0.25 mm, preferably at least 0.4 mm.

This can ensure that the pores are enveloped by the bone both stably and uniformly. The plates thus replicate a spongy tissue that corresponds to a normal bone structure (cancellous bone) and can osseointegrate well with a normal bone structure.

Moreover, the invention can provide the at least one plate to be made from biocompatible plastic material, stainless steel, titanium, a titanium alloy, tantalum, a tantalum alloy or composites of said materials.

Said materials are particularly well-suited for medical purposes and can be used to attain the suitable elastic properties of the pins. It is preferred, according to the invention, to produce plates consisting of metal or metal alloys by selective laser sintering or by melting with electron beams, preferably by a 3D printing method.

The biocompatible plastic material can be biodegradable. Polylactides, polyglycolides, polycaprolactones and polyester formed from different α-hydroxy carboxylic acids can be used for this purpose. Conceivable non-biodegradable plastic materials include polyamides, polyimides, polyetherketone, and polysulfone. Plates made of these non-biodegradable and biodegradable plastic materials can be produced by selective laser sintering According to a refinement, the present invention can provide neighbouring pins that are arranged on the same side of a first plate of the at least one plate to be situated at an appropriate distance from each other such that the pins of the first plate, after elastic deformation due to interlocking with and/or snapping into a connecting element of a second plate of the at least one plate, enable at least two interlocks and/or snap-in connections to at least two further connecting elements of the second plate, preferably enable at least three interlocks and/or snap-in connections to three further connecting elements of the second plate.

Multiple interlocking and/or snap-in connection of the plates allows a particularly stable body to be formed from the bone replacement material.

Preferably, the invention can further provide the plate or at least one of the plates to comprise pins just on one side and to be attachable in planar manner to a bone on the other side, whereby, preferably, sharp tips are provided for this purpose that can be pushed into the bone or eyelets or boreholes are provided in the planar structure of the at least one plate by means of which the at least one plate can be screwed to a bone or attached by other means.

A plate of this type can be used for direct planar attachment to the bone. Eyelets or bore holes allow the bone replacement material and/or the plate to be screwed to the bone tissue and allow any number of further plates of the bone replacement material to be applied onto said plate and to subsequently be interlocked and/or snapped-in. By this means, complex three-dimensional structures of the type that occurs, for example, upon manifestation of acetabular roof defects, can be filled in load-bearing manner. Acetabulum cups can also be anchored on said structures, either cement-free or with bone cement.

Sharp tips can be provided for attachment to the bone surface even if both sides of the at least one plate comprise pins, in which case the tips should project beyond the pins with the connecting elements.

In embodiments having sharp tips, the planar bone replacement material can be anchored by punching the sharp tips into the bone tissue. Building on this substrate, any layers and/or plates of bone replacement material can be applied and interlocked.

The invention can just as well provide the at least one plate or at least one of the at least one plates to comprise pins on both sides.

Plates of this type allow for a layer-by-layer design of the three-dimensional body made of bone replacement material.

Moreover, the invention proposes the at least one plate to be mixed with inorganic or organic particulate bone replacement material and/or autologous or, also, allogenic cancellous bone.

This allows the bone healing and the connection of the bone replacement material to the bone to be accelerated.

Preferably, the invention can just as well provide the at least one plate to be coated with one or more pharmaceutical agents from the groups of antibiotics, bisphosphonates, steroids, non-steroidal anti-inflammatory drugs, growth factors, and cytostatic agents.

As a result, the bone replacement material has a pharmacological effect that contributes to the healing of the patient treated with the bone replacement material. Preferred agents from the group of antibiotics are, in particular, gentamicin, tobramycin, amikacin, vancomycin, teicoplanin, clindamycin, and daptomycin.

According to a further embodiment, the invention can provide the at least one plate or at least one of them as a semi-spherical cup or domed surface or as an arc or as a trough.

By this means, the plates can already be adapted to specific treatment scenarios and thus are particularly well-suited for forming domed structures.

Moreover, the invention proposes the pores of the open-pored body formed from multiple plates to be interconnecting and osteoconductive, whereby the pores preferably have a free cross-section between 0.1 mm and 1 mm, particularly preferably between 0.25 mm and 0.9 mm.

This ensures that the bone can grow well into the pores of the body formed from the bone replacement material.

The invention can just as well provide that the at least one plate can be plastically or elastically deformed in the planar structure.

As a result, the at least one plate can be adapted particularly easily to various treatment scenarios.

A refinement of the present invention proposes the pins having connecting elements to be arranged in rows of three or more pins each and a strip of unoccupied surface of the at least one plate to remain between these three or more rows each or to provide a grouped or nested arrangement of pins having connecting elements.

By this means, space is afforded for the deformation of the pins having the connecting elements upon the interlocking and/or snap-in connection.

According to a preferred refinement, the present invention can provide the bone replacement material to comprise at least one particle aside from the at least one plate, whereby the at least one particle comprises a core and at least six pins extending from the core, whereby the pins each comprise at least one connecting element that is designed in analogous manner to the connecting elements of the at least one plates such that the at least one plate and the at least one particle interlock with and/or snap into each other by pressing the connecting elements of the at least one plate and of the at least one particle onto each other, and whereby the plate(s) and particle(s) that are interlocked with and/or snapped into each other form an open-pored body of plate(s) and particle(s) that are interlocked with and/or snapped into each other.

As a result, an even more versatile bone replacement material is attained that can be free-formed and used to bridge gaps and cavities.

The objects underlying the present invention are also met by a method for forming a body made of a planar alloplastic bone replacement material according to the invention comprising multiple plates, in which multiple plates are pushed against each other, whereby the plates interlock with and/or snap into each other and form an open-pored body.

Said method can also provide for the pins with the connecting elements of at least two plates to be contacted to each other and for the pins with the connecting elements to be mutually interlocked and/or snapped-in by pressing the plates against each other.

The invention can just as well provide that at least one of the plates is being connected to a porous three-dimensional body of a second bone replacement material by snapping-in and/or interlocking the connecting elements with the pores of the second bone replacement material, and/or at least one of the plates are being connected to a particulate third bone replacement material comprising multiple particles, whereby the particles of the third bone replacement material comprise a plurality of pins that extend from a core of the particles and have connecting elements, whereby, preferably, the pins and the connecting elements of the particles of the third bone replacement material comprise the features of the pins and connecting elements of the at least one plate of the bone replacement material according to the invention.

The porous three-dimensional body of the second bone replacement material can, for example, be a Trabecular Metal™ made by Zimmer.

The underlying objects are also met through the use of the planar alloplastic bone replacement material according to the invention as implant material in trauma surgery, orthopaedics or veterinary medicine.

According to the invention, the plates of the bone replacement material contacting each other form a mechanically stable composite upon exposure to a pressure.

The invention is based on finding, surprisingly, that plates that snap-in and/or interlock mechanically can be used as alloplastic bone replacement material. In this context, the plates can be arranged layer-by-layer or just partially overlapping, whereby the thus formed porous three-dimensional body is firm and solid after formation of the desired three-dimensional structure without any need to have chemical curing reactions, such as, for example, radical polymerisations. Preferably, the plates are flexible to a limited extent and can thus be brought into the fitting shape and can be interlocked with each other and can thus be connected to each other by exerting a pressure. When the shaped plates snap into each other and/or interlock with each other, the plates mutually stabilise each other such that the resulting three-dimensional body made of the bone replacement material is firm and dimensionally stable. Connecting the plates by pushing them against each other from various directions at sufficient force ensures that a sufficient number of interlocks and snap-in connections is made such that the open-pored three-dimensional body thus generated is dimensionally stable and mechanically durable. Based on a suitable shape and size of the plates, a porous bone replacement material that is mechanically sufficiently stable for medical application is thus formed. The bone can grow into the pores of the bone replacement material connected by pressure and can thus become connected permanently to the bone replacement material.

It has been found, surprisingly, that the planar bone replacement material according to the invention can be placed, in the form of plates, layer-by-layer against surfaces of different shapes and can be cured into a porous, but homogeneous body through interlinking and/or snap-in connection of the individual layers of the planar augmentation material and/or bone replacement material by simple compression by hand or by means of a pestle. This is advantageous as compared to the previous "Trabecular Metal™" bone replacement material, whose shape and size cannot be freely determined by the medical user. It is thus feasible to fill or bridge bone defects of any shape with an in-situ curing and/or hardening augmentation material without needing any chemical reactions, such as for example radical polymerisations, for this purpose. The bone replacement material according to the invention can be cured easily by simply compressing plates whose surfaces are placed against each other. The planar augmentation material according to the invention makes a load-bearing augmentation feasible.

Mechanically interlocked systems following the design principles of hook and loop fasteners have been known for several decades. The principle of the hook and loop fastener was first described by de Mestral in CH 295 638 A. Said principle has been developed further and is put to use in a wide range of reversibly closing Velcro closures. Exemplary refinements are described in the publications, DE 1 610 318 A1, DE 1 625 396 A1, U.S. Pat. Nos. 5,077,870 A, and 4,290,174 A.

An interesting refinement followed later, in which reversibly hook-and-loop-closing steel belt systems for high mechanical load applications and applications at high temperatures were developed (DE 10 2004 048 464 A1, DE 10 2006 015 100 A1, DE 10 2006 015 145 A1, DE 10 2006 015 148 A1).

In the scope of the present invention, it has been evident, surprisingly, that said systems and/or said functional principles can be used for bone replacement materials and/or can be transferred to bone replacement materials. In this context, it is advantageous for the bone replacement materials that connections of this type do not close tightly, but rather gaps remain as an open-pored structure. Bone can grow into the interconnecting pores thus formed in the solid such that the pores allow a stable connection between the bone and the bone replacement material to be generated. For this purpose, one must make sure that the pores in the bone replacement material have a sufficient free cross-section. The pores are called osteoconductive, if the bone can grow into the pores and can thus become connected to the body formed from the bone replacement material.

An exemplary and, according to the invention, particularly preferred embodiment of the present invention is a planar augmentation material, in which three or more elastically deformable pins possessing at least one snap-in element each on a pin end are arranged on at least one surface of a planar structure formed from a biocompatible metal or metal alloy, and whereby the three or more pins are situated appropriately close to each other such that contact of the pins of at least two planar structures and exposure to pressure causes these to interlock with and/or snap into each other and thus form a composite of the planar augmentation materials.

In this context, the plates are designed appropriately such that pressing the plates together causes contacting plates to snap-in or interlock irreversibly and to form an open-pored body made of plates that are interlocked with or snapped into each other.

Figure 2:
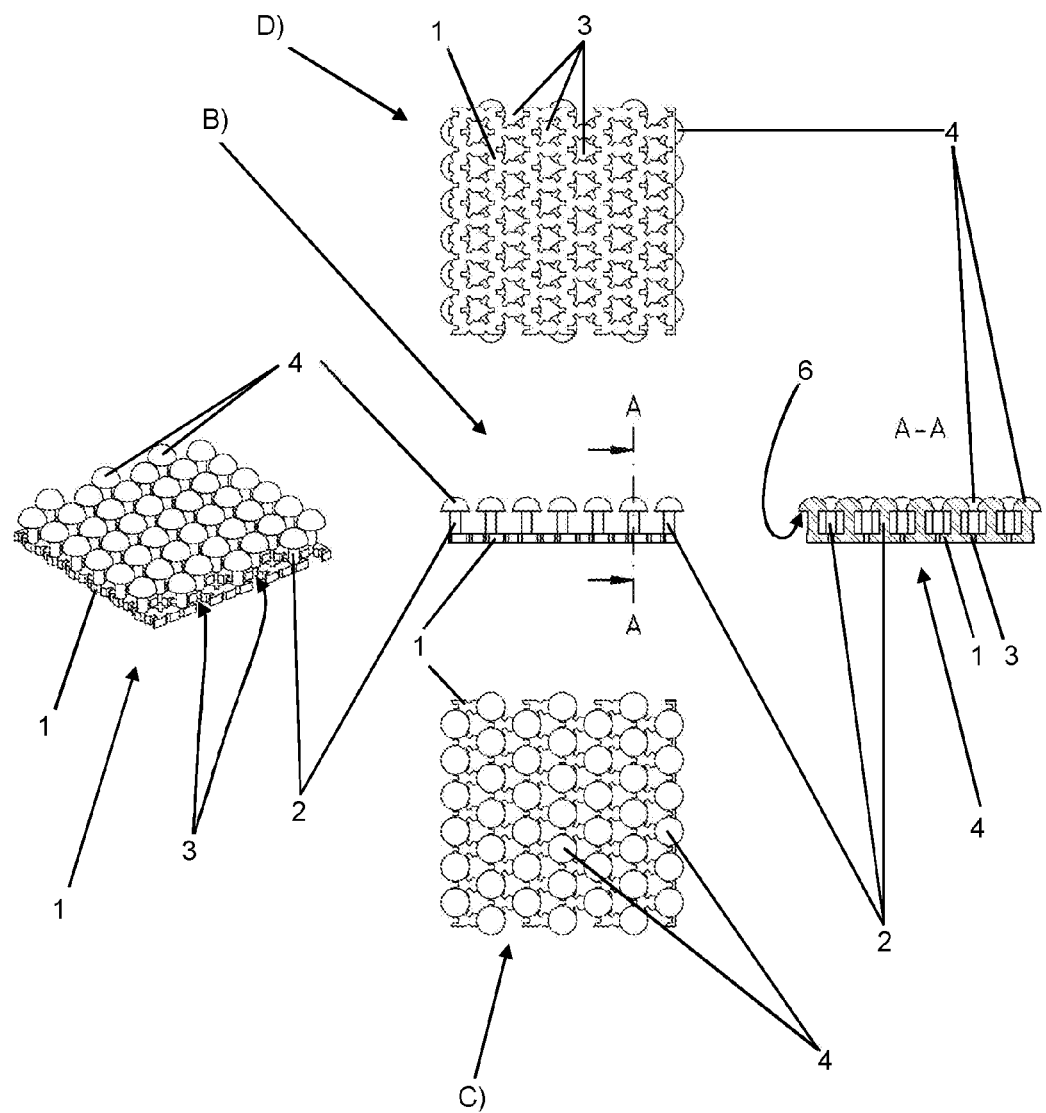
Figure 3:
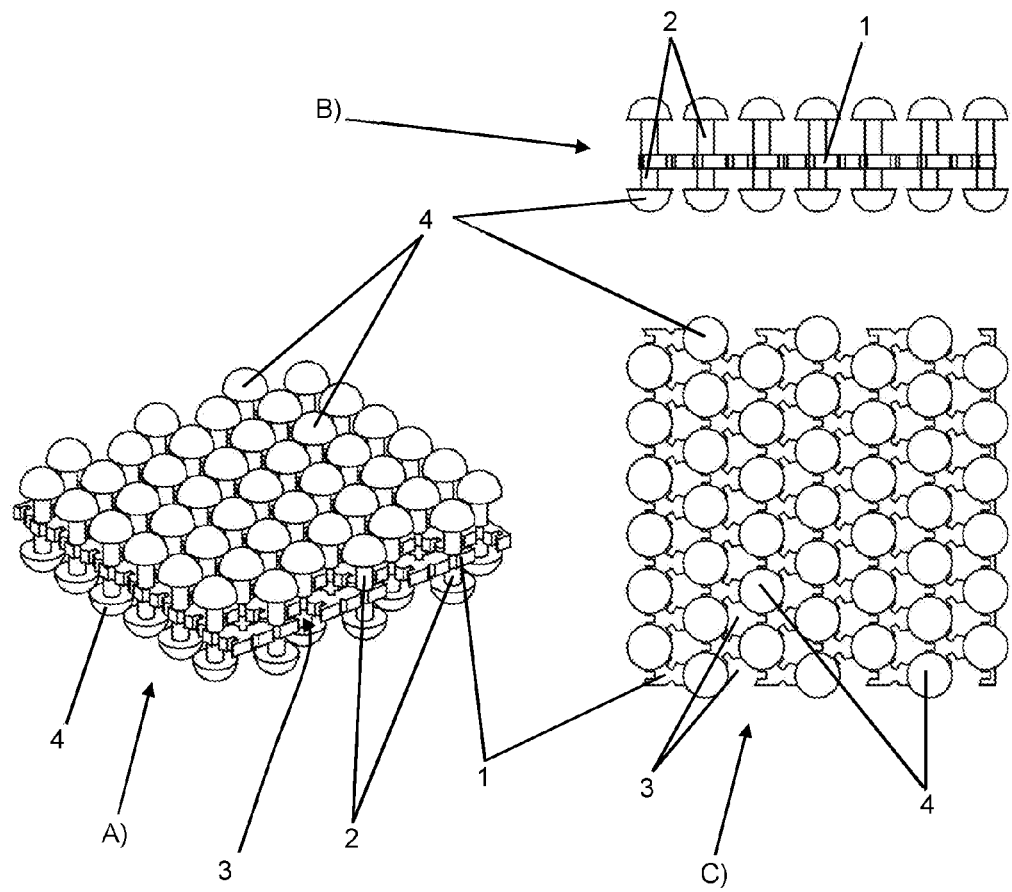
Figure 4:
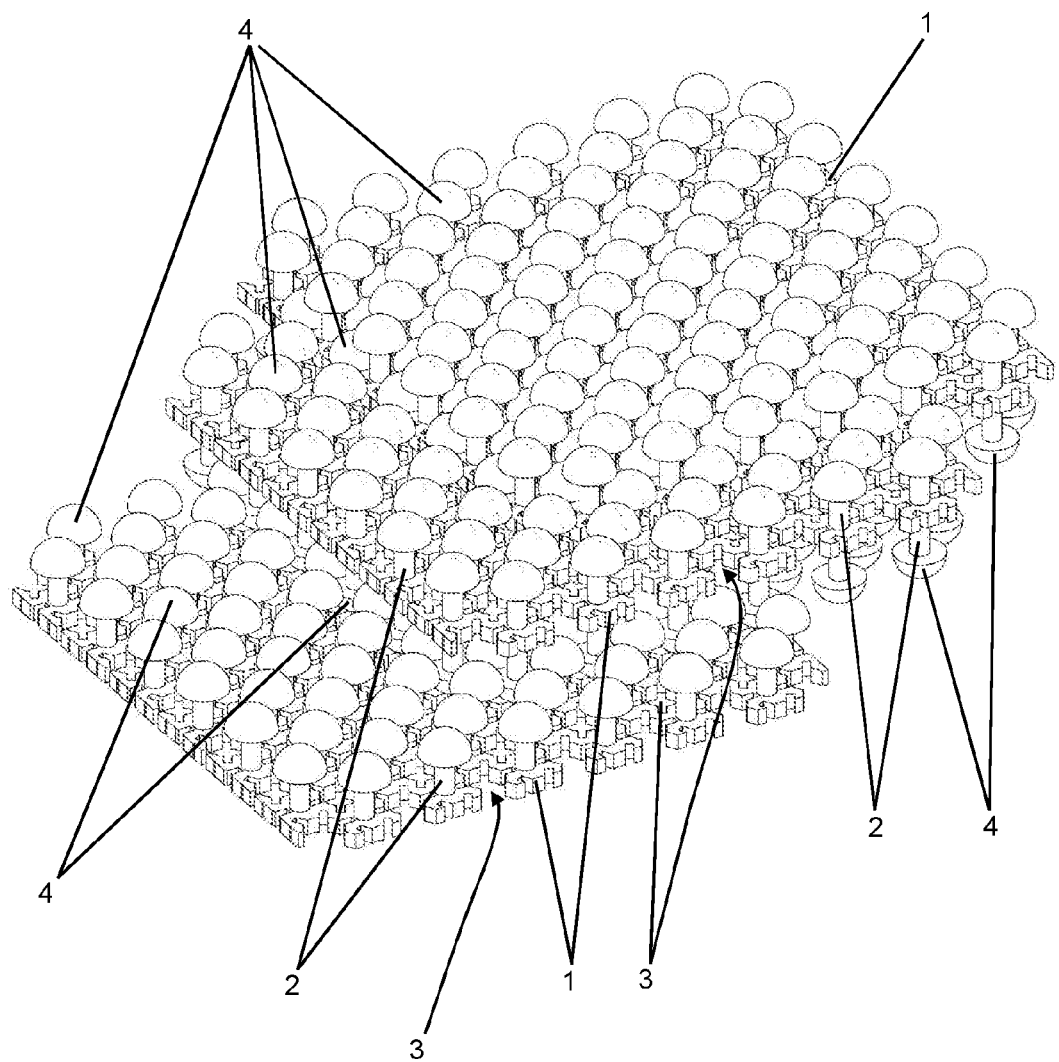
Figure 5:
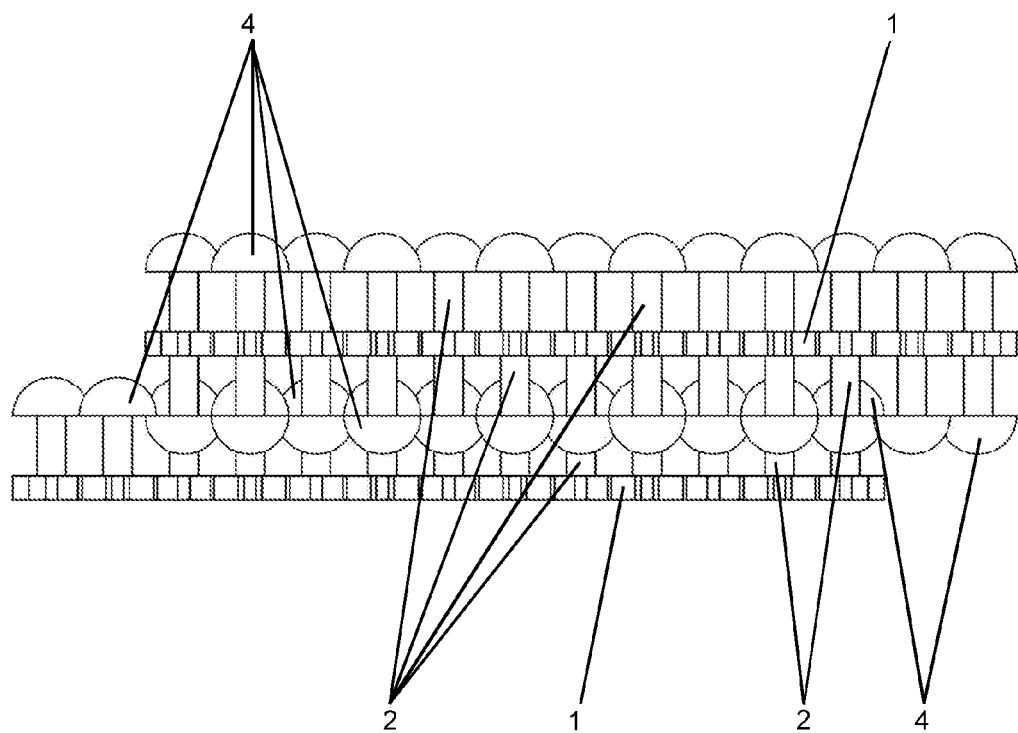
Figure 6:
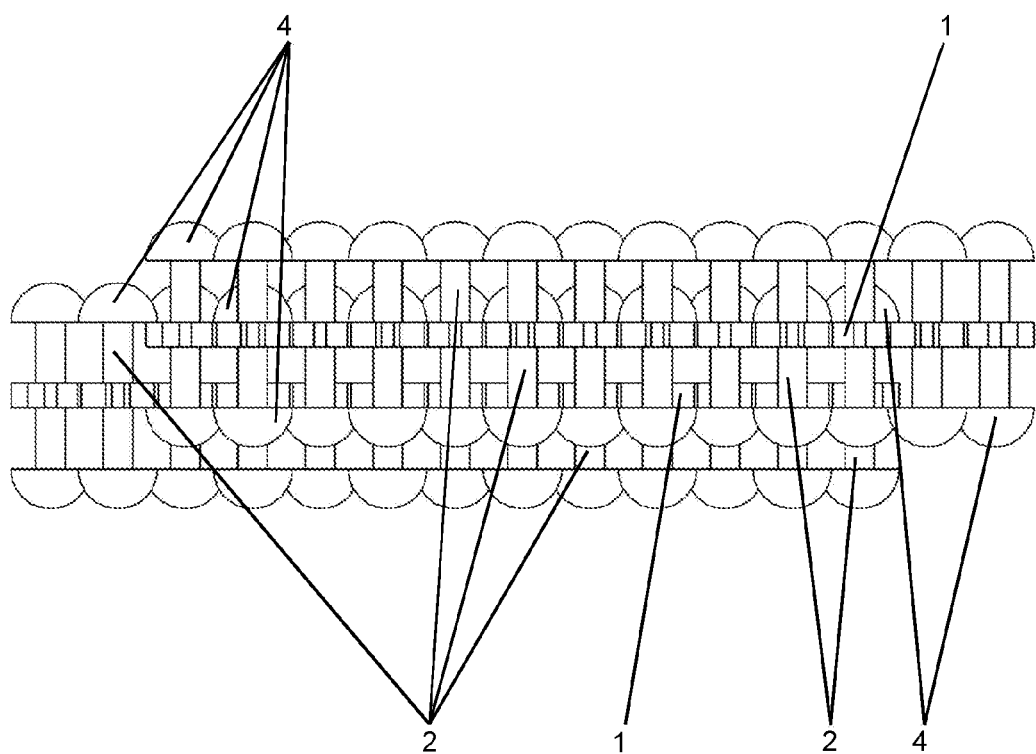
Figure 7:
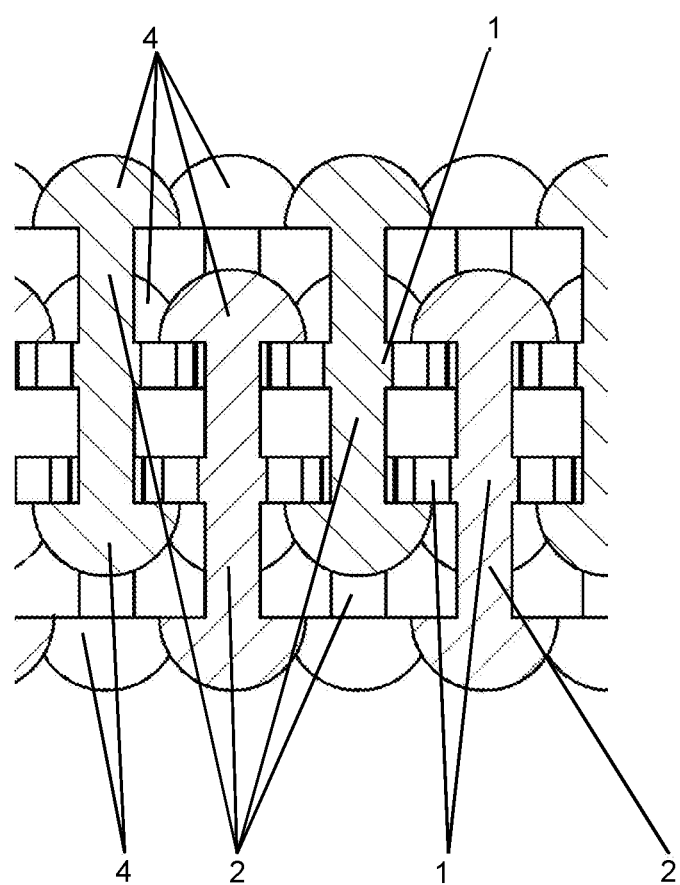
Figure 8:
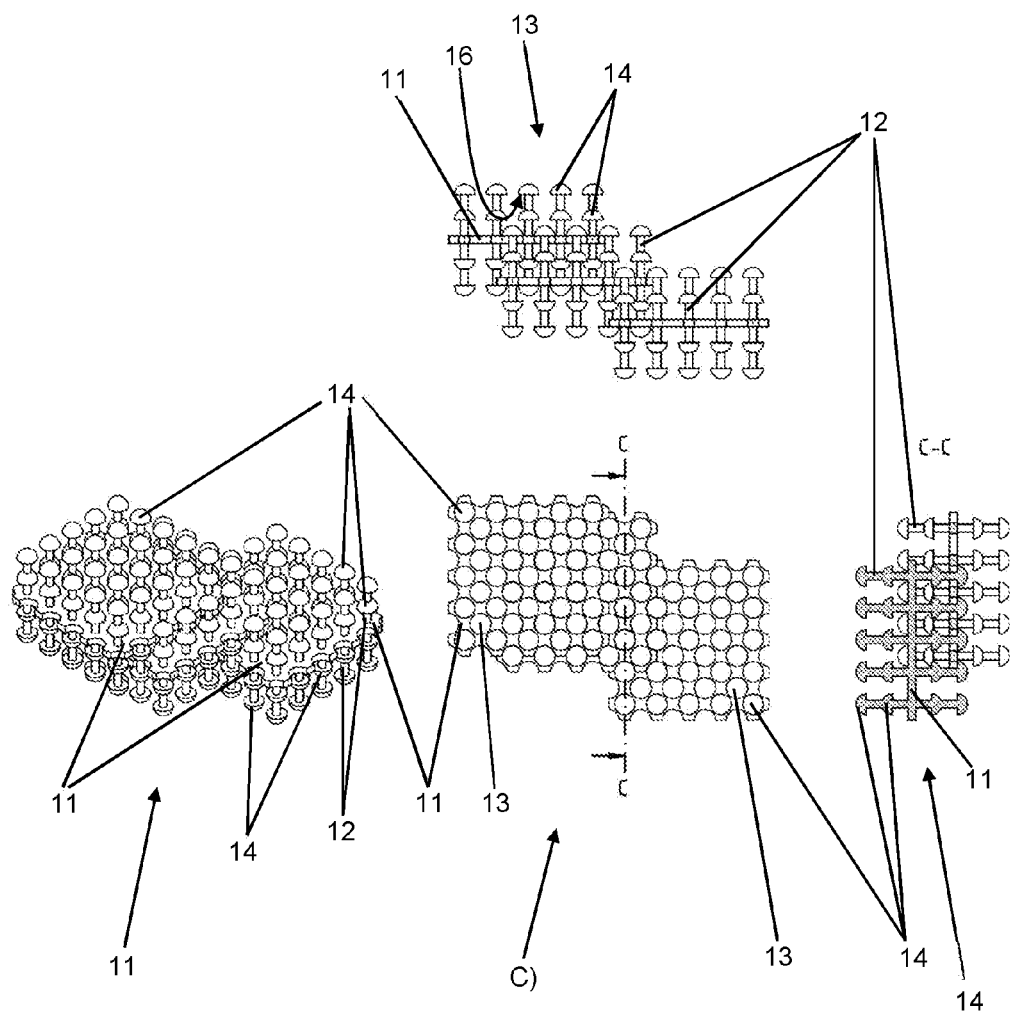
Figure 9:
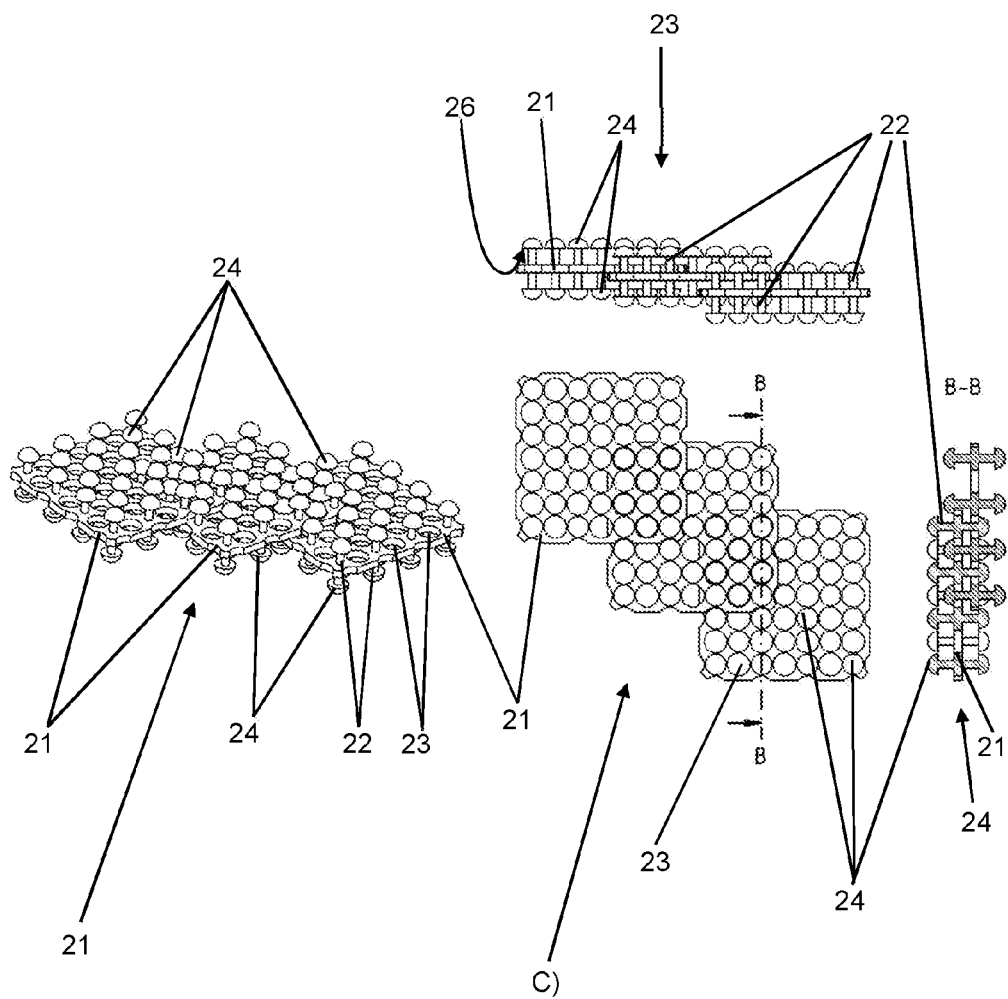
Figure 10:
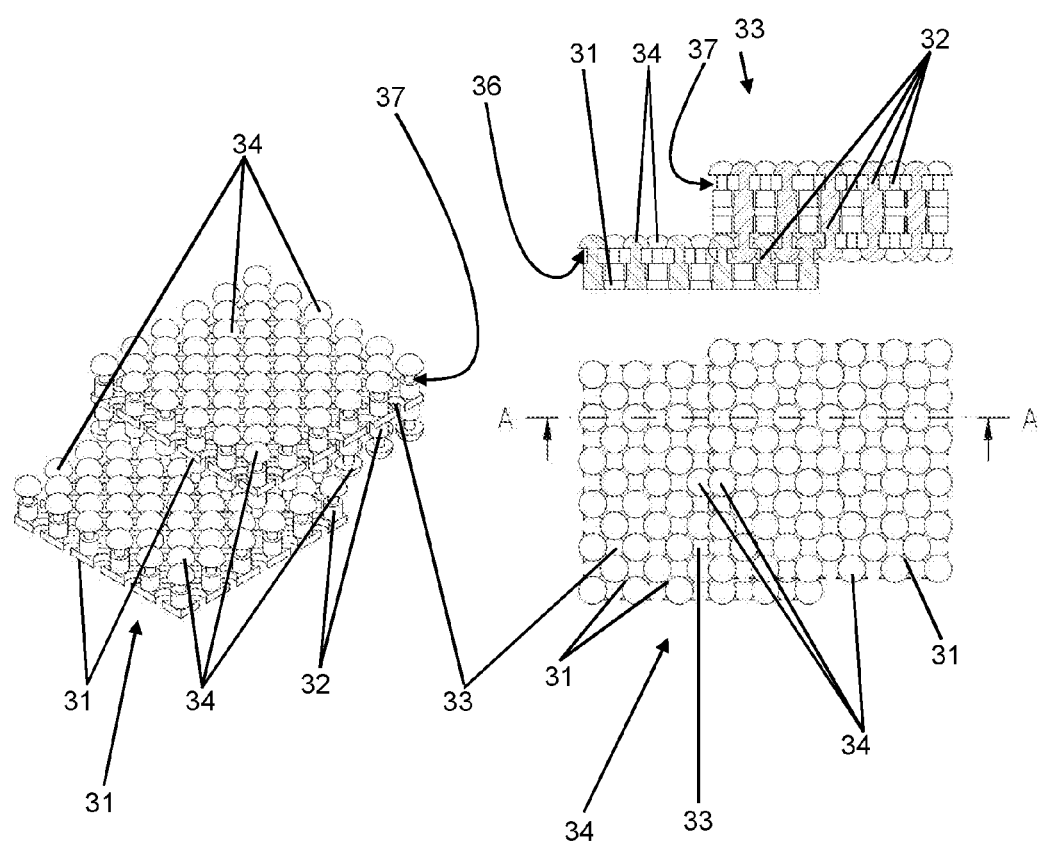
Figure 11:
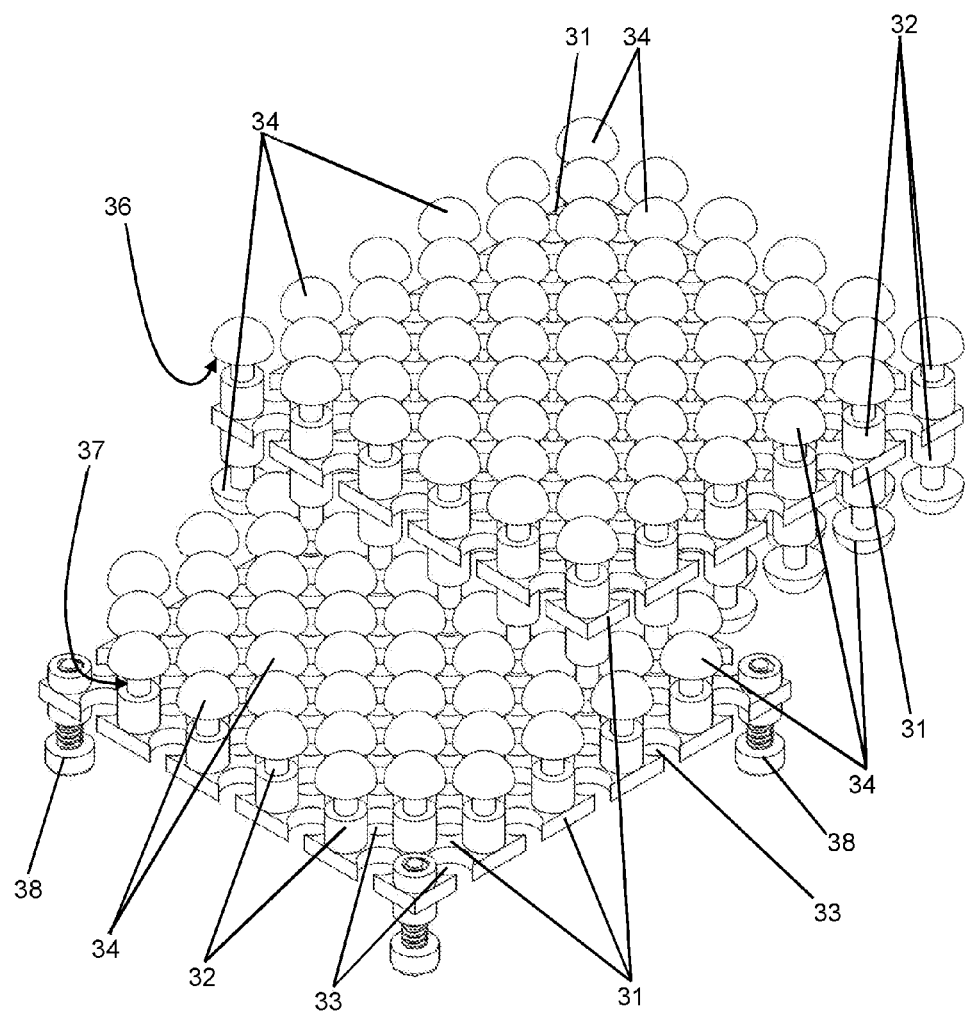
Figure 12:
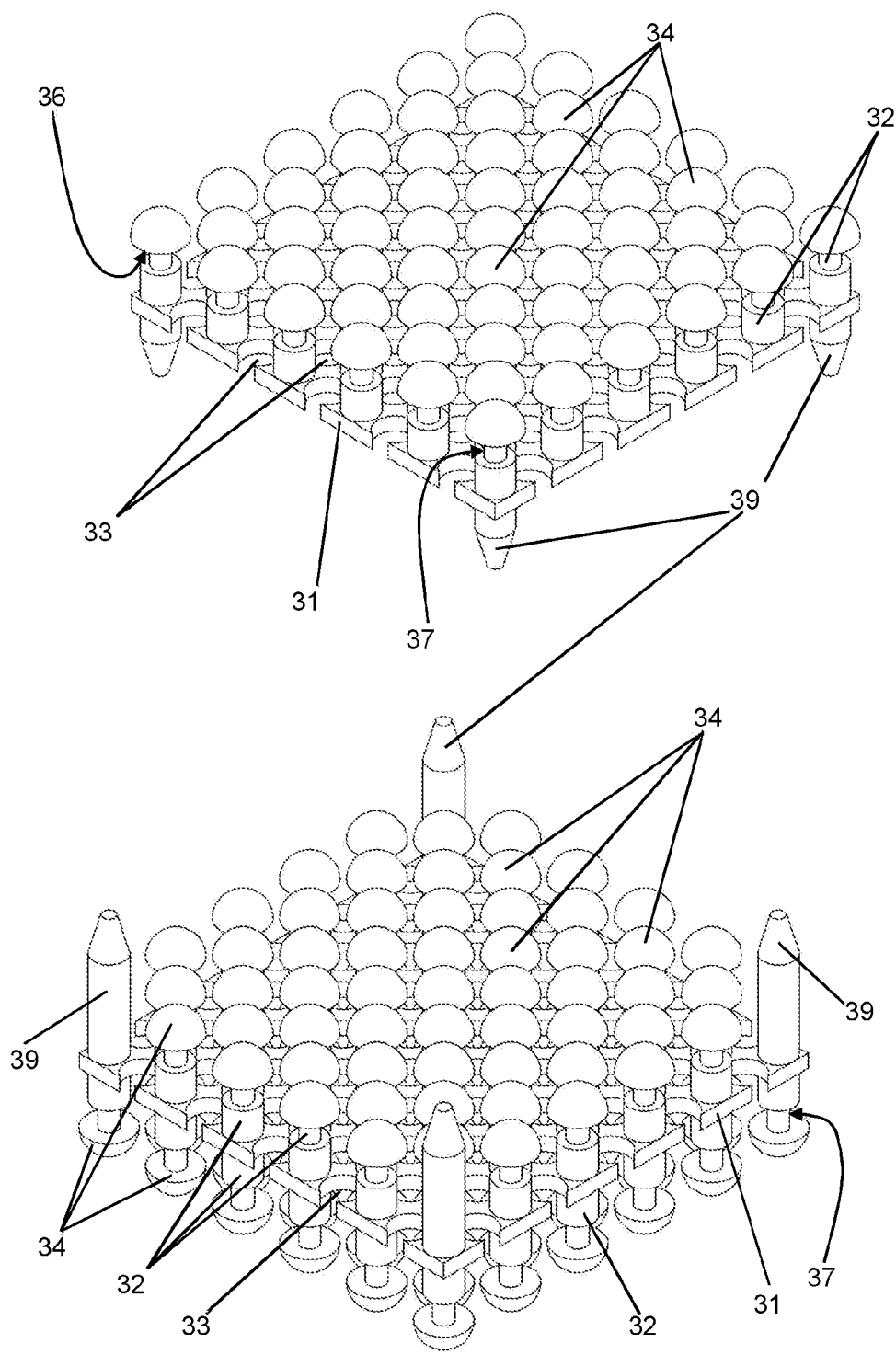
Figure 13:
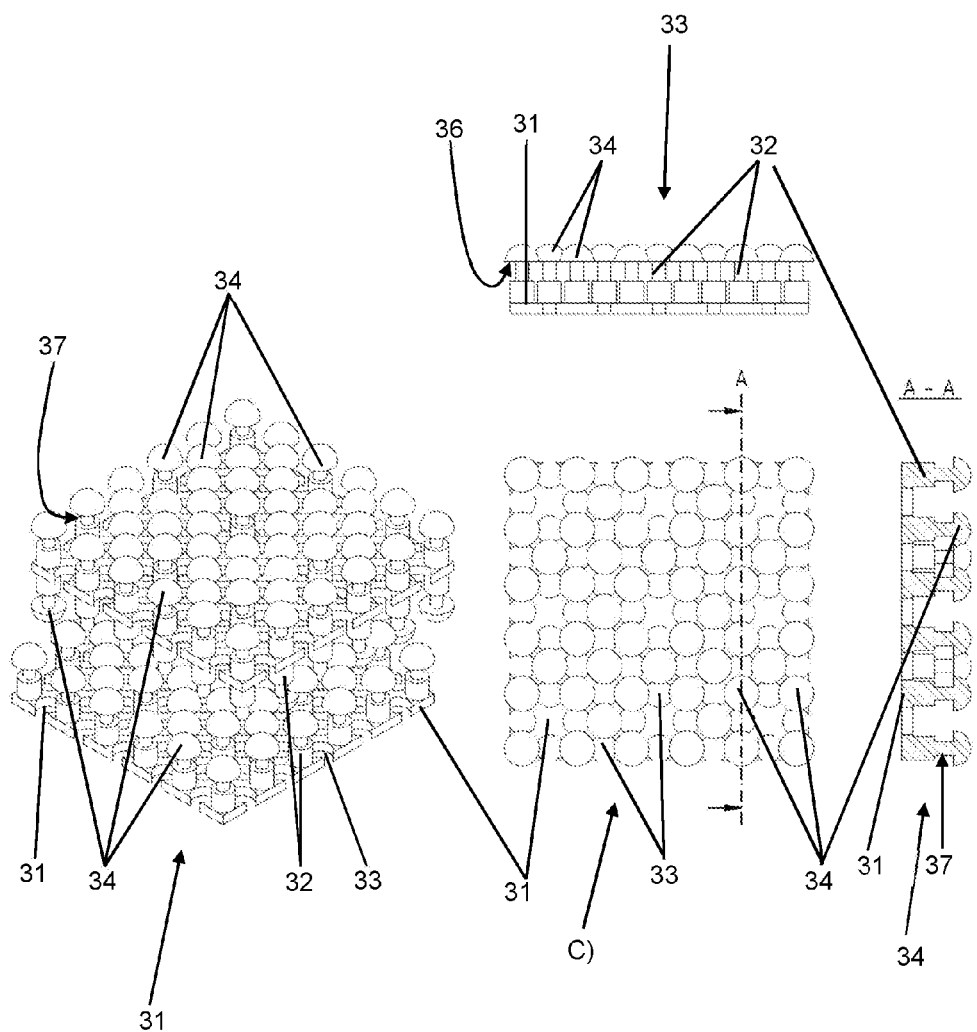
Figure 14:
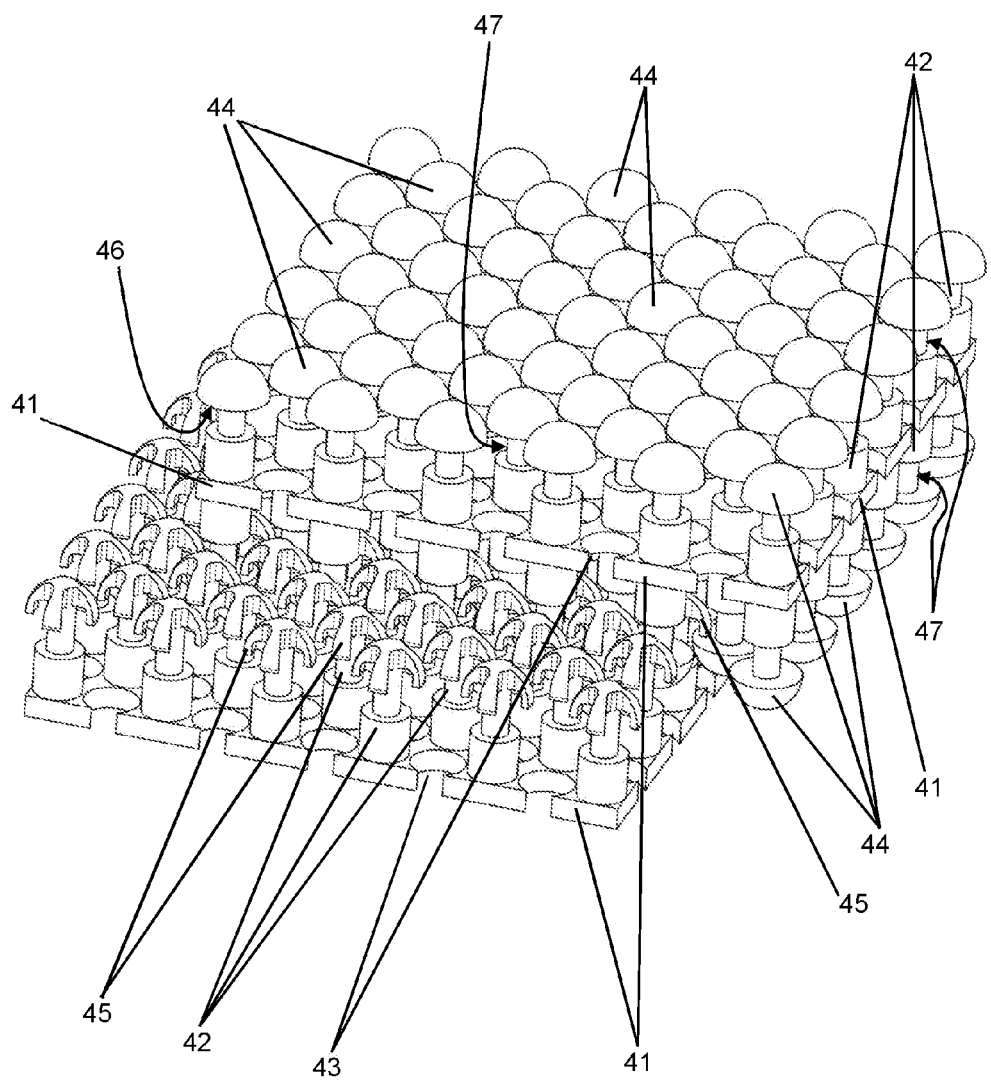
Figure 15:
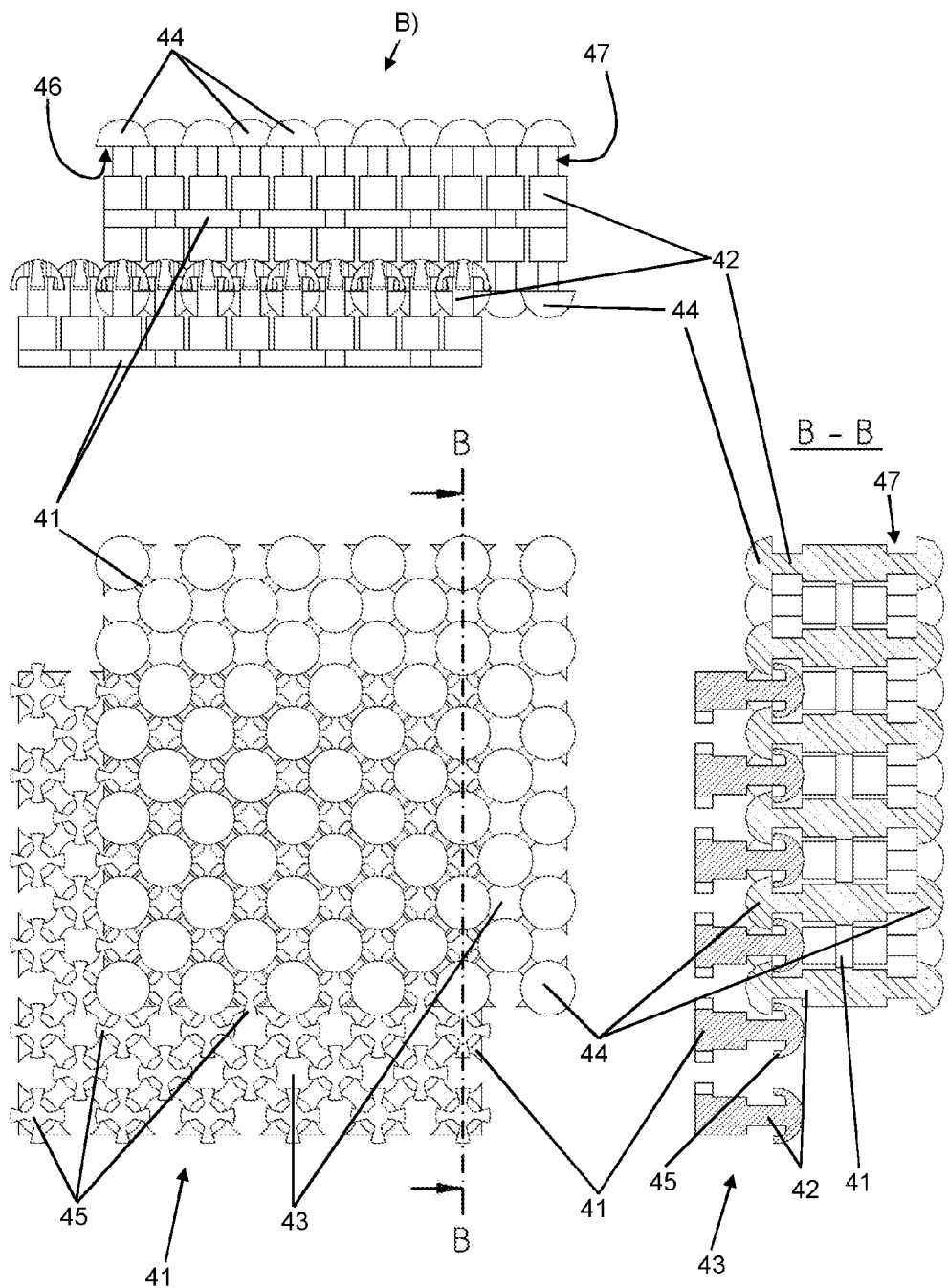
Figure 16:
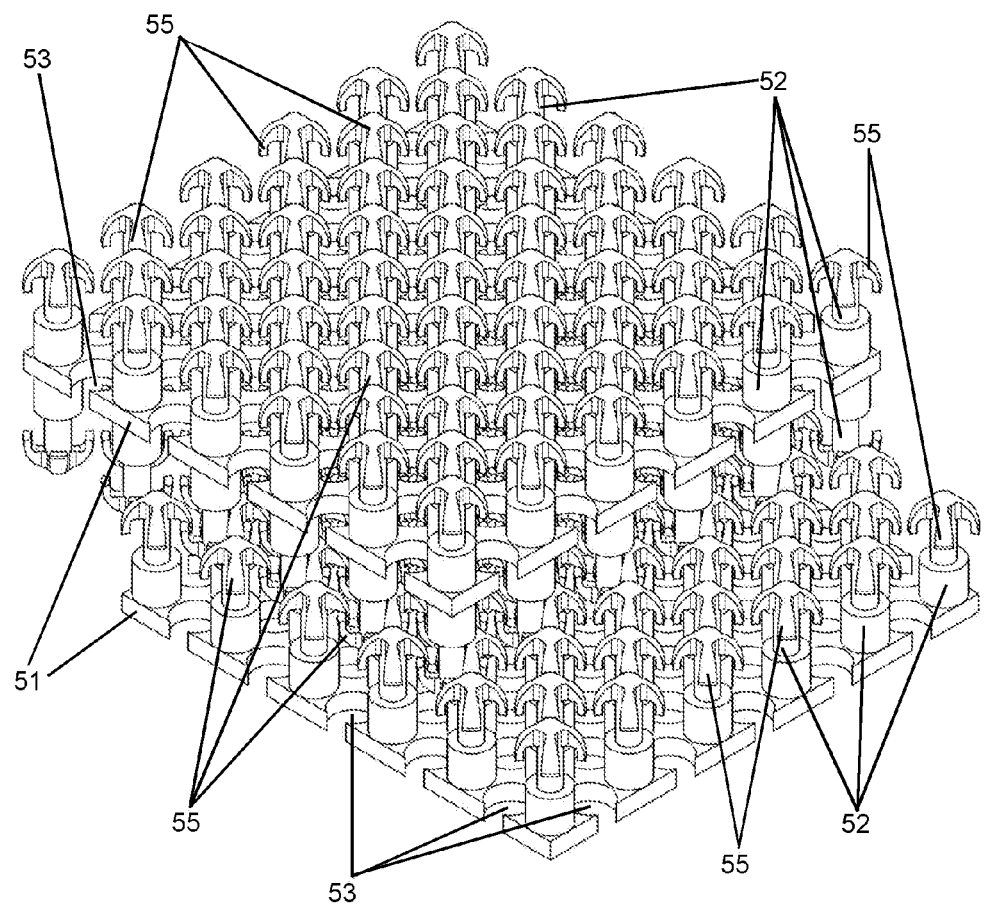
Figure 17:
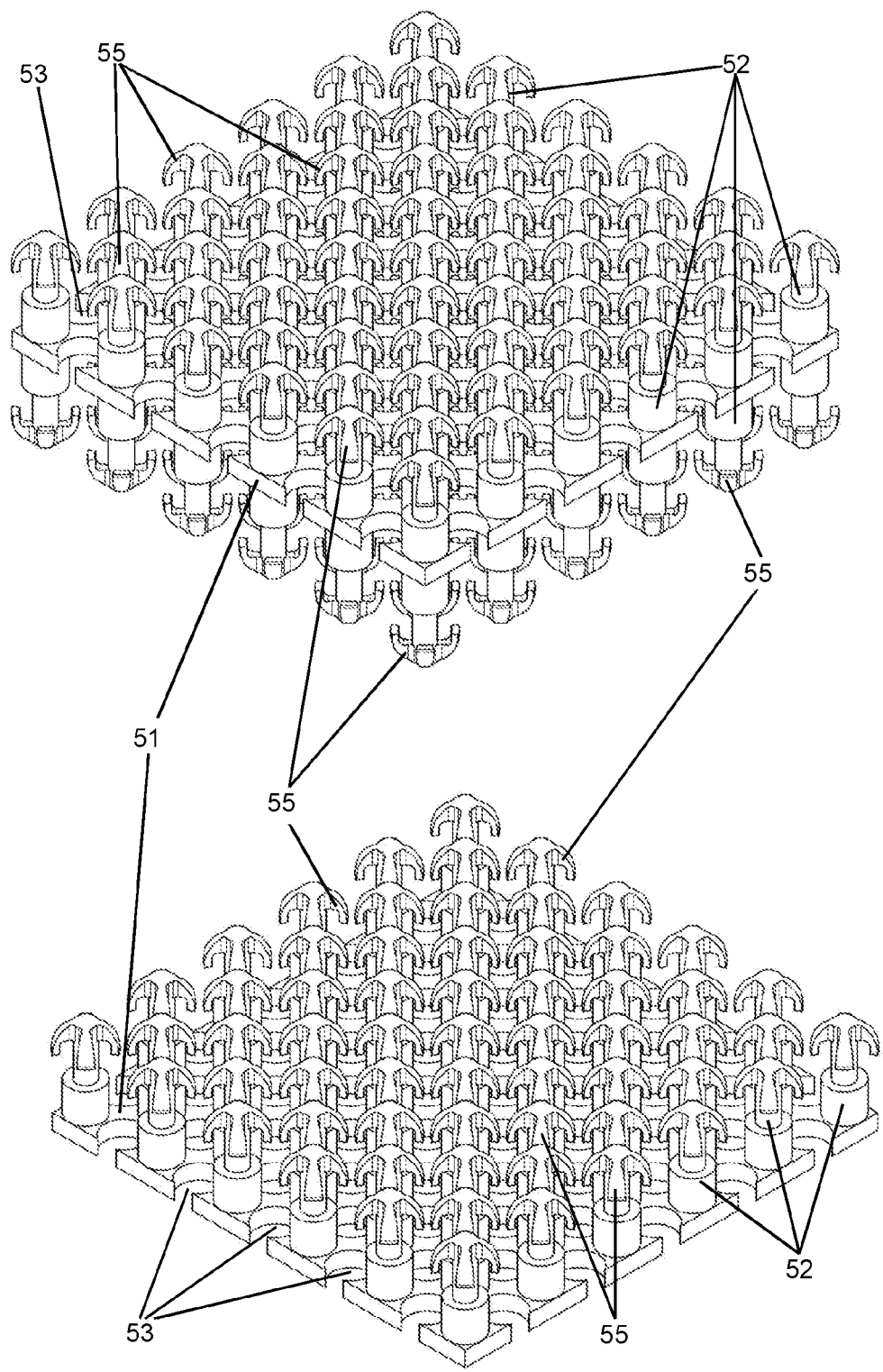
Figure 18:
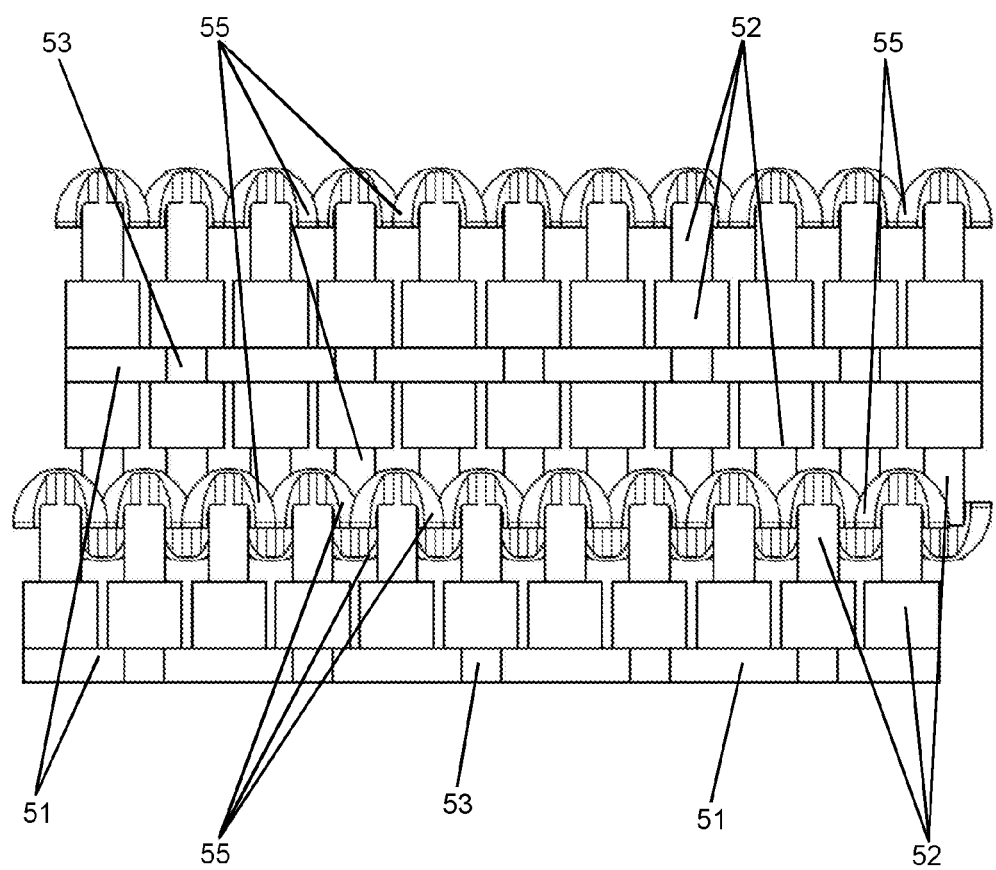
Figure 19:
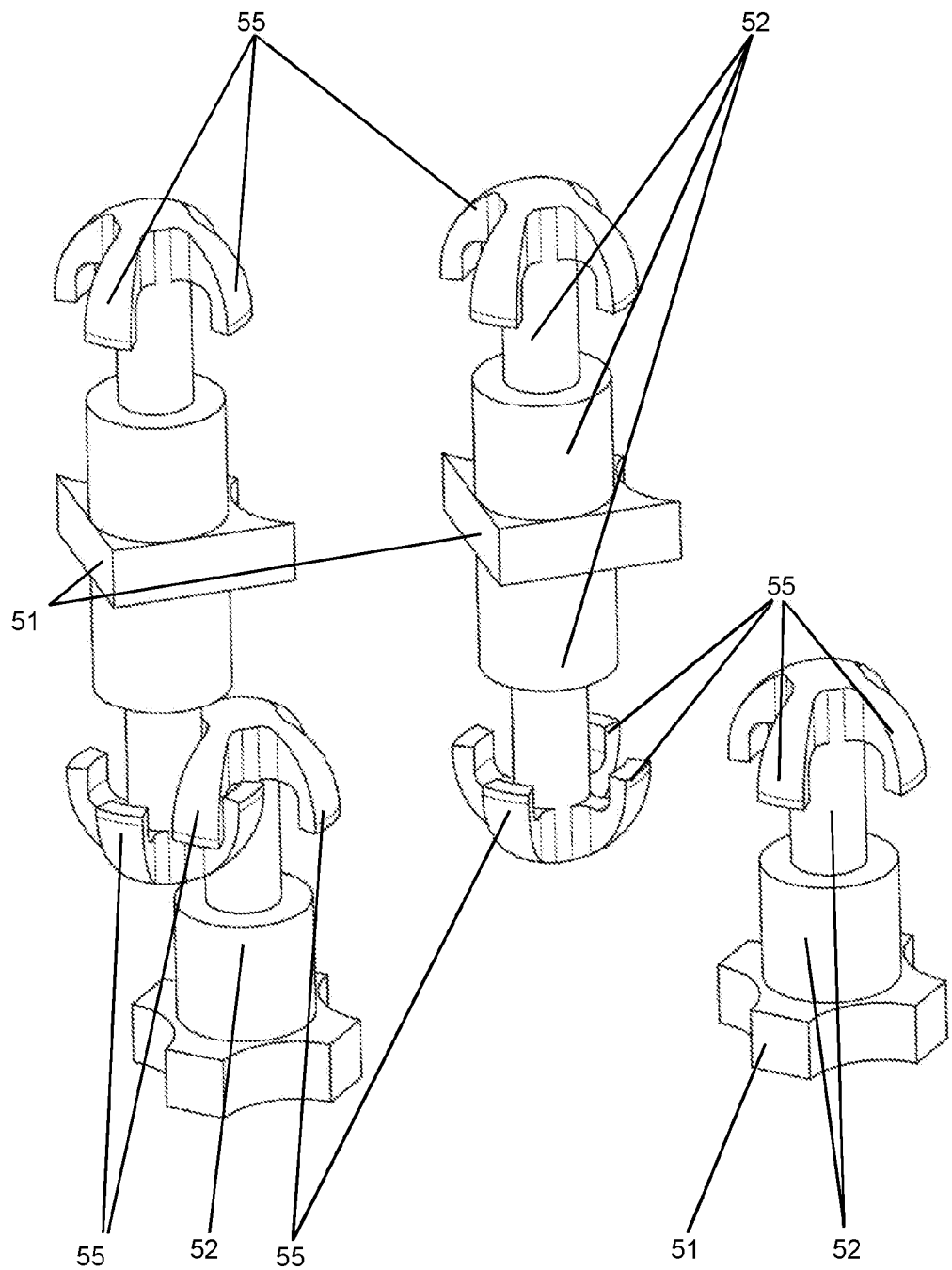
Figure 20:
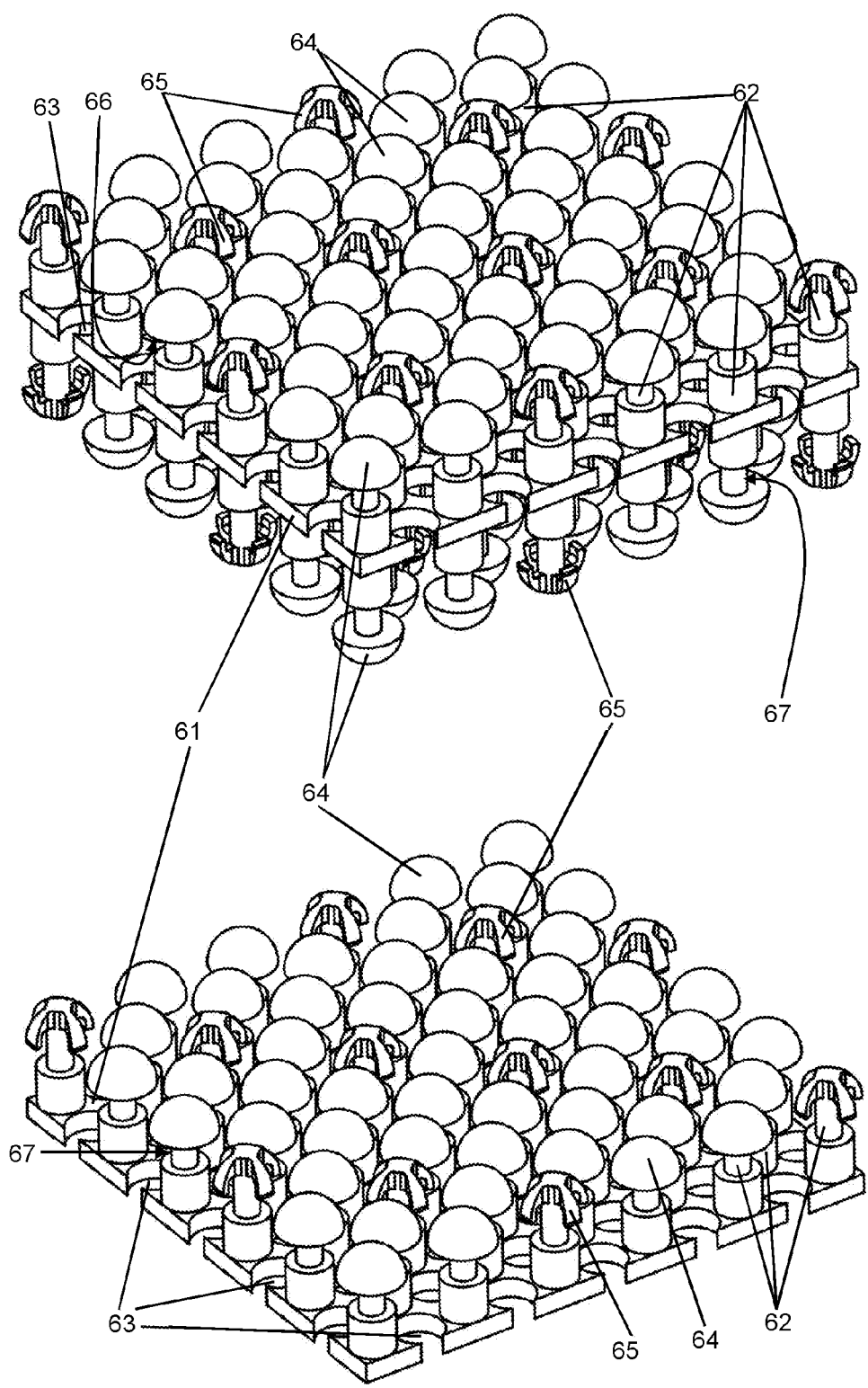
Figure 21:
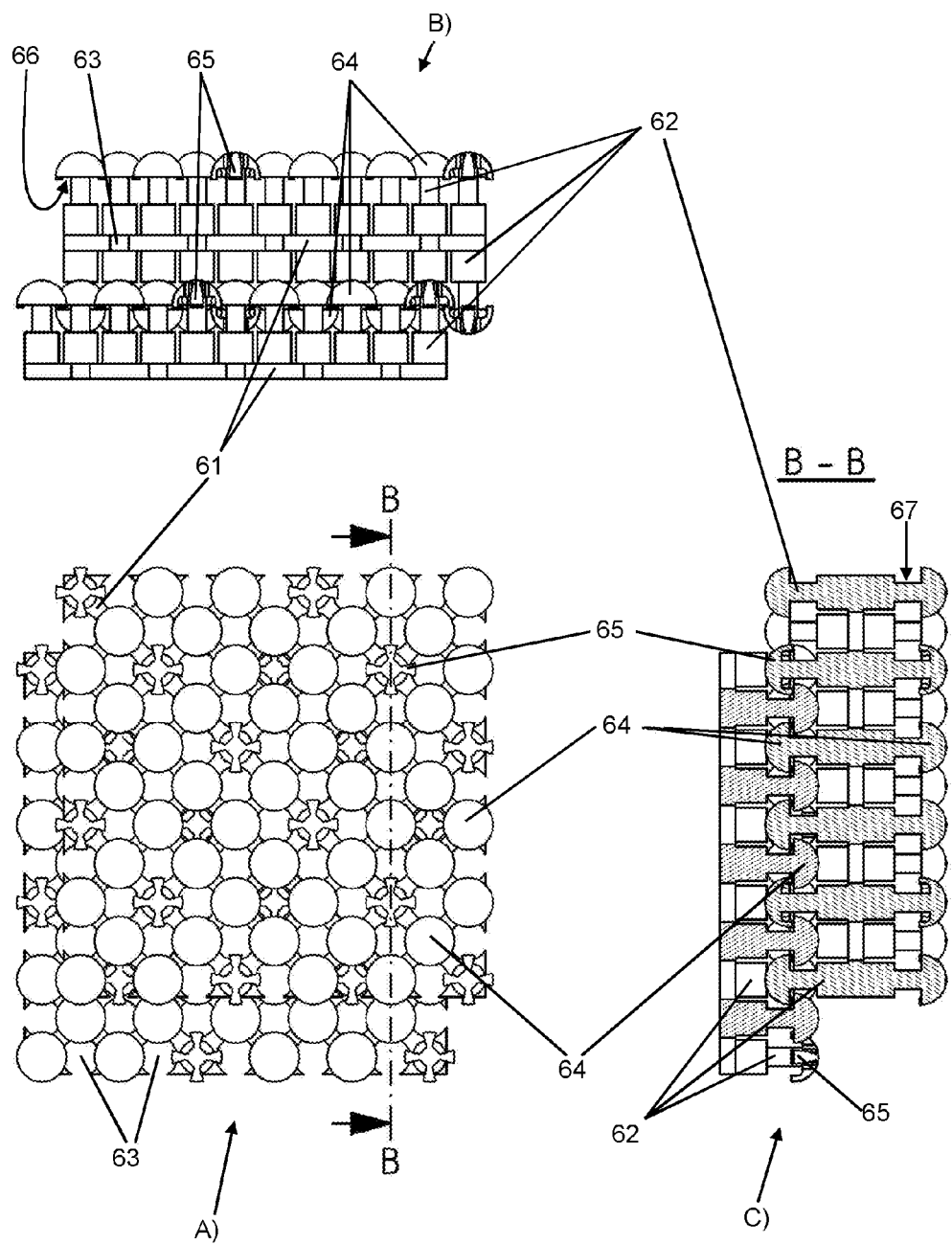
Figure 22:
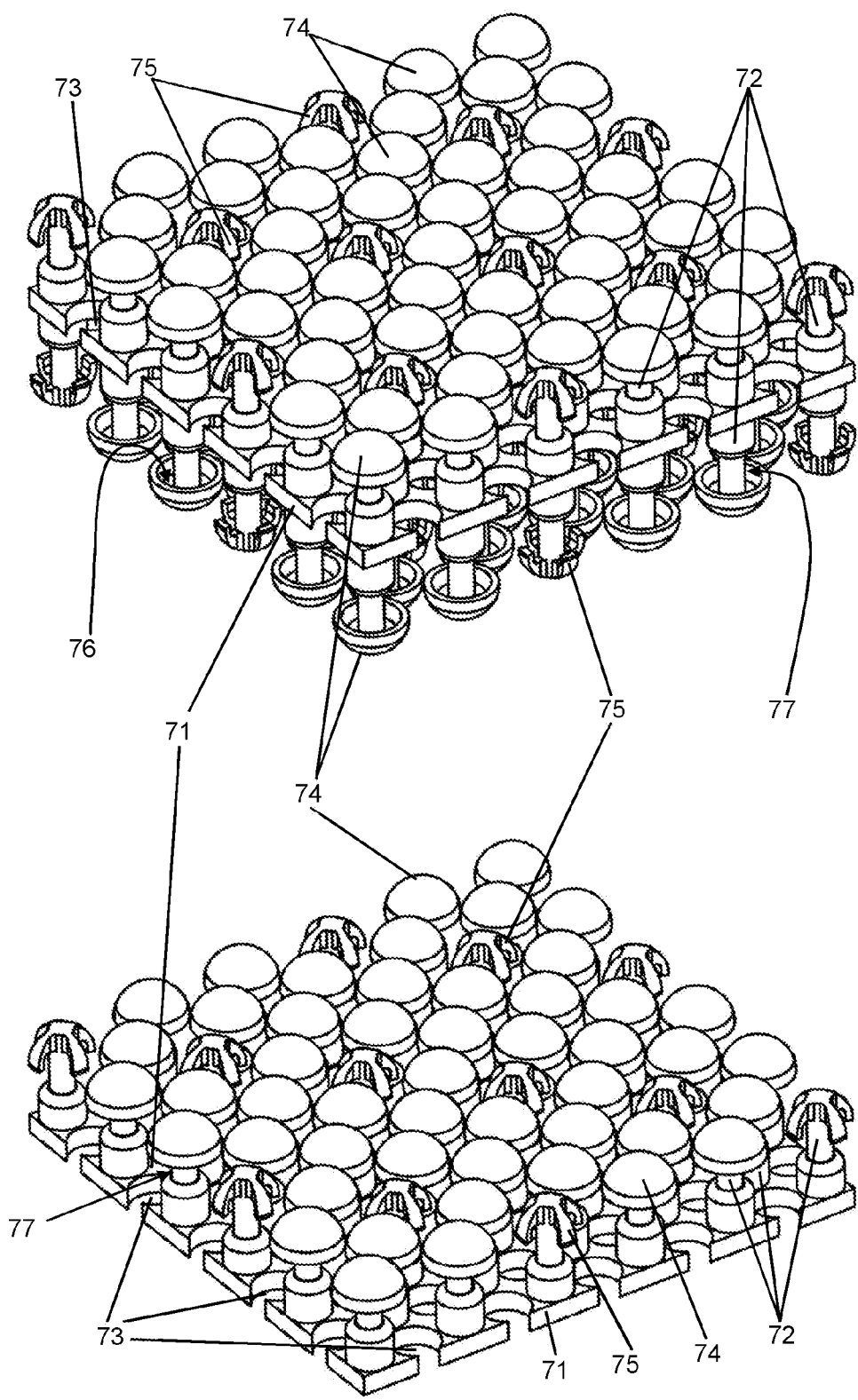
Figure 23:
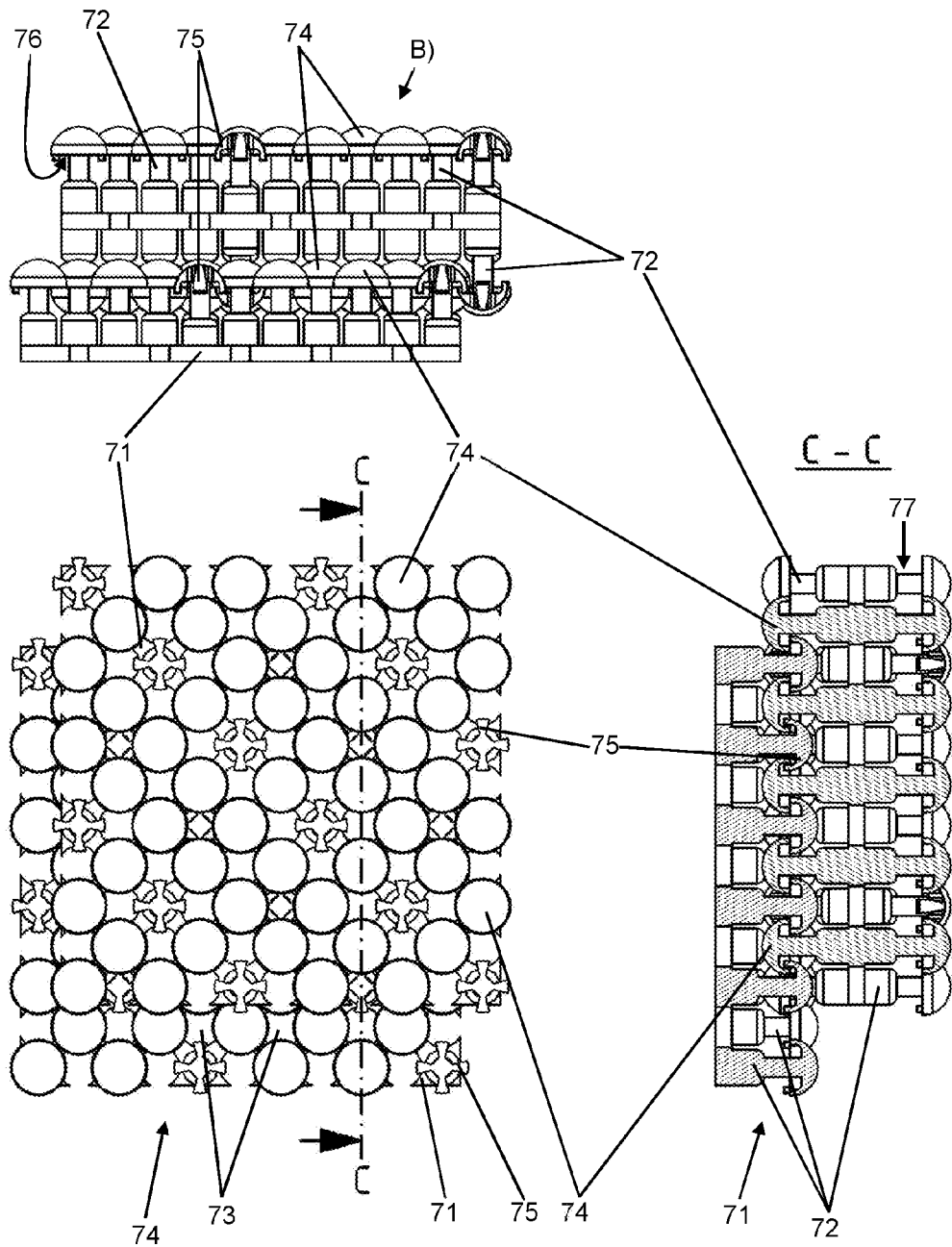
Figure 24:
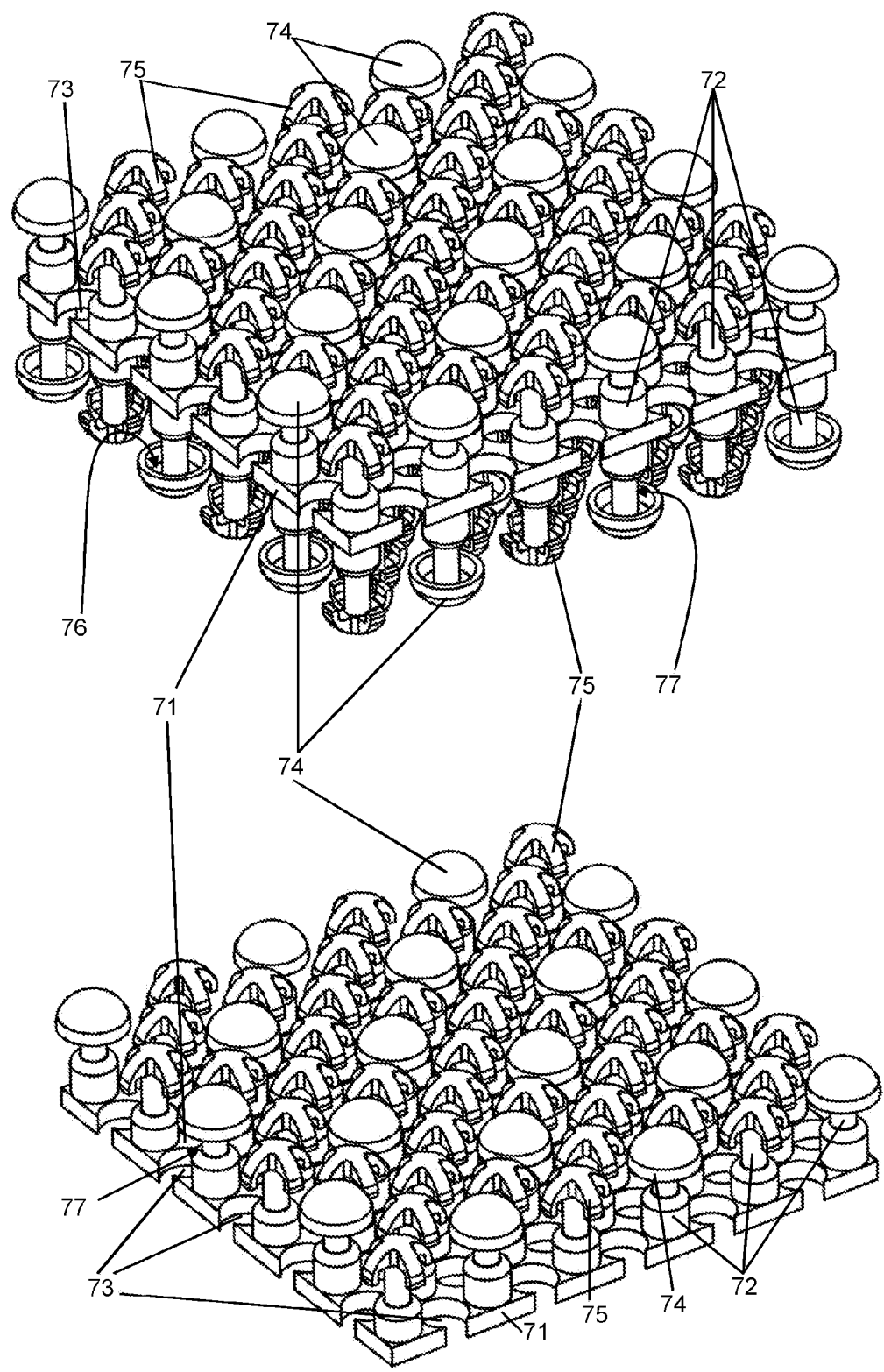
Figure 25:
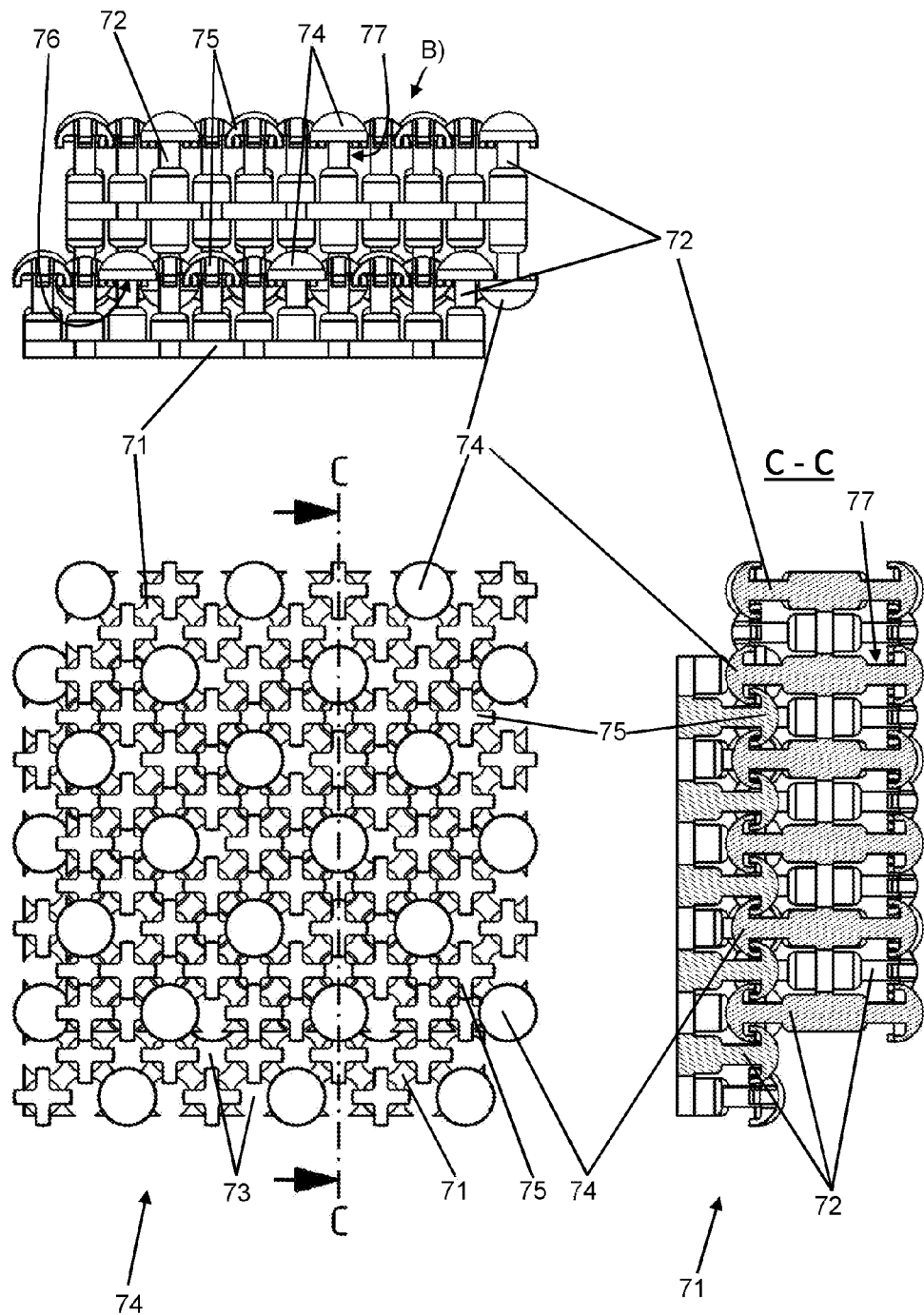
Figure 26:
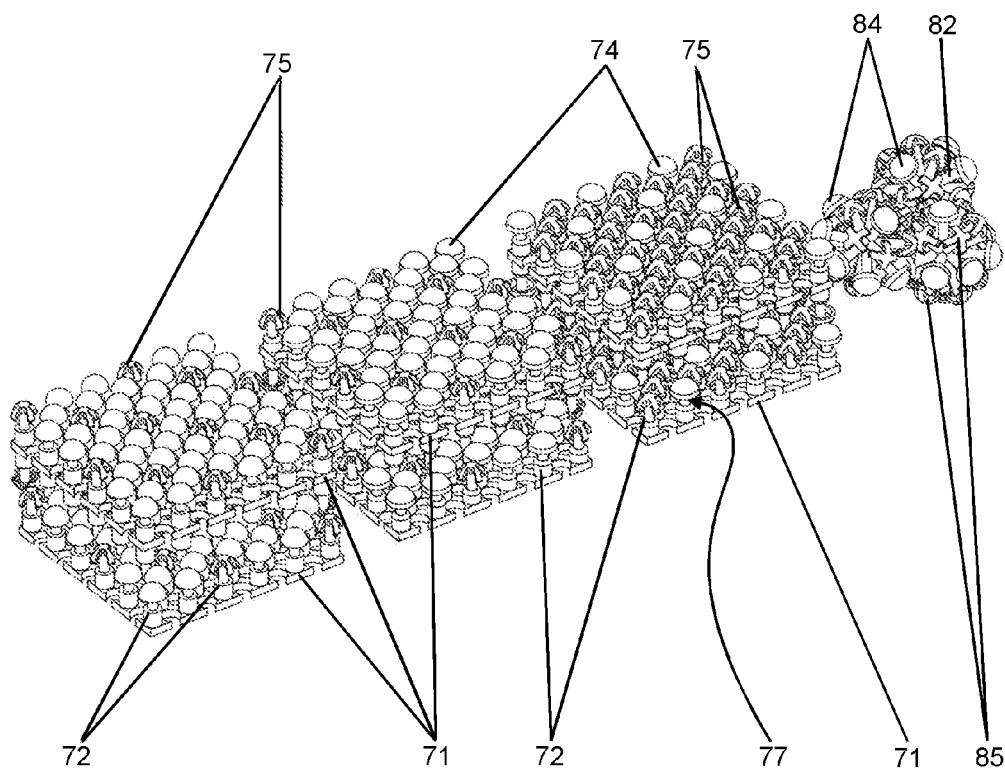
Figure 27:
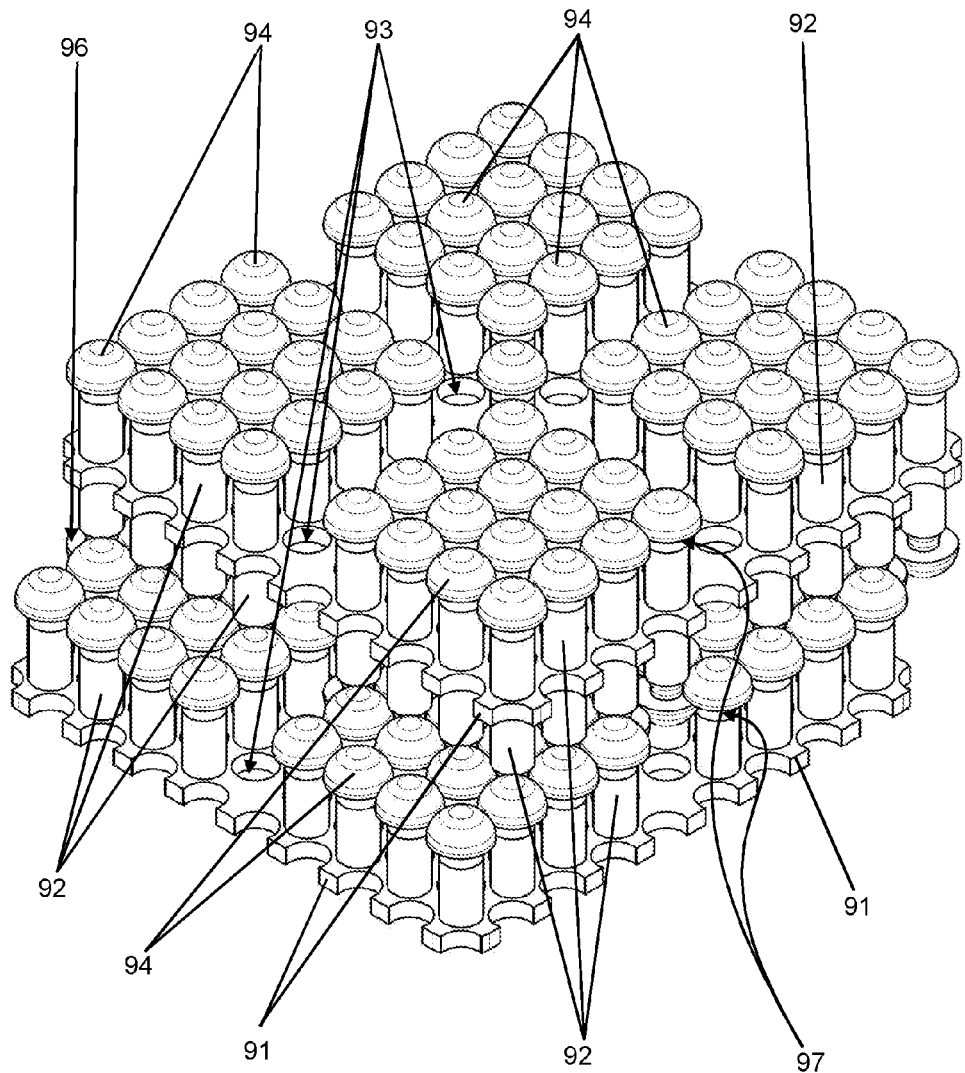
Figure 28:
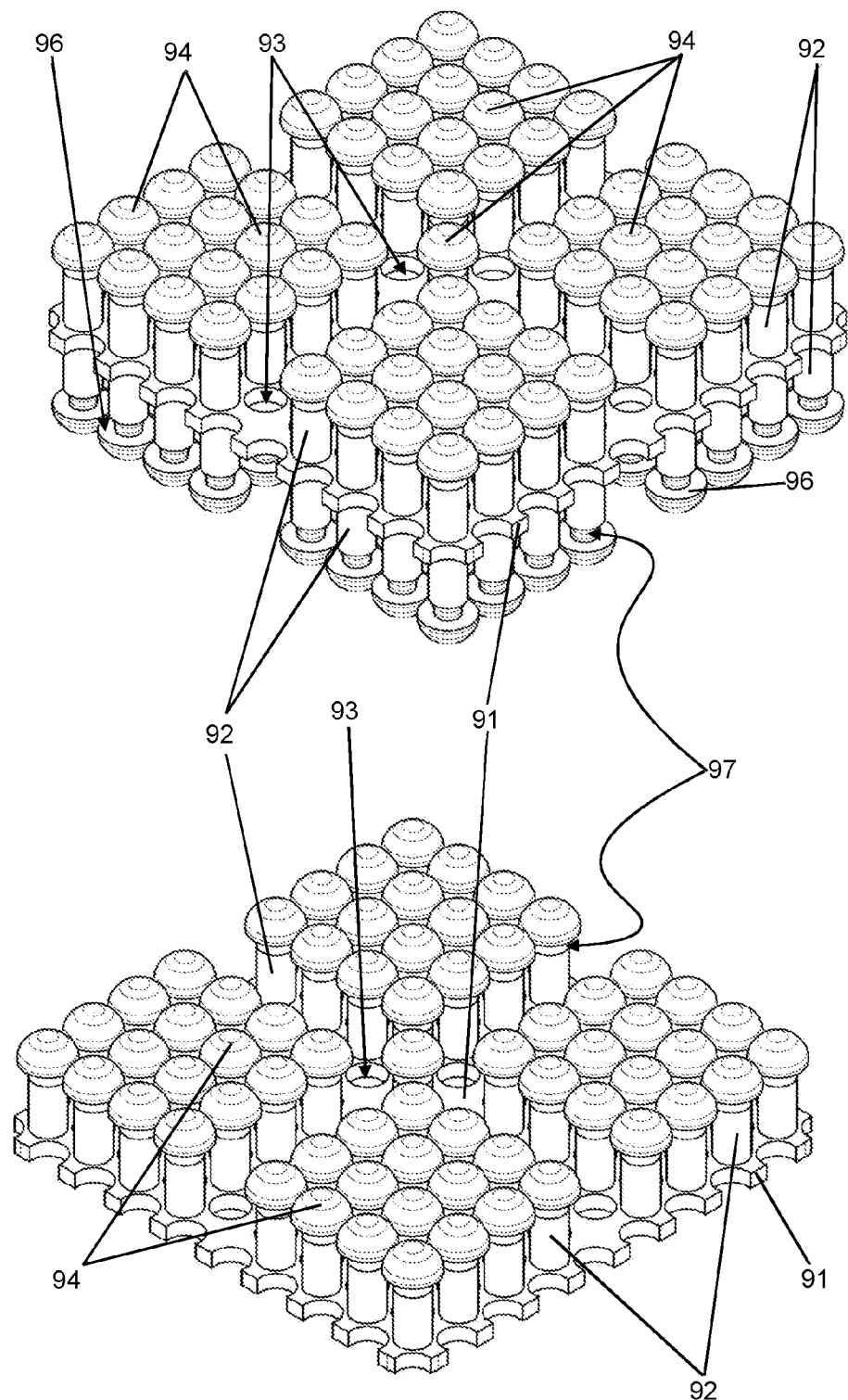
Figure 29:
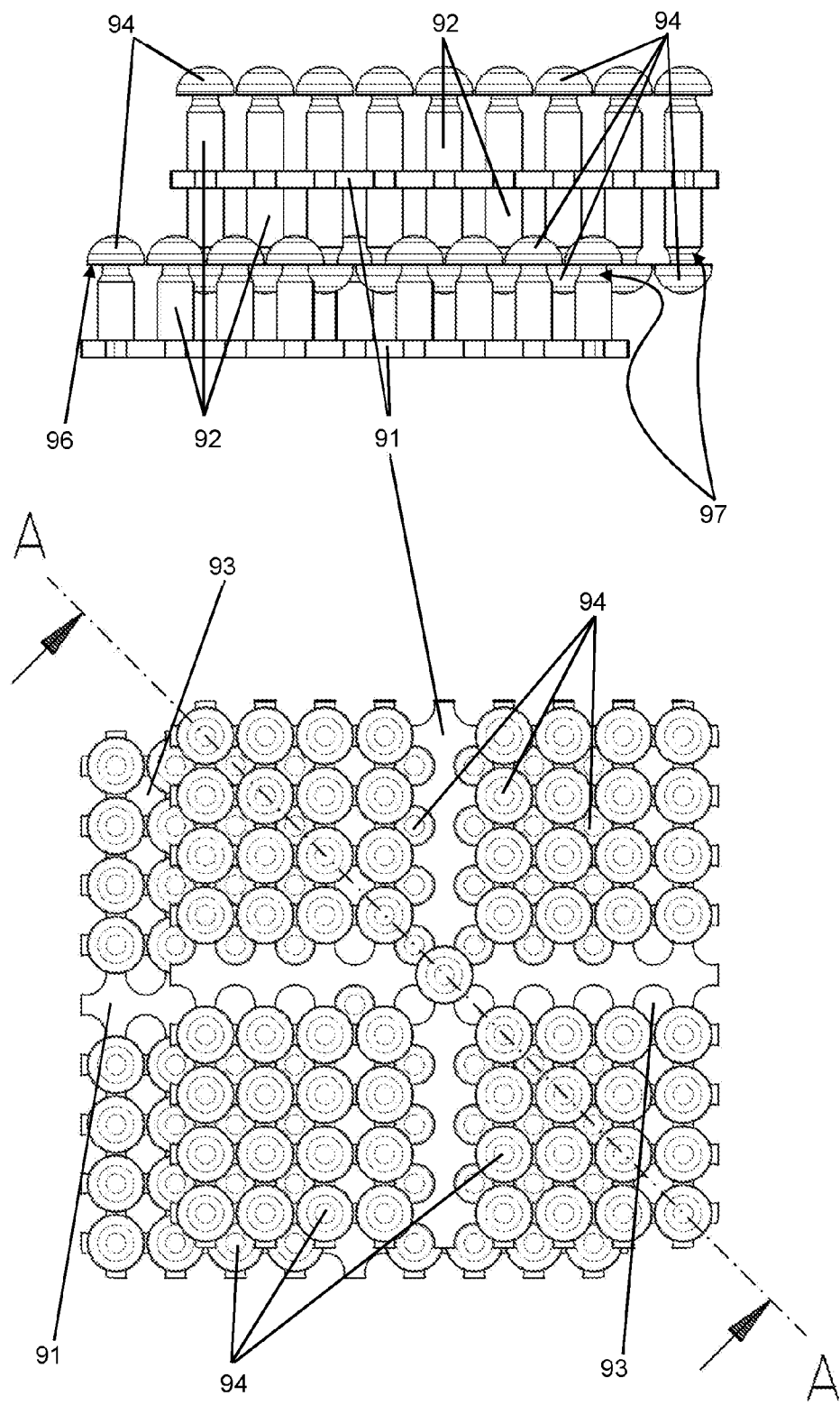
Figure 30:
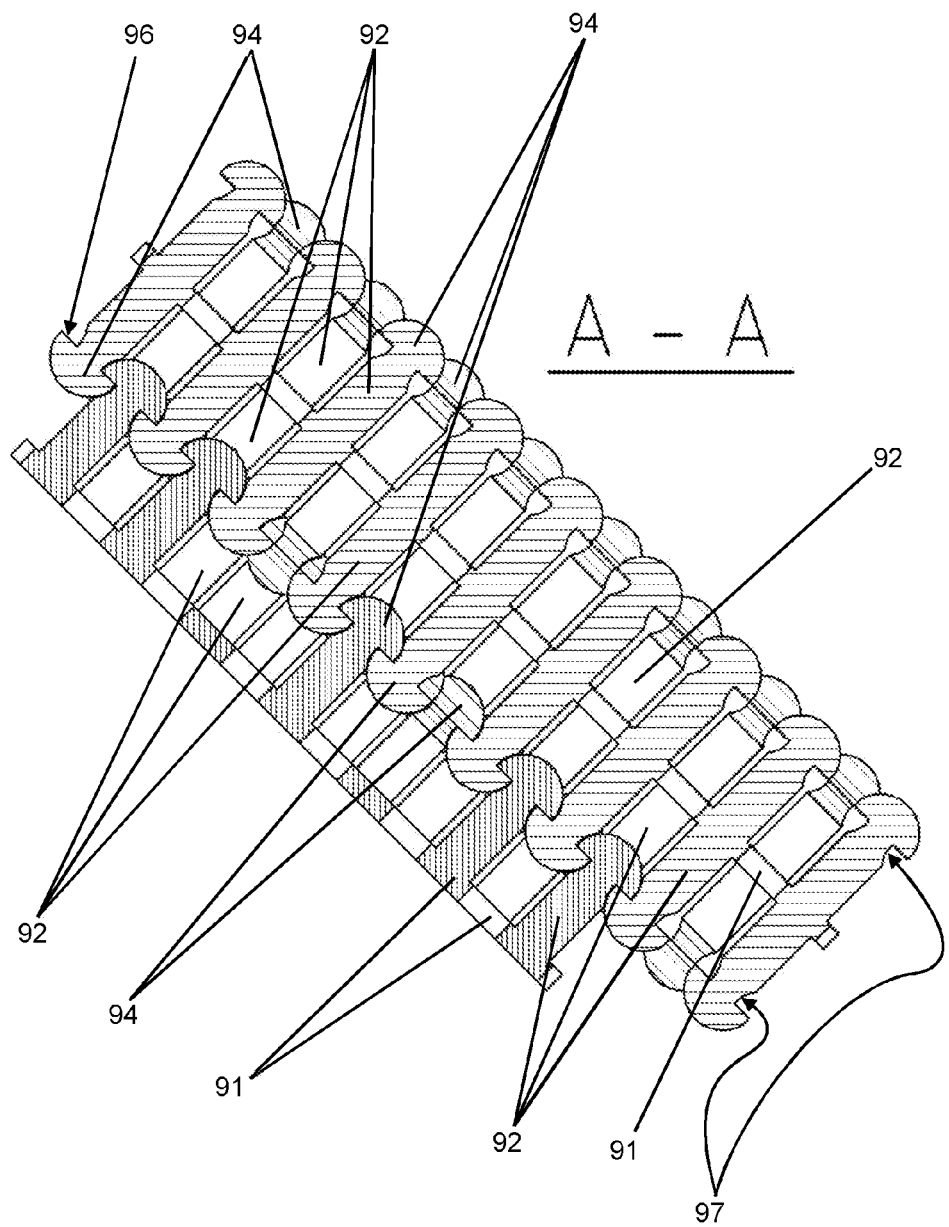
Figure 31:
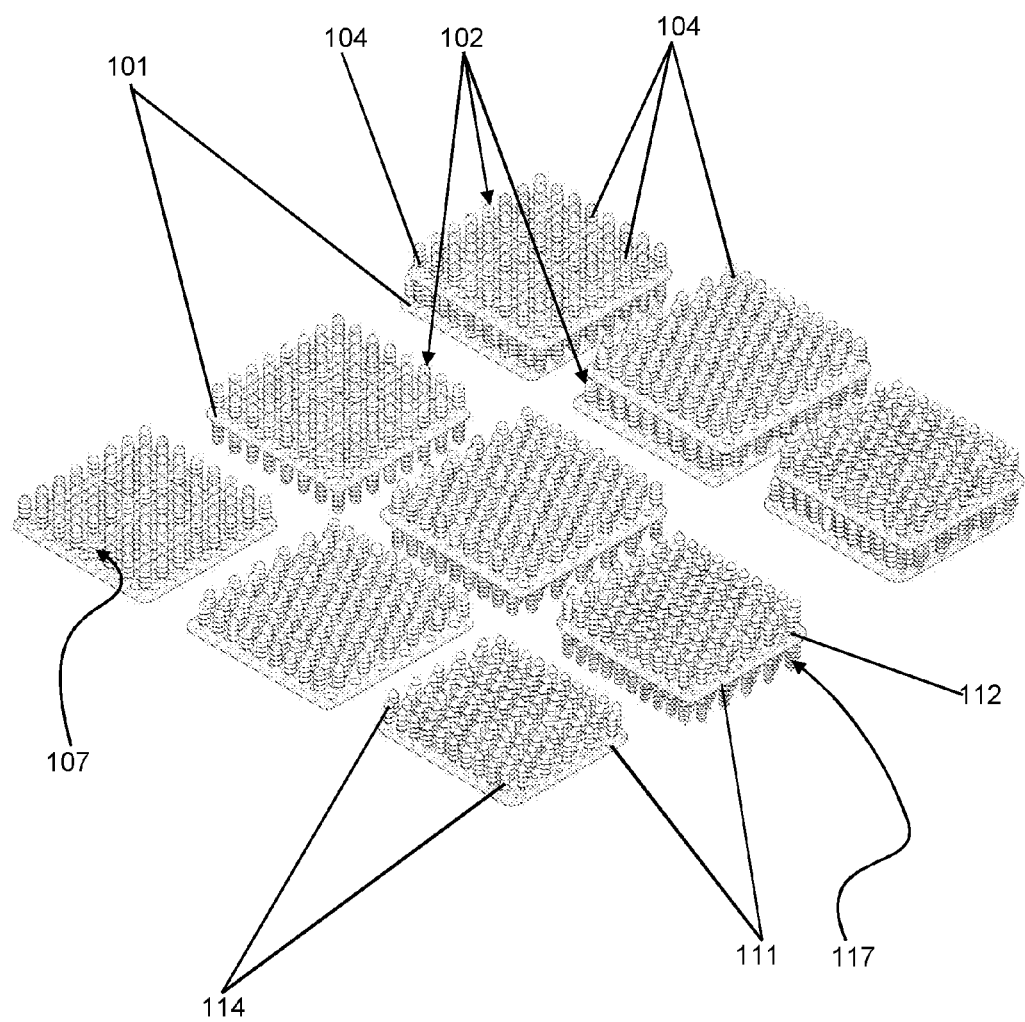
Figure 32:
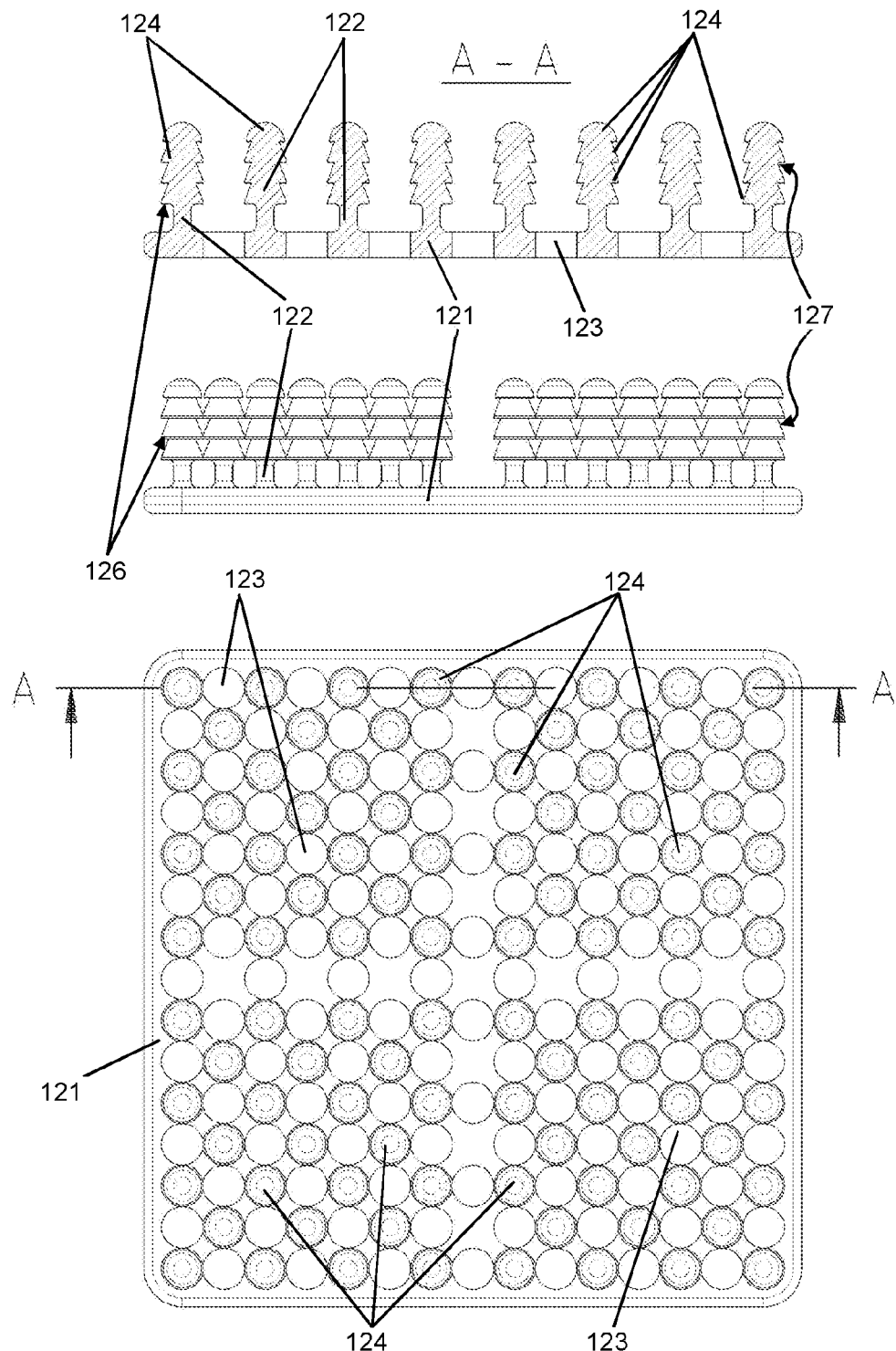
Figure 33:
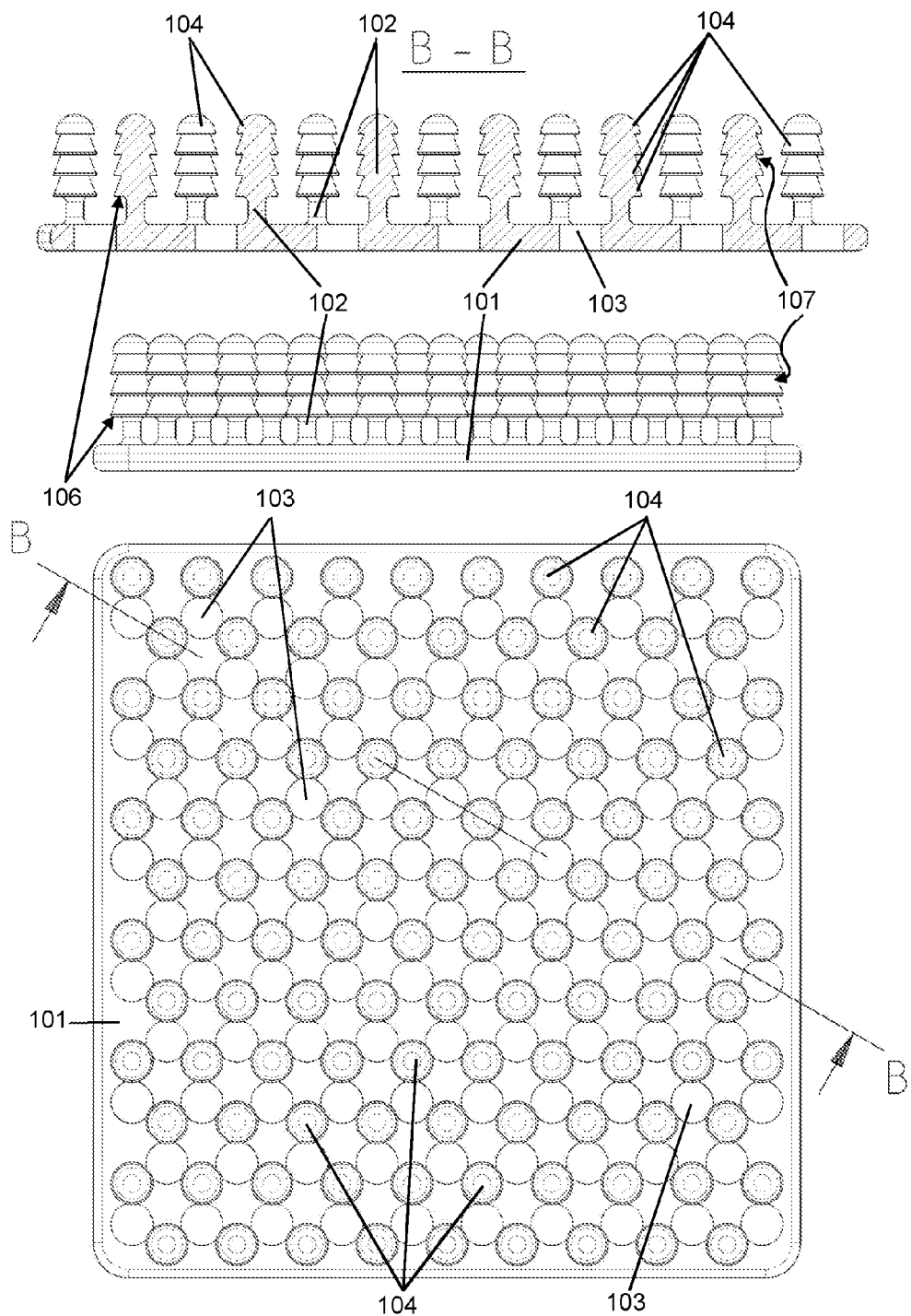
Figure 34:
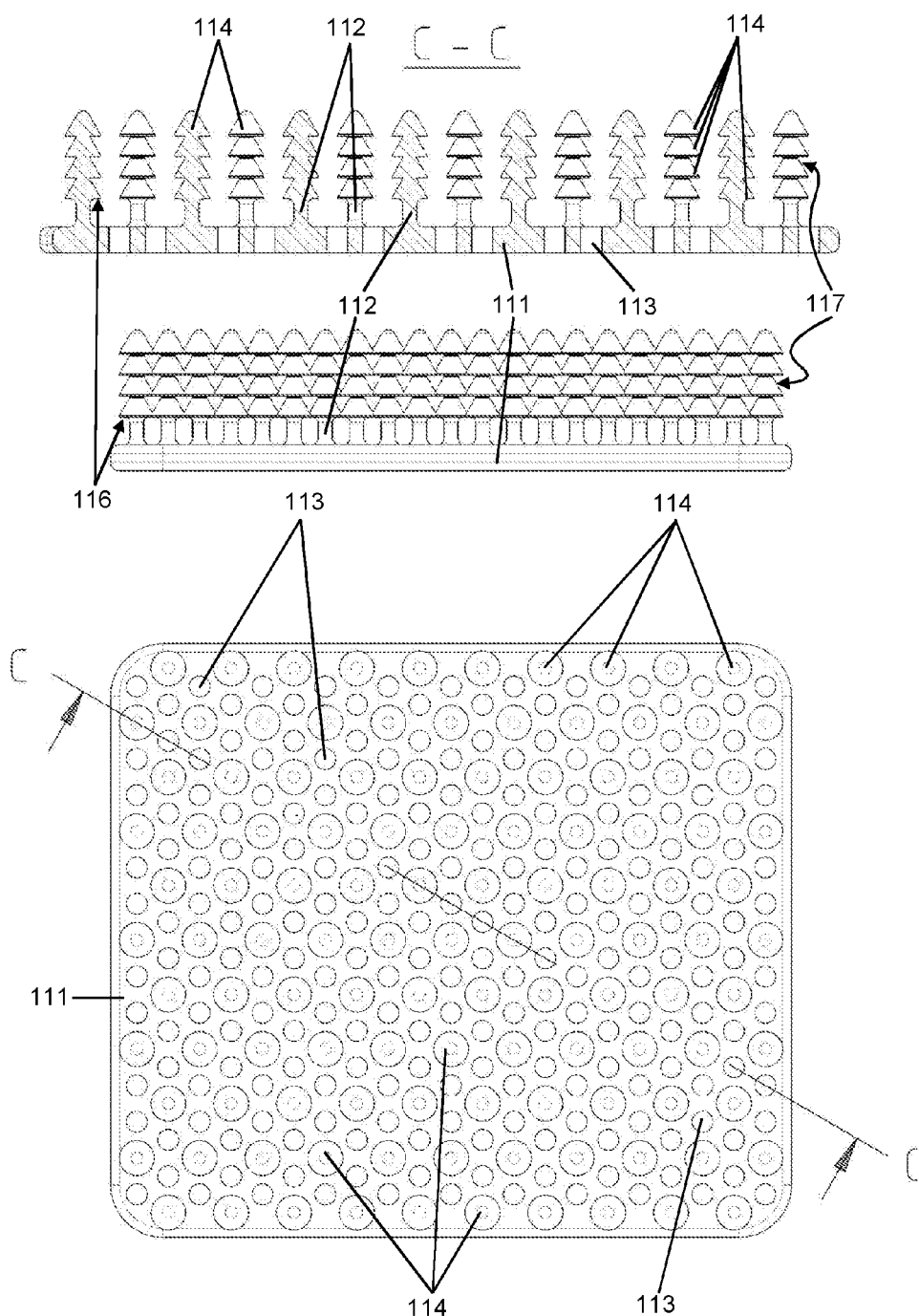
Figure 35:
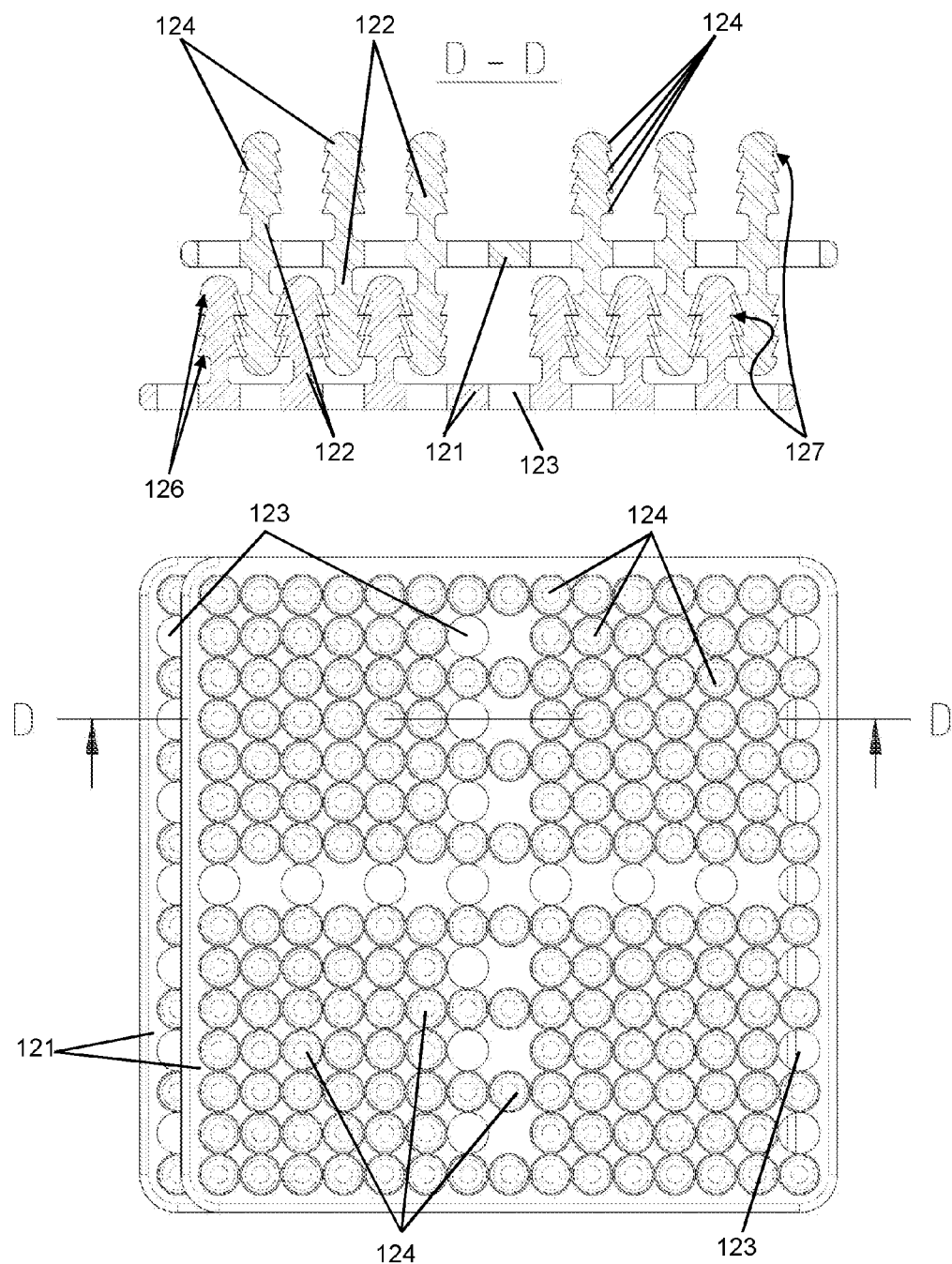
Figure 36:
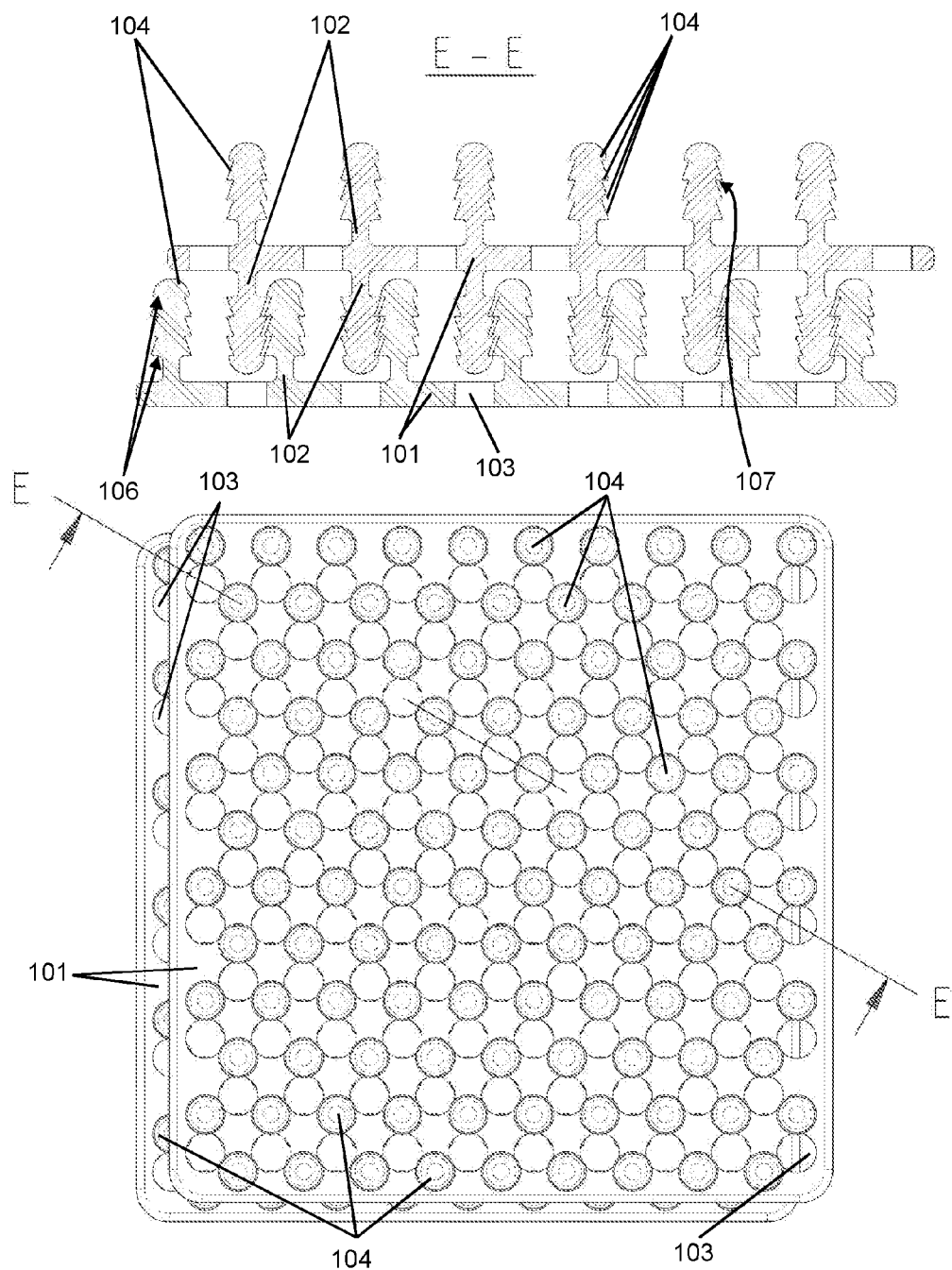
Figure 37:
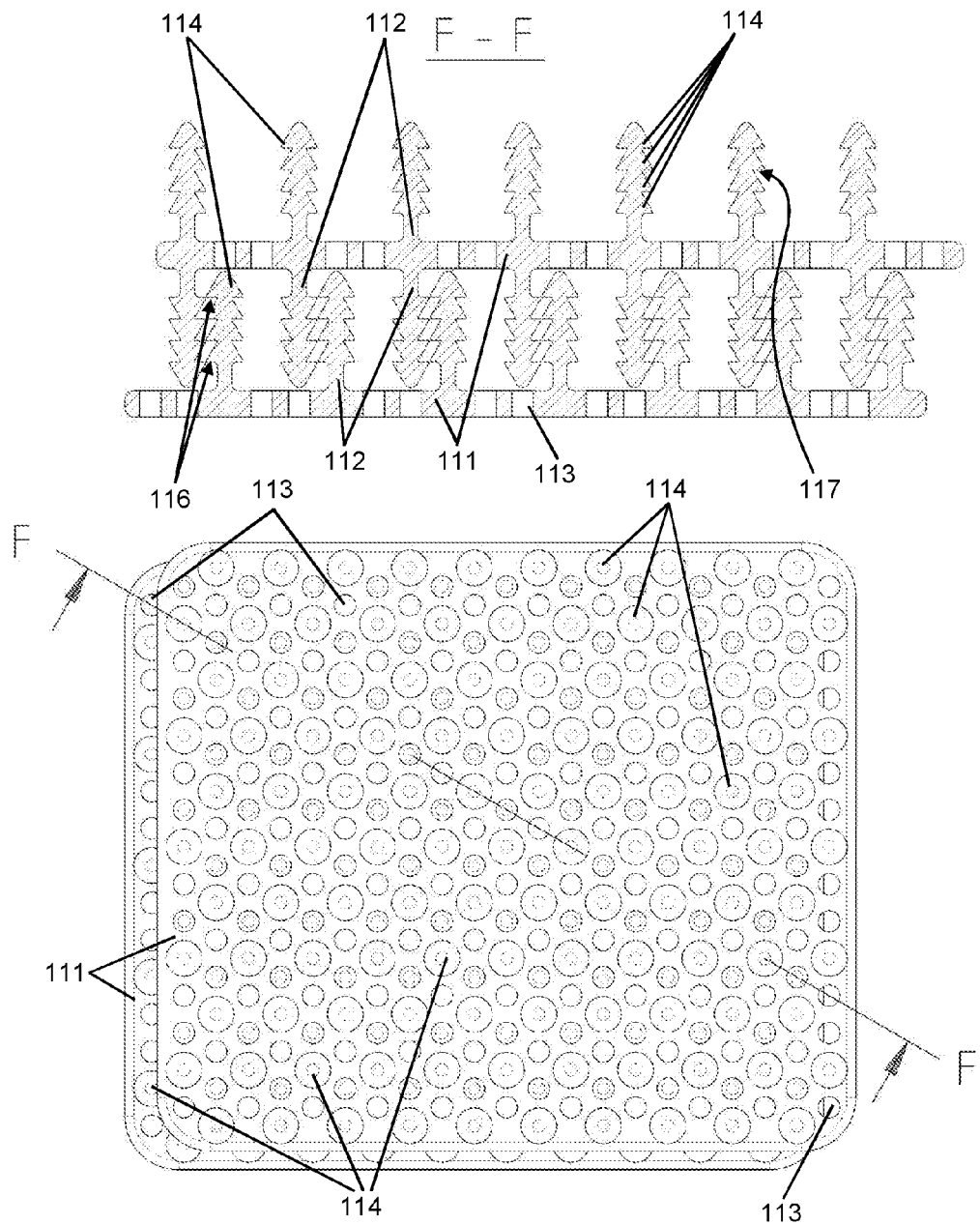

Further exemplary embodiments of the invention shall be illustrated in the following on the basis of thirty seven schematic figures, though without limiting the scope of the invention. In the figures:

FIG. 1: shows a schematic perspective view of five plates of a bone replacement material according to the invention that are partially connected to each other;

FIG. 2: shows five schematic views of the two lower plates according to FIG. 1, A) perspective view, B) side view, C) top view of the top side, D) view of the bottom side, E) cross-sectional view along the section A-A according to FIG. 2 B);

FIG. 3: shows three schematic views of the top three plates according to FIG. 1, A) perspective view, B) side view, C) top view of the top side;

FIG. 4: shows a schematic perspective view of three plates of the bone replacement material according to the invention according to FIGS. 1 to 3 that are interlocked with each other to different depths;

FIG. 5: shows a schematic side view of two plates of the bone replacement material according to the invention according to FIGS. 1 to 4 that are interlocked with each other by means of the connecting elements;

FIG. 6: shows a schematic side view of two plates of the bone replacement material according to the invention according to FIGS. 1 to 5 that are interlocked with each other by means of the connecting elements and by means of the planar structure;

FIG. 7: shows a schematic cross-sectional view of the two plates according to FIG. 6 that are interlocked with each other by means of the connecting elements and by means of the planar structure;

FIG. 8: shows four schematic views of plates of a second alternative bone replacement material that are connected to each other, A) perspective view, B) side view, C) top view of the top side, D) cross-sectional view along the section C-C according to FIG. 8 C);

FIG. 9: shows four schematic views of plates of a third alternative bone replacement material that are connected to each other, A) perspective view, B) side view, C) top view of the top side, D) cross-sectional view along the section B-B according to FIG. 9 C);

FIG. 10: shows three schematic views of two plates of a fourth alternative bone replacement material that are connected to each other, A) perspective view, B) top view of the top side, C) cross-sectional view along the section A-A according to FIG. 10 B);

FIG. 11: shows a schematic perspective view of two plates of the fourth bone replacement material according to the invention according to FIG. 10 that are connected to each other by means of the connecting elements;

FIG. 12: shows a schematic perspective view of two plates of the fourth bone replacement material according to the invention according to FIGS. 10 and 11 that are not connected to each other;

FIG. 13: shows four schematic views of the fourth alternative bone replacement material in an embodiment with defects, A) perspective view of two plates connected by means of the connecting elements, B) side view of a base plate, C) top view of the top side of the base plate according to FIG. 13 B), D) cross-sectional view along the section A-A according to FIG. 13 C);

FIG. 14: shows a schematic perspective view of two plates of a fifth bone replacement material according to the invention that are connected to each other by means of the connecting elements;

FIG. 15: shows three schematic views of the two plates of the fifth alternative bone replacement material according to FIG. 14 connected to each other, A) top view of the top side, B) side view, C) cross-sectional view along the section B-B according to FIG. 15 A);

FIG. 16: shows a schematic perspective view of two plates of a sixth bone replacement material according to the invention that are interlocked with each other by means of the connecting elements;

FIG. 17: shows a schematic perspective view of two plates of the sixth bone replacement material according to the invention according to FIG. 16 that are not interlocked with each other;

FIG. 18: shows a schematic side view of plates of the sixth bone replacement material according to the invention according to FIG. 16 that are interlocked with each other;

FIG. 19: shows a schematic perspective detailed view of two interlocked hooks (left), two non-interlocked hooks (right) of the sixth bone replacement material according to the invention according to FIGS. 16 to 18;

FIG. 20: shows a schematic perspective view of two plates of a seventh bone replacement material according to the invention that are not interlocked with each other;

FIG. 21: shows three schematic views of two plates of the seventh alternative bone replacement material that are connected to each other, A) top view of the top side, B) side view, C) cross-sectional view along the section B-B according to FIG. 21 A);

FIG. 22: shows a schematic perspective view of two plates of an eighth bone replacement material according to the invention that are not interlocked with each other;

FIG. 23: shows three schematic views of two plates of the eighth alternative bone replacement material that are connected to each other, A) top view of the top side, B) side view, C) cross-sectional view along the section C-C according to FIG. 23 A);

FIG. 24: shows a schematic perspective view of two plates of a modification of the eighth bone replacement material according to the invention that are not interlocked with each other;

FIG. 25: shows three schematic views of two plates of the modification of the eighth alternative bone replacement material that are connected to each other, A) top view of the top side, B) side view, C) cross-sectional view along the section C-C according to FIG. 23 A);

FIG. 26: shows a schematic perspective view of three and six pairwise mutually connected plates of the eighth alternative bone replacement material and of three particles of a bone replacement material, whereby the plates can be connected to the particles;

FIG. 27: shows a schematic perspective view of two plates of a ninth bone replacement material according to the invention that are snapped into each other;

FIG. 28: shows a schematic perspective view of two plates of the ninth bone replacement material according to the invention according to FIG. 27 that are not snapped into each other;

FIG. 29: shows two schematic views of the two plates of the ninth alternative bone replacement material according to FIG. 27 that are snapped into each other, in a top view of the top side (on the bottom in FIG. 29) and in a side view (on the top in FIG. 29);

FIG. 30: shows a schematic cross-sectional view of the section A-A according to FIG. 29, bottom, of the plates according to FIGS. 27 and 29 snapped into each other;

FIG. 31: shows a schematic perspective view of multiple plates of a tenth and eleventh bone replacement material according to the invention which are partly interlocked by its connecting elements;

FIG. 32: shows three schematic views of a plate of a twelfth alternative bone replacement material, bottom: top view of the top side, middle: side view, top: cross-sectional view along the section A-A according to FIG. 32 bottom;

FIG. 33: shows three schematic views of a plate of the tenth alternative bone replacement material, bottom: top view of the top side, middle: side view, top: cross-sectional view along the section B-B according to FIG. 33 bottom;

FIG. 34: shows three schematic views of a plate of the eleventh alternative bone replacement material, bottom: top view of the top side, middle: side view, top: cross-sectional view along the section C-C according to FIG. 34 bottom;

FIG. 35: shows two schematic views of two plates of the twelfth alternative bone replacement material according to FIG. 32 that are connected to each other, bottom: top view of the top side, top: cross-sectional view along the section D-D according to FIG. 35 bottom;

FIG. 36: shows two schematic views of two plates of the tenth alternative bone replacement material according to FIG. 33 that are connected to each other, bottom: top view of the top side, top: cross-sectional view along the section E-E according to FIG. 36 bottom; and FIG. 37: shows two schematic views of two plates of the eleventh alternative bone replacement material according to FIG. 34 that are connected to each other, bottom: top view of the top side, top: cross-sectional view along the section F-F according to FIG. 37 bottom.

FIGS. 1 to 7 show a first embodiment of the present invention, with FIG. 1 showing a schematic perspective view of five plates of a bone replacement material according to the invention that are partially connected to each other to form an open-pored body and/or solid, and FIG. 2 showing five schematic views of the two lower plates (base plates) according to FIG. 1, as A) perspective view, B) side view, C) top view of the top side, D) view of the bottom side, and E) cross-sectional view along the section A-A according to FIG. 2 B). Moreover, FIG. 3 shows three schematic views of the top three plates (build-up plates) according to FIG. 1, as A) perspective view, B) side view, and C) top view of the top side. FIG. 4 shows a schematic perspective view of three plates of the bone replacement material according to the invention that are interlocked with each other to different depths for formation of an open-pored three-dimensional body according to FIGS. 1 to 3.

The plates consist of an elastic biocompatible plastic material or of stainless steel, titanium, a titanium alloy, tantalum, a tantalum alloy, but can also be fabricated from composites of said materials. The plates are manufactured by a CAM procedure (CAM—computer-aided manufacturing) and/or a 3D printing procedure, for example by selective laser melting SLM (selective laser melting). Other rapid prototyping methods and/or computer-aided generative production methods can also be used for producing the plates, such as, for example, Fused Layer Modeling/Manufacturing (FLM), Fused Deposition Modeling (FDM), Laminated Object Modelling (LOM) of plastic films, Layer Laminated Manufacturing (LLM) of plastic films, Electron Beam Melting (EBM) of plastic materials or metals, Multi Jet Modeling (MJM) of plastic materials, Selective Laser Sintering (SLS) of plastic materials or metals, Stereolithography (STL or SLA) of plastic materials, polishing or multi-axes milling procedures or Digital Light Processing (DLP) of photopolymerising liquid plastic materials.

The plates each comprise a plate-shaped planar structure 1 that bears the entire plates and connects them in itself. The planar structure 1 is flexible and can be deformed elastically such that surfaces other than planes can be formed with the planar structure 1. A multitude of pins 2 extend away from the planar structure 1 of each plate, projecting perpendicularly away from the plane of the planar structure 1. A multitude of through-going recesses 3 are arranged between the pins 2 in the planar structure 1, which cause the three-dimensional body to possess an open porosity in a direction perpendicular to the planar structures 1 when the plates are connected to each other to form a solid.

FIGS. 1 to 7 show two different types of plates, namely, firstly, base plates that comprise a flat bottom side and in which the pins 2 extend from the planar structure 1 only on one side of the planar structures 1, and, secondly, build-up plates, in which the pins 2 extend from both sides of the planar structure 1. The base plates are shown on the bottom in FIG. 1, in FIG. 2, on the bottom in FIG. 4, and on the bottom in FIG. 5. The build-up plates are shown on the top in FIG. 1, in FIG. 3, on the top in FIG. 4, on the top in FIG. 5, and in FIGS. 6 and 7. The base plates can be attached to the bone to be treated such that large surface areas touch against it. However, the build-up plates can also be attached to the bone to be treated, although with a lesser contact surface, such that the base plates, theoretically, can be omitted.

The pins 2, otherwise being cylindrical, have mushrooms 4 as connecting elements 4 provided on the ends of the pins 2 opposite from the planar structures 1. The mushrooms 4 are rounded towards the outside (away from the planar structure 1) and form spherical segments. However, other types of rounding, such as, for example, ellipsoidal segments, are feasible just as well. On the side oriented towards the planar structure 1, the mushrooms 4 form a planar gripping surface 6 that is suitable for interlocking with other mushrooms 4 of engaging plates or with the recesses 3 of engaging plates.

In this context, FIG. 5 shows a schematic side view of two plates of the bone replacement material according to the invention that are interlocked with each other just by means of the mushrooms 4, FIG. 6 shows a schematic side view of two plates of the bone replacement material according to the invention that are snapped into each other by means of the mushrooms 4 and by means of the recesses 3 of the planar structure 1, and FIG. 7 shows a schematic cross-sectional view of the two plates shown in FIG. 6 that are snapped into each other by means of the mushrooms 4 and by means of the recesses 3 of the planar structure 1.

In order to form a bone replacement material according to the invention, the plates preferably are situated to touch against each other, without being interlocked with or snapped into each other, such that the mushrooms 4 of the pins 2 of neighbouring plates do not engage each other yet. Moreover, the plates can be present in a condition wetted by a liquid. The liquid preferably contains at least one pharmaceutically active substance suitable for controlling an infection or for stimulating bone growth. Alternatively or in addition, the plates can be coated with a pharmaceutically active substance of this type.

The bone replacement material can be formed by pushing the plates into each other by means of their surfaces. By this means, the plates interlock with or snap into each other and the bone replacement material becomes reinforced as desired. Earlier, the plates can also be deformed and adapted to the treatment scenario through elastic deformation of the planar structure 1. After interlocking with or snapping into at least one further plate (which usually is also deformed), the two plates, thus connected to each other, stabilise each other to the effect that the selected shape is reinforced.

In this context, the plates become connected to each other in appropriate manner such that free gaps between the plates that are connected to each other remain in the regions of the pins 2 and the mushrooms 4 such that the three-dimensional body formed from the plates is open-pored in the directions parallel to the plane of the plates as well. The plates have a cross-section and/or a thickness of approximately 5 mm such that the remaining pores have a free cross-section in the range of approximately 0.5 mm. Said cross-section is sufficient to allow bone material to be formed in and/or to grow into the pores. The three-dimensional body with its open pores can therefore be called osteoconductive. The three-dimensional body formed from the plates is therefore well-suited as bone replacement material.

The plates should be pushed firmly into each other such that the three-dimensional body is dimensionally stable. In this context, the plates can interlock with each other in a first stage by the mushrooms 4 elastically deforming the pins 2 of connected plates and by the mushrooms 4 limiting the motion of neighbouring plates away from the planar structure 1 due to the elastic restoring force of the pins 2 (see FIG. 5). When the plates are pushed further into each other, the plates can snap into each other in a second stage by the mushrooms 4 being pushed through the recesses 3 of the planar structure 1. In this context, the mushrooms 4 can get lodged in the recesses 3 which prevents the mushrooms 4 from moving with respect to the neighbouring plate and thus snaps the two plates into each other. It is feasible just as well that, firstly, the edges of the mushrooms 4 plastically deform the pins 2 or the recesses 3 or the mushrooms 4 to a small extent or, secondly, that the edges of the recesses 3 plastically deform the mushrooms 4 of neighbouring plates to a small extent and that the plates are thus snapped into each other. Moreover, two plates can be connected to each other through interlocking the plates in some areas by means of the mushrooms 4 and by snapping them into each other in other areas by means of the mushrooms 4 and recesses 3. Preferably, the dimensions of the mushrooms 4, the depth of the recesses 3 (and/or the thickness of the planar structure 1), and the length of the pins 2 between the planar structure 1 and the mushrooms 4 are adapted to each other appropriately such that, upon interlocking of the plates, the surfaces of the mushrooms 4 facing away from the planar structure 1 touch against the surface of the planar structure 1 of neighbouring plates and, upon snapping the plates to each other, the surfaces of the mushrooms 4 facing away from the planar structure 1 touch against the gripping surface 6 of the mushrooms 4 of the neighbouring plate. As a result, the plates are not mobile with respect to each other without deformation when they are interlocked or when they are snapped-in.

In order to ensure that the gripping surfaces 6 or the opposite cap top sides of the mushrooms 4 do not close the recesses 3 completely and to thus ensure that the recesses 3 can be deformed more easily by the mushrooms 4, the recesses 6 each comprise six slits that are distributed over the circumference of the recesses 3. The width of the slits should be sufficient to allow them to have an osteoconductive effect.

FIG. 8 shows four schematic views of plates of a second alternative bone replacement material that are connected to each other, in A) a perspective view, B) a side view, C) a top view of the top side, and D) a cross-sectional view along the section C-C according to FIG. 8 C).

The plates consist of stainless steel, titanium, a titanium alloy, tantalum, a tantalum alloy or can be fabricated from an elastic biocompatible plastic material or a composite of the metallic materials. The plates are produced through a CAM procedure and/or a 3D printing procedure, for example through selective electron beam melting (EBM). Other rapid prototyping methods and/or computer-aided generative production methods can also be used for producing the plates.

The plates each comprise a plate-shaped planar structure 11 that bears the entire plates and connects them in itself. The planar structure 11 is flexible and can be deformed elastically such that surfaces other than planes can be formed with the planar structure 11. A multitude of pins 12 extend away from the planar structure 11 of each plate, projecting perpendicularly away from the plane of the planar structure 11. A multitude of through-going recesses 13 are arranged between the pins 12 in the planar structure 11, which can cause the three-dimensional body to possess an open porosity in a direction perpendicular to the planar structures 11 when the plates are connected to each other to form a three-dimensional body and when the neighbouring plates do not touch and thus cover the recesses 13.

FIG. 8 shows only one of the two types of plates, namely build-up plates, in which the pins 12 extend away from both sides of the planar structure 11. Base plates may be provided just as well, in which a flat bottom side is provided and in which the pins 12 extend away from the planar structure 11 only on one side of the planar structure 11. Said base plates can be attached to the bone to be treated such that large surface areas touch against it. However, the build-up plates shown can also be attached to the bone to be treated, although with a lesser contact surface, such that the base plates can be omitted.

The pins 12, otherwise being cylindrical, have mushrooms 14 as connecting elements 14 provided on the ends of the pins 12 opposite from the planar structures 11 and in the middle between the ends of the pins 12 and the planar structures 11. The mushrooms 14 are rounded towards the outside (away from the planar structure 11) and form spherical segments. However, other types of rounding, such as, for example, ellipsoidal segments, are feasible just as well. On the side oriented towards the planar structure 11, the mushrooms 14 form a planar gripping surface 16 that is suitable for interlocking with other mushrooms 14 of engaging plates or with the recesses 13 of engaging plates.

In order to form a bone replacement material according to the invention, the plates preferably are situated to touch against each other, without being interlocked with or snapped into each other (i.e. unlike what is shown in FIG. 8), such that the mushrooms 14 of the pins 12 of neighbouring plates do not engage each other yet. Moreover, the plates can be present in a condition wetted by a liquid. The liquid preferably contains at least one pharmaceutically active substance suitable for controlling an infection or for stimulating bone growth. Alternatively or in addition, the plates can be coated with a pharmaceutically active substance of this type.

The bone replacement material can be formed by pushing the plates into each other by means of their surfaces. By this means, the plates interlock with or snap into each other and the bone replacement material becomes reinforced as desired. Earlier, the plates can also be deformed and adapted to the treatment scenario through elastic deformation of the planar structure 11. After interlocking with or snapping into at least one further plate (which usually is also deformed), the two plates, thus connected to each other, stabilise each other to the effect that the selected shape is reinforced.

In this context, the plates become connected to each other in appropriate manner such that free gaps between the mutually connected plates remain in the regions of the pins 12 and the mushrooms 14 such that the three-dimensional body formed from the plates is open-pored in the directions parallel to the plane of the plates. The plates have a cross-section and/or a thickness of approximately 9 mm such that the remaining pores have a free cross-section in the range of approximately 0.5 mm. Said cross-section is sufficient to allow bone material to be formed in and/or to grow into the pores. The three-dimensional body with its open pores can therefore be called osteoconductive. The three-dimensional body formed from the plates is therefore well-suited as bone replacement material.

The plates should be pushed firmly into each other such that the three-dimensional body is dimensionally stable. In this context, the plates can interlock with each other in a first stage by the mushrooms 14 elastically deforming the pins 12 of connected plates and by the mushrooms 14 limiting the motion of neighbouring plates away from the planar structure 11 due to the elastic restoring force of the pins 12. When the plates are pushed further into each other, the plates can snap into each other in a second stage by the outer mushrooms 14 being pushed through the recesses 13 of the planar structures 11, as shown in FIG. 8. In this context, the outer mushrooms 14 can get lodged in the recesses 13 which prevent the mushrooms 14 from moving with respect to the neighbouring plate and thus snap the two plates into each other. It is feasible just as well that, firstly, the edges of the mushrooms 14 plastically deform the pins 12 or the recesses 13 or the mushrooms 14 to a small extent or, secondly, that the edges of the recesses 13 plastically deform the mushrooms 14 of neighbouring plates to a small extent and that the plates are thus snapped into each other. A first interlocking proceeds already when the outer mushrooms 14 of neighbouring plates engage each other. Moreover, two plates can be connected to each other through interlocking the plates in some areas by means of the mushrooms 14 and by snapping them into each other in other areas by means of the mushrooms 14 and recesses 13. Preferably, the dimensions of the mushrooms 14, the depth of the recesses 13 (and/or the thickness of the planar structure 11), and the length of the pins 12 between the planar structure 11 and the mushrooms 14 and between the inner and outer mushrooms 14 are adapted to each other appropriately such that, upon interlocking of the plates, the surfaces of the mushrooms 14 facing away from the planar structure 11 touch against the surface of the planar structure 11 of neighbouring plates and/or, upon connecting the plates, the surfaces of the mushrooms 14 facing away from the planar structure 11 touch against the gripping surface 16 of the mushrooms 14 of the neighbouring plate. As a result, the connected plates cannot move with respect to each other without deformation.

In order to ensure that the gripping surfaces 16 or the opposite cap top sides of the mushrooms 14 do not close the recesses 13 completely and to thus ensure that the recesses 13 can be deformed more easily by the mushrooms 14, the recesses 13 each may comprise multiple slits (not shown) that are distributed over the circumference of the recesses 13. The width of the slits should be sufficient to allow them to have an osteoconductive effect.

Accordingly, the embodiment according to FIG. 8 differs from the one according to FIGS. 1 to 7 mainly in that the pins 12 comprise two mushrooms 14 that are arranged at a distance with respect to each other. Moreover, the recesses 13 comprise no additional slits.

FIG. 9 shows four schematic views of plates of a third alternative bone replacement material that are connected to each other. In this context, FIG. 9 A) shows a perspective view, FIG. 9 B) shows a side view, FIG. 9 C) shows a top view of the top side, and FIG. 9 D) shows a cross-sectional view along the section B-B according to FIG. 9 C).

The plates consist of titanium or a titanium alloy, tantalum or a tantalum alloy or can be fabricated from stainless steel, an elastic biocompatible plastic material or a composite of said materials. The plates are produced through a CAM procedure and/or a 3D printing procedure, for example through selective electron beam melting (EBM). Other rapid prototyping methods and/or computer-aided generative production methods can also be used for producing the plates.

The plates each comprise a plate-shaped planar structure 21 that bears the entire plates and connects them in itself. The planar structure 21 is flexible and can be deformed elastically such that surfaces other than planes can be formed with the planar structure 21. A multitude of pins 22 extend away from the planar structure 21 of each plate, projecting perpendicularly away from the plane of the planar structure 21. A multitude of through-going recesses 23 are arranged between the pins 22 in the planar structure 21, which can cause the three-dimensional body to possess an open porosity in a direction perpendicular to the planar structures 21 when the plates are connected to each other to form a three-dimensional body and when the neighbouring plates do not touch and thus cover the recesses 23.

FIG. 9 shows only one of the two types of plates, namely build-up plates, in which the pins 22 extend away from both sides of the planar structure 21. Base plates may be provided just as well, in which a flat bottom side is provided and in which the pins 22 extend away from the planar structure 21 only on one side of the planar structure 21. Said base plates can be attached to the bone to be treated such that large surface areas touch against it. However, the build-up plates shown can also be attached to the bone to be treated, although with a lesser contact surface, such that the base plates can be omitted.

The pins 22, otherwise being cylindrical, have mushrooms 24 as connecting elements 24 provided on the ends of the pins 22 opposite from the planar structures 21. The mushrooms 24 are rounded towards the outside (away from the planar structure 21) and form spherical segments. However, other types of rounding, such as, for example, ellipsoidal segments, are feasible just as well. On the side oriented towards the planar structure 21, the mushrooms 24 form a planar gripping surface 26 that is suitable for interlocking with or snap-in connection to other mushrooms 24 of engaging plates or with the recesses 23 of engaging plates.

In order to form a bone replacement material according to the invention, the plates preferably are situated to touch against each other, without being interlocked with or snapped into each other (i.e. unlike what is shown in FIG. 9), such that the mushrooms 24 of the pins 22 of neighbouring plates do not engage each other yet. Moreover, the plates can be present in a condition wetted by a liquid. The liquid preferably contains at least one pharmaceutically active substance suitable for controlling an infection or for stimulating bone growth. Alternatively or in addition, the plates can be coated with a pharmaceutically active substance of this type.

The bone replacement material can be formed by pushing the plates into each other by means of their surfaces. By this means, the plates interlock with or snap into each other and the bone replacement material becomes reinforced as desired. Earlier, the plates can also be deformed and adapted to the treatment scenario through elastic deformation of the planar structure 21. After interlocking with or snapping into at least one further plate (which usually is also deformed), the two plates, thus connected to each other, stabilise each other to the effect that the selected shape is reinforced.

In this context, the plates become connected to each other in appropriate manner such that free gaps between the mutually connected plates remain in the regions of the pins 22 and the mushrooms 24 such that the three-dimensional body formed from the plates is open-pored in the directions parallel to the plane of the plates. The plates have a cross-section and/or a thickness of approximately 3 mm such that the remaining pores have a free cross-section in the range of approximately 0.3 mm. Said cross-section is sufficient to allow bone material to be formed in and/or to grow into the pores. The three-dimensional body with its open pores can therefore be called osteoconductive. The three-dimensional body formed from the plates is therefore well-suited as bone replacement material.

The plates should be pushed firmly into each other such that the three-dimensional body is dimensionally stable. In this context, the plates can interlock with each other in a first stage by the mushrooms 24 elastically deforming the pins 22 of connected plates and by the mushrooms 24 limiting the motion of neighbouring plates away from the planar structure 21 due to the elastic restoring force of the pins 22. When the plates are pushed further into each other, the plates can interlock with or snap into each other in a second stage by the mushrooms 24 being pushed through the recesses 23 of the planar structures 21, as shown in FIG. 9. In this context, the mushrooms 24 can get lodged in the recesses 23 which prevents the mushrooms 24 from moving with respect to the neighbouring plate and thus snaps the two plates into each other. It is feasible just as well that, firstly, the edges of the mushrooms 24 plastically deform the pins 22 or the recesses 23 or the mushrooms 24 to a small extent or, secondly, that the edges of the recesses 23 plastically deform the mushrooms 24 of neighbouring plates to a small extent and that the plates are thus snapped into each other.

Moreover, two plates can be connected to each other through interlocking the plates in some areas by means of the mushrooms 24 and by snapping them into each other in other areas by means of the mushrooms 24 and recesses 23. Preferably, the dimensions of the mushrooms 24, the depth of the recesses 23 (and/or the thickness of the planar structure 21), and the length of the pins 22 between the planar structure 21 and the mushrooms 24 are adapted to each other appropriately such that, upon connection of the plates, the surfaces of the mushrooms 24 facing away from the planar structure 21 touch against the surface of the planar structure 21 of neighbouring plates and, upon connection of the plates, the surfaces of the mushrooms 24 facing away from the planar structure 21 touch against the gripping surface 26 of the mushrooms 24 of the neighbouring plate. As a result, the connected plates cannot move with respect to each other without deformation.

In order to ensure that the gripping surfaces 26 or the opposite cap top sides of the mushrooms 24 do not close the recesses 23 completely and to thus ensure that the recesses 23 can be deformed more easily by the mushrooms 24, the recesses 23 may each comprise multiple slits (not shown) that are distributed over the circumference of the recesses 23. The width of the slits should be sufficient to allow them to have an osteoconductive effect.

Accordingly, the embodiment according to FIG. 9 differs from the one according to FIGS. 1 to 7 mainly in that the pins 22 and the recesses 23 are situated at a somewhat larger distance with respect to each other. Moreover, the recesses 23 comprise no additional slits.

FIG. 10 shows three schematic views of two plates of a fourth alternative bone replacement material that are connected to each other, A) perspective view, B) top view of the top side, C) cross-sectional view along the section A-A according to FIG. 10 B), and FIGS. 11 to 13 show further variants of the fourth alternative bone replacement material.

The plates consist of a biocompatible metal, such as stainless steel, titanium or a titanium alloy, tantalum or a tantalum alloy or can be fabricated from an elastic biocompatible plastic material or a composite of said materials. The plates are produced through a CAM procedure and/or a 3D printing procedure, for example through selective electron beam melting (EBM). Other rapid prototyping methods and/or computer-aided generative production methods can also be used for producing the plates.

The plates each comprise a plate-shaped planar structure 31 that bears the entire plates and connects them in itself. The planar structure 31 is flexible and can be deformed elastically such that surfaces other than planes can be formed with the planar structure 31. A multitude of pins 32 extend away from the planar structure 31 of each plate, projecting perpendicularly away from the plane of the planar structure 31. A multitude of through-going recesses 33 are arranged between the pins 32 in the planar structure 31, which can cause the three-dimensional body to possess an open porosity in a direction perpendicular to the planar structures 31 when the plates are connected to each other to form a three-dimensional body and when the neighbouring plates do not touch and thus cover the recesses 33.

FIGS. 10 to 13 show two different types of plates, namely, firstly, base plates that comprise a flat bottom side and in which the pins 32 extend from the planar structure 31 only on one side of the planar structures 31, and, secondly, build-up plates, in which the pins 32 extend from both sides of the planar structure 31. The base plates are shown on the bottom in FIG. 10 and/or below it, on the bottom in FIG. 11, on the top in FIG. 12, and on the bottom in FIG. 13A) and in FIGS. 13 B) to D). The build-up plates are shown on the top in FIG. 10, on the top in FIG. 11, on the bottom in FIG. 12, and on the top in FIG. 13 A). The base plates can be attached to the bone to be treated such that large surface areas touch against it. However, the build-up plates can also be attached to the bone to be treated, although with a lesser contact surface, such that the base plates can be omitted.

The pins 32, otherwise being cylindrical, have mushrooms 34 as connecting elements 34 provided on the ends of the pins 32 opposite from the planar structures 31. The mushrooms 34 are rounded towards the outside (away from the planar structure 31) and form spherical segments. However, other types of rounding, such as, for example, ellipsoidal segments, are feasible just as well. On the side oriented towards the planar structure 31, the mushrooms 34 form a planar gripping surface 36 that is suitable for interlocking with or snap-in connection to other mushrooms 34 of engaging plates or with the recesses 33 of engaging plates.

Moreover, grooves 37 as connecting elements 37 are provided in the pins 32 adjacent to the gripping surfaces 36, whereby the mushrooms 34 of neighbouring plates can engage and/or snap into the grooves 37. For this purpose, the grooves 37 can be shaped differently from the grooves 37 shown, but in preferred manner according to the invention, as negative image of the shape of the curvature of the mushrooms 34 such that the mushrooms 34 fit well into the grooves 37.

FIG. 11 shows a schematic perspective view of two plates of the fourth bone replacement material according to the invention of the type according to FIG. 10 that are connected by means of the connecting elements 34, FIG. 12 shows a schematic perspective view of two plates of the fourth bone replacement material according to the invention of the type of FIGS. 10 and 11 that are not connected to each other, and FIG. 13 shows four schematic views of the fourth alternative bone replacement material in an embodiment having voids at the pins 32, in A) a perspective view of two plates that are connected by means of the connecting elements, B) a side view of a base plate, C) a top view of the top side of the base plate according to FIGS. 13 B), and D) a cross-sectional view along the section A-A according to FIG. 13 C).

In order to form a bone replacement material according to the invention, the plates preferably are situated to touch against each other, without being interlocked with or snapped into each other (i.e. unlike what is shown in FIG. 10 A) or 11 or 13 A)), such that the mushrooms 34 of the pins 32 of neighbouring plates do not engage each other yet. Moreover, the plates can be present in a condition wetted by a liquid. The liquid preferably contains at least one pharmaceutically active substance suitable for controlling an infection or for stimulating bone growth. Alternatively or in addition, the plates can be coated with a pharmaceutically active substance of this type.

The bone replacement material can be formed by pushing the plates into each other by means of their surfaces. By this means, the plates interlock with or snap into each other and the bone replacement material becomes reinforced as desired. Earlier, the plates can also be deformed and adapted to the treatment scenario through elastic deformation of the planar structure 31. After interlocking with or snapping into at least one further plate (which usually is also deformed), the two plates, thus connected to each other, stabilise each other to the effect that the selected shape is reinforced.

In this context, the plates become connected to each other in appropriate manner such that free gaps between the mutually connected plates remain in the regions of the pins 32, mushrooms 34, and grooves 37 such that the three-dimensional body formed from the plates is open-pored in the directions parallel to the plane of the plates. The plates have a cross-section and/or a thickness of approximately 6 mm such that the remaining pores have a free cross-section in the range of approximately 0.6 mm. Said cross-section is sufficient to allow bone material to be formed in and/or to grow into the pores. The three-dimensional body with its open pores can therefore be called osteoconductive. The three-dimensional body formed from the plates is therefore well-suited as bone replacement material.

The plates should be pushed firmly into each other such that the three-dimensional body is dimensionally stable. In this context, the plates can snap into each other in a first stage by the mushrooms 34 elastically deforming the pins 32 of connected plates and by the mushrooms 34 and/or by the edges of the mushrooms 34 being pushed into the grooves 37 by the elastic restoring force of the pins 32 and thus limiting the motion of neighbouring plates away from the planar structure 31 (see FIGS. 10, 11, and 13 A). When the plates are pushed further into each other, the plates can snap into each other in a second stage by the mushrooms 34 being pushed through the recesses 33 of the planar structure 31 (not shown). In this context, the mushrooms 34 can get lodged in the recesses 33 which prevents the mushrooms 34 from moving with respect to the neighbouring plate and thus snaps the two plates into each other. It is feasible just as well that, firstly, the edges of the mushrooms 34 plastically deform the pins 32, the grooves 37 or the recesses 33 or the mushrooms 34 to a small extent or, secondly, that the edges of the recesses 33 plastically deform the mushrooms 34 of neighbouring plates to a small extent and that the plates are thus snapped into each other.

Moreover, two plates can be connected to each other by snapping the plates into each other in some areas by means of the mushrooms 34 and the grooves 37 and by snapping them into each other in other areas by means of the mushrooms 34 and the recesses 33. Preferably, the dimensions of the mushrooms 34, the depth of the recesses 33 (and/or the thickness of the planar structure 31), the shape of the grooves 37, and the length of the pins 32 between the planar structure 31 and the mushrooms 34 are adapted to each other appropriately such that, upon connection of the plates, the surfaces of the mushrooms 34 facing away from the planar structure 31 touch against the surface of the planar structure 31 of neighbouring plates and/or, upon connection of the plates, the surfaces of the mushrooms 34 facing away from the planar structure 31 touch against the gripping surface 36 of the mushrooms 34 and preferably touch the grooves 37 of the pins 32 of the neighbouring plate along at least one line or particularly preferably in planar manner. As a result, the connected plates cannot move with respect to each other without deformation.

The grooves 37 also prevent the gripping surfaces 36 or the opposite cap top sides of the mushrooms 34 from completely covering the recesses 33. For the recesses 33 to be more easily deformable by the mushrooms 34, the recesses 33 can comprise multiple slits (not shown) that are distributed over the circumference of the recesses 33. The width of the slits should be sufficient to allow them to have an osteoconductive effect.

Accordingly, the fourth embodiment according to FIGS. 10 to 13 differs from the one according to FIGS. 1 to 7 mainly in that the pins 32 are thicker and comprise grooves 37 as additional connecting elements. Moreover, the recesses 33 comprise no additional slits.

FIG. 14 shows a schematic perspective view of two plates of a fifth bone replacement material according to the invention that are connected to each other by means of the connecting elements. FIG. 15 shows three schematic views of the two plates of the fifth alternative bone replacement material according to FIG. 14 that are connected to each other, i.e. FIG. 15 A) shows a top view of the top side, FIG. 15 B) shows a side view, and FIG. 15 C) shows a cross-sectional view along the section B-B according to FIG. 15 A).

The plates consist of a biocompatible metal, in particular of stainless steel, titanium or a titanium alloy, tantalum or a tantalum alloy or can be fabricated from an elastic biocompatible plastic material or a composite of said materials. The plates are produced through a CAM procedure and/or a 3D printing procedure, for example through selective electron beam melting (EBM). Other rapid prototyping methods and/or computer-aided generative production methods can also be used for producing the plates.

The plates each comprise a plate-shaped planar structure 41 that bears the entire plates and connects them in itself. The planar structure 41 is flexible and can be deformed elastically such that surfaces other than planes can be formed with the planar structure 41. A multitude of pins 42 extend away from the planar structure 41 of each plate, projecting perpendicularly away from the plane of the planar structure 41. A multitude of through-going recesses 43 are arranged between the pins 42 in the planar structure 41, which can cause the three-dimensional body to possess an open porosity in a direction perpendicular to the planar structures 41 when the plates are connected to each other to form a three-dimensional body and when the neighbouring plates do not touch and thus cover the recesses 43.

FIGS. 14 and 15 show two different types of plates, namely, firstly, base plates that comprise a flat bottom side and in which the pins 42 extend from the planar structure 41 only on one side of the planar structures 41, and, secondly, build-up plates, in which the pins 42 extend from both sides of the planar structure 41. The base plates are shown on the bottom in FIG. 14 and/or below it, on the bottom in FIG. 15 A) (in the image plane), on the bottom in FIG. 15 B), and on the right in FIG. 15 C). The build-up plates are shown in FIG. 14, on the top in FIG. 15 A) (out of the image plane), on the top in FIG. 15 B), and on the left in FIG. 15 C). The base plates can be attached to the bone to be treated such that large surface areas touch against it. However, the build-up plates can also be attached to the bone to be treated, although with a lesser contact surface, such that the base plates can be omitted.

The pins 42, otherwise being cylindrical, have mushrooms 44 or groups of four hooks 45 each provided as connecting elements 44, 45 on the ends of the pins 42 opposite from the planar structures 41. The mushrooms 44 are rounded towards the outside (away from the planar structure 41) and form spherical segments. However, other types of rounding, such as, for example, ellipsoidal segments, are feasible just as well. The hooks 45 are rounded towards the outside in like manner. On the side oriented towards the planar structure 41, the mushrooms 44 form a planar gripping surface 46 that is suitable for interlocking with or snap-in connection to other mushrooms 44 and hooks 45 of engaging plates or with the recesses 43 of engaging plates. Accordingly, on the side oriented towards the planar structure 41, the hooks 45 form undercuts that are suitable for interlocking with or snap-in connection to other mushrooms 44 and hooks 45 of engaging plates or with the recesses 43 of engaging plates.

Moreover, grooves 47 as connecting elements 47 are provided in the pins 42 adjacent to the gripping surfaces 46 and adjacent to the hooks 45, whereby the mushrooms 44 and hooks 45 of neighbouring plates can engage and/or snap into the grooves 47. For this purpose, the grooves 47 can be shaped differently from the grooves 47 shown, but in preferred manner according to the invention, as negative image of the shape of the curvature of the mushrooms 44 and/or hooks 45 such that the mushrooms 44 and hooks 45 fit well into the grooves 47.

In the present fifth embodiment, hooks 45 are provided exclusively on the base plate as connecting elements 45 and mushrooms 44 are provided exclusively on the build-up plate as connecting elements 44. This can be vice versa just as well and the hooks 45 and mushrooms 44 can also be present as mixed elements.

In order to form a bone replacement material according to the invention, the plates preferably are situated to touch against each other, without being interlocked with or snapped into each other (i.e. unlike what is shown in FIG. 14 or 15), such that the mushrooms 44 and hooks 45 of the pins 42 of neighbouring plates do not engage each other yet. Moreover, the plates can be present in a condition wetted by a liquid. The liquid preferably contains at least one pharmaceutically active substance suitable for controlling an infection or for stimulating bone growth. Alternatively or in addition, the plates can be coated with a pharmaceutically active substance of this type.

The bone replacement material can be formed by pushing the plates into each other by means of their surfaces. By this means, the plates interlock with or snap into each other and the bone replacement material becomes reinforced as desired. Earlier, the plates can also be deformed and adapted to the treatment scenario through elastic deformation of the planar structure 41. After interlocking with or snapping into at least one further plate (which usually is also deformed), the two plates, thus connected to each other, stabilise each other to the effect that the selected shape is reinforced.

In this context, the plates become connected to each other in appropriate manner such that free gaps between the mutually connected plates remain in the regions of the pins 42, mushrooms 44, hooks 45, and grooves 47 such that the three-dimensional body formed from the plates is open-pored in the directions parallel to the plane of the plates. The plates have a cross-section and/or a thickness of approximately 7 mm such that the remaining pores have a free cross-section in the range of approximately 0.7 mm. Said cross-section is sufficient to allow bone material to be formed in and/or to grow into the pores. The three-dimensional body with its open pores can therefore be called osteoconductive. The three-dimensional body formed from the plates is therefore well-suited as bone replacement material.

The plates should be pushed firmly into each other such that the three-dimensional body is dimensionally stable. In this context, the plates can snap into each other in a first stage by the mushrooms 44 and hooks 45 elastically deforming the pins 42 of connected plates and by the mushrooms 44 and hooks 45 and/or by the edges of the mushrooms 44 and tips of the hooks 45 being pushed into the grooves 47 by the elastic restoring force of the pins 42 and thus limiting the motion of neighbouring plates away from the planar structure 41 (see FIGS. 14 and 15). When the plates are pushed further into each other, the plates can snap into each other in a second stage by the mushrooms 44 and hooks 45 being pushed through the recesses 43 of the planar structure 41 (not shown). In this context, the mushrooms 44 and hooks 45 can get lodged in the recesses 43 which prevents the mushrooms 44 and hooks 45 from moving with respect to the neighbouring plate and thus snaps the two plates into each other. It is feasible just as well that, firstly, the edges of the mushrooms 44 and/or the tips of the hooks 45 plastically deform the pins 42, the grooves 47 or the recesses 43 or the mushrooms 44 to a small extent or, secondly, that the edges of the recesses 43 plastically deform the mushrooms 44 and/or hooks 45 of neighbouring plates to a small extent and that the plates are thus snapped into each other.

Moreover, two plates can be connected to each other by snapping the plates into each other in some areas by means of the mushrooms 44, hooks 45 and grooves 47 and by snapping them into each other in other areas by means of the mushrooms 44 and hooks 45 and the recesses 43. Preferably, the dimensions of the mushrooms 44, hooks 45, the depth of the recesses 43 (and/or the thickness of the planar structure 41), the shape of the grooves 47, and the length of the pins 42 between the planar structure 41 and the mushrooms 44 or hooks 45 are adapted to each other appropriately such that, upon connection of the plates, the surfaces of the mushrooms 44 and hooks 45 facing away from the planar structure 41 touch against the surface of the planar structure 41 of neighbouring plates and/or, upon connection of the plates, the surfaces of the mushrooms 44 and hooks 45 facing away from the planar structure 41 touch against the gripping surface 46 of the mushrooms 44 and preferably touch the grooves 47 of the pins 42 of the neighbouring plate along at least one line or particularly preferably in planar manner. As a result, the connected plates cannot move with respect to each other without deformation.

The grooves 47 also prevent the gripping surfaces 46 or the opposite cap top sides of the mushrooms 44 or the hooks 45 from completely covering the recesses 43. For the recesses 43 to be more easily deformable by the mushrooms 44 and hooks 45, the recesses 43 can comprise multiple slits (not shown) that are distributed over the circumference of the recesses 43. The width of the slits should be sufficient to allow them to have an osteoconductive effect.

Accordingly, the fifth embodiment according to FIGS. 14 and 15 differs from the one according to FIGS. 1 to 7 mainly in that the pins 42 are thicker and comprise grooves 47 and in that hooks 45 are provided as connecting elements 45. Moreover, the recesses 43 comprise no additional slits.

FIG. 16 shows a schematic perspective view of two plates of a sixth bone replacement material according to the invention that are interlocked with each other, and FIG. 17 shows a schematic perspective view of two plates of the sixth bone replacement material according to the invention according to FIG. 16 that are not interlocked with each other. FIG. 18 shows a schematic side view of plates of the sixth bone replacement material according to the invention according to FIG. 16 that are interlocked with each other. And finally, FIG. 19 shows a schematic perspective detailed view of two interlocked hooks (left), two non-interlocked hooks (right) of the sixth bone replacement material according to the invention according to FIGS. 16 to 18.

The plates consist of a biocompatible metal, in particular of stainless steel, titanium or a titanium alloy, tantalum or a tantalum alloy or can be fabricated from an elastic biocompatible plastic material. They can just as well be fabricated from a composite of said materials. The plates are produced through a CAM procedure and/or a 3D printing procedure. The rapid prototyping methods and/or computer-aided generative production methods mentioned with regard to other exemplary embodiments can be used to produce the plates.

The plates each comprise a plate-shaped planar structure 51 that bears the entire plates and connects them in itself. The planar structure 51 is flexible and can be deformed elastically such that surfaces other than planes can be formed with the planar structure 51. A multitude of pins 52 extend away from the planar structure 51 of each plate, projecting perpendicularly away from the plane of the planar structure 51. A multitude of through-going recesses 53 are arranged between the pins 52 in the planar structure 51, which cause the three-dimensional body to possess an open porosity in a direction perpendicular to the planar structures 51 when the plates are connected to each other to form a solid.

FIGS. 16 to 18 show two different types of plates, namely, firstly, base plates that comprise a flat bottom side and in which the pins 52 extend from the planar structure 51 only on one side of the planar structures 51, and, secondly, build-up plates, in which the pins 52 extend from both sides of the planar structure 51. The base plates are shown on the bottom in FIG. 16 and/or below it, in FIG. 2 and on the bottom in FIG. 18. The build-up plates are shown on the top in FIG. 16 and on the top in FIGS. 17 and 18. The base plates can be attached to the bone to be treated such that large surface areas touch against it. However, the build-up plates can also be attached to the bone to be treated, although with a lesser contact surface, such that the base plates can be omitted.

The pins 52, otherwise being cylindrical, have groups of four hooks 55 each provided as connecting elements 55 on the ends of the pins 52 opposite from the planar structures 51. The hooks 55 are rounded towards the outside (away from the planar structure 51) and form parts of spherical surfaces. However, other types of rounding, such as, for example, ellipsoidal segments, are feasible just as well. On the side oriented towards the planar structure 51, the hooks 55 form undercuts that are suitable for interlocking with or snap-in connection to other hooks 55 of engaging plates or with the recesses 53 of engaging plates. The pins 52 are thinner and/or shaped to have a smaller cross-section in the region adjacent to the hooks 55 and/or the undercuts of the hooks 55. The hooks 55 of neighbouring plates can engage and/or snap into the thinner regions more easily.

The present sixth embodiment is provided exclusively with hooks 55 as connecting elements 55. In order to form a bone replacement material according to the invention, the plates preferably are situated to touch against each other, without being interlocked with or snapped into each other (i.e. unlike what is shown in FIG. 16 or 18), such that the hooks 55 of the pins 52 of neighbouring plates do not engage each other yet. Moreover, the plates can be present in a condition wetted by a liquid. The liquid preferably contains at least one pharmaceutically active substance suitable for controlling an infection or for stimulating bone growth. Alternatively or in addition, the plates can be coated with a pharmaceutically active substance of this type.

The bone replacement material can be formed by pushing the plates into each other by means of their surfaces. By this means, the plates interlock with or snap into each other and the bone replacement material becomes reinforced as desired. Earlier, the plates can also be deformed and adapted to the treatment scenario through elastic deformation of the planar structure 51. After interlocking with or snapping into at least one further plate (which usually is also deformed), the two plates, thus connected to each other, stabilise each other to the effect that the selected shape is reinforced. The interlocking is shown in detail in FIG. 19.

In this context, the plates become connected to each other in appropriate manner such that free gaps between the mutually connected plates remain in the regions of the pins 52 and the hooks 55 such that the three-dimensional body formed from the plates is open-pored in the directions parallel to the plane of the plates. The plates have a cross-section and/or a thickness of approximately 5 mm such that the remaining pores have a free cross-section in the range of approximately 0.5 mm. Said cross-section is sufficient to allow bone material to be formed in and/or to grow into the pores. The three-dimensional body with its open pores can therefore be called osteoconductive. The three-dimensional body formed from the plates is therefore well-suited as bone replacement material.

The plates should be pushed firmly into each other such that the three-dimensional body is dimensionally stable. In this context, the plates can snap into each other in a first stage by the hooks 55 elastically deforming the pins 52 of connected plates and by the hooks 55 and/or by the tips of the hooks 55 being pushed into each other by the elastic restoring force of the pins 52 and thus limiting the motion of neighbouring plates away from the planar structure 51 (see FIGS. 16, 18, and 19). When the plates are pushed further into each other, the plates can snap into each other in a second stage by the hooks 55 being pushed through the recesses 53 of the planar structure 51 (not shown). In this context, the hooks 55 can get lodged in the recesses 53 which prevents the hooks 55 from moving with respect to the neighbouring plate and thus snaps the two plates into each other. It is feasible just as well that, firstly, the tips of the hooks 55 plastically deform the pins 52 or the recesses 53 to a small extent or, secondly, that the edges of the recesses 53 plastically deform the hooks 55 of neighbouring plates to a small extent and that the plates are thus snapped into each other.

Moreover, two plates can be connected to each other by snapping the plates into each other in some areas by means of the hooks 55 and by snapping them into each other in other areas by means of the hooks 55 and the recesses 53.

Preferably, the dimensions of the hooks 55, the depth of the recesses 53 (and/or the thickness of the planar structure 51), and the length of the pins 52 between the planar structure 51 and the hooks 55 are adapted to each other appropriately such that, upon connection of the plates, the sides of the hooks 55 facing away from the planar structure 51 touch against the surface of the planar structure 51 of neighbouring plates and, upon connection of the plates, the sides of the hooks 55 facing away from the planar structure 51 touch against the undercuts of the hooks 55. As a result, the connected plates cannot move with respect to each other without deformation.

The shape of the hooks 55 prevents them from covering the recesses 53 completely. For the recesses 53 to be more easily deformable by the hooks 55, the recesses 53 can comprise multiple slits (not shown) that are distributed over the circumference of the recesses 53.

Accordingly, the sixth embodiment according to FIGS. 16 to 19 differs from the one according to FIGS. 1 to 7 mainly in that regions of the pins 52 are thicker and mainly in that hooks 55 are provided as connecting elements 55. Moreover, the recesses 53 comprise no additional slits.

FIG. 20 shows a schematic perspective view of two plates of a seventh bone replacement material according to the invention that are not interlocked with each other, and FIG. 21 shows three schematic views of two plates of the seventh alternative bone replacement material that are connected to each other, A) as a top view of the top side, B) as a side view, and C) as a cross-sectional view along the section B-B according to FIG. 21 A).

The plates consist of a biocompatible metal, in particular of stainless steel, titanium or a titanium alloy, tantalum or a tantalum alloy or can be fabricated from an elastic biocompatible plastic material or a composite of said materials. The plates are produced through a CAM procedure and/or a 3D printing procedure, for example through selective electron beam melting (EBM). Other rapid prototyping methods and/or computer-aided generative production methods can also be used for producing the plates.

The plates each comprise a plate-shaped planar structure 61 that bears the entire plates and connects them in itself. The planar structure 61 is flexible and can be deformed elastically such that surfaces other than planes can be formed with the planar structure 61. A multitude of pins 62 extend away from the planar structure 61 of each plate, projecting perpendicularly away from the plane of the planar structure 61. A multitude of through-going recesses 63 are arranged between the pins 62 in the planar structure 61, which can cause the three-dimensional body to possess an open porosity in a direction perpendicular to the planar structures 61 when the plates are connected to each other to form a three-dimensional body and when the neighbouring plates do not touch and thus cover the recesses 63.

FIGS. 20 and 21 show two different types of plates, namely, firstly, base plates that comprise a flat bottom side and in which the pins 62 extend from the planar structure 61 only on one side of the planar structures 61, and, secondly, build-up plates, in which the pins 62 extend from both sides of the planar structure 61. The base plates are shown on the bottom in FIG. 20, on the bottom in FIG. 21 A) (in the image plane), on the bottom in FIG. 21 B), and on the right in FIG. 21 C). The build-up plates are shown on the top in FIG. 20, above the top in FIG. 21, i.e. in FIG. 21 A) (out of the image plane), on the top in FIG. 21 B), and on the left in FIG. 21 C). The base plates can be attached to the bone to be treated such that large surface areas touch against it. However, the build-up plates can also be attached to the bone to be treated, although with a lesser contact surface, such that the base plates can be omitted.

The pins 62, otherwise being cylindrical, have mushrooms 64 or groups of four hooks 65 each provided as connecting elements 64, 65 on the ends of the pins 62 opposite from the planar structures 61. The mushrooms 64 are rounded towards the outside (away from the planar structure 61) and form spherical segments. However, other types of rounding, such as, for example, ellipsoidal segments, are feasible just as well. The hooks 65 are rounded towards the outside in like manner. On the side oriented towards the planar structure 61, the mushrooms 64 form a planar gripping surface 66 that is suitable for interlocking with or snap-in connection to other mushrooms 64 and hooks 65 of engaging plates or with the recesses 63 of engaging plates. Accordingly, on the side oriented towards the planar structure 61, the hooks 65 form undercuts that are suitable for interlocking with or snap-in connection to other mushrooms 64 and hooks 65 of engaging plates or with the recesses 63 of engaging plates.

Moreover, grooves 67 as connecting elements 67 are provided in the pins 62 adjacent to the gripping surfaces 66 and adjacent to the hooks 65, whereby the mushrooms 64 and hooks 65 of neighbouring plates can engage and/or snap into the grooves 67. For this purpose, the grooves 67 can be shaped differently from the grooves 67 shown, but in preferred manner according to the invention, as negative image of the shape of the curvature of the mushrooms 64 and/or hooks 65 such that the mushrooms 64 and hooks 65 fit well into the grooves 67.

The present seventh embodiment has mushrooms 64 and hooks 65, mixed, provided on the plates as connecting elements 64, 65, whereby two of eleven connecting elements 64, 65 are hooks 65 and the remaining elements are mushrooms 64. This can be inverted just as well and the hooks 65 and mushrooms 64 can also be present at a different mixing ratio.

In order to form a bone replacement material according to the invention, the plates preferably are situated to touch against each other, without being interlocked with or snapped into each other (i.e. unlike what is shown in FIG. 21), such that the mushrooms 64 and hooks 65 of the pins 62 of neighbouring plates do not engage each other yet. Moreover, the plates can be present in a condition wetted by a liquid. The liquid preferably contains at least one pharmaceutically active substance suitable for controlling an infection or for stimulating bone growth. Alternatively or in addition, the plates can be coated with a pharmaceutically active substance of this type.

The bone replacement material can be formed by pushing the plates into each other by means of their surfaces. By this means, the plates interlock with or snap into each other and the bone replacement material becomes reinforced as desired. Earlier, the plates can also be deformed and adapted to the treatment scenario through elastic deformation of the planar structure 61. After interlocking with or snapping into at least one further plate (which usually is also deformed), the two plates, thus connected to each other, stabilise each other to the effect that the selected shape is reinforced.

In this context, the plates become connected to each other in appropriate manner such that free gaps between the mutually connected plates remain in the regions of the pins 62, mushrooms 64, hooks 65, and grooves 67 such that the three-dimensional body formed from the plates is open-pored in the directions parallel to the plane of the plates. The plates have a cross-section and/or a thickness of approximately 9 mm such that the remaining pores have a free cross-section in the range of approximately 0.9 mm. Said cross-section is sufficient to allow bone material to be formed in and/or to grow into the pores. The three-dimensional body with its open pores can therefore be called osteoconductive. The three-dimensional body formed from the plates is therefore well-suited as bone replacement material.

The plates should be pushed firmly into each other such that the three-dimensional body is dimensionally stable. In this context, the plates can snap into each other in a first stage by the mushrooms 64 and hooks 65 elastically deforming the pins 62 of connected plates and by the mushrooms 64 and hooks 65 and/or by the edges of the mushrooms 64 and tips of the hooks 65 being pushed into the grooves 67 by the elastic restoring force of the pins 62 and thus limiting the motion of neighbouring plates away from the planar structure 61 (see FIG. 21). When the plates are pushed further into each other, the plates can snap into each other in a second stage by the mushrooms 64 and hooks 65 being pushed through the recesses 63 of the planar structure 61 (not shown). In this context, the mushrooms 64 and hooks 65 can get lodged in the recesses 63 which prevents the mushrooms 64 and hooks 65 from moving with respect to the neighbouring plate and thus snaps the two plates into each other. It is feasible just as well that, firstly, the edges of the mushrooms 64 and/or the tips of the hooks 65 plastically deform the pins 62, the grooves 67 or the recesses 63 or the mushrooms 64 to a small extent or, secondly, that the edges of the recesses 63 plastically deform the mushrooms 64 and/or hooks 65 of neighbouring plates to a small extent and that the plates are thus snapped into each other.

Moreover, two plates can be connected to each other by snapping the plates into each other in some areas by means of the mushrooms 64, hooks 65, and grooves 67 and by snapping them into each other in other areas by means of the mushrooms 64 and/or hooks 65 and the recesses 63. Preferably, the dimensions of the mushrooms 64, hooks 65, the depth of the recesses 63 (and/or the thickness of the planar structure 61), the shape of the grooves 67, and the length of the pins 62 between the planar structure 61 and the mushrooms 64 or hooks 65 are adapted to each other appropriately such that, upon connection of the plates, the surfaces of the mushrooms 64 and hooks 65 facing away from the planar structure 61 touch against the surface of the planar structure 61 of neighbouring plates and/or, upon connection of the plates, the surfaces of the mushrooms 64 and hooks 65 facing away from the planar structure 61 touch against the gripping surface 66 of the mushrooms 64 and preferably touch the grooves 67 of the pins 62 of the neighbouring plate along at least one line or particularly preferably in planar manner. As a result, the connected plates cannot move with respect to each other without deformation.

The grooves 67 also prevent the gripping surfaces 66 or the opposite cap top sides of the mushrooms 64 or the hooks 65 from completely covering the recesses 63. For the recesses 63 to be more easily deformable by the mushrooms 64 and hooks 65, the recesses 63 can comprise multiple slits (not shown) that are distributed over the circumference of the recesses 63. The width of the slits should be sufficient to allow them to have an osteoconductive effect.

Accordingly, the fifth embodiment according to FIGS. 20 and 21 differs from the one according to FIGS. 1 to 7 mainly in that the pins 62 are thicker and comprise grooves 67 and in that hooks 65 are provided as connecting elements 65. Moreover, the recesses 63 comprise no additional slits.

FIG. 22 shows a schematic perspective view of two plates of an eighth bone replacement material according to the invention that are not interlocked with each other, and FIG. 23 shows three schematic views of two plates of the eighth alternative bone replacement material that are connected to each other—FIG. 23 A) shows a top view of the top side, FIG. 23 B) shows a side view, and FIG. 23 C) shows a cross-sectional view along the section C-C according to FIG. 23 A).

FIG. 24 shows a schematic perspective view of two plates of a modification of the eighth bone replacement material according to the invention that are not interlocked with each other, and FIG. 25 shows three schematic views of two plates of the modification of the eighth alternative bone replacement material that are connected to each other—FIG. 25 A) shows a top view of the top side, FIG. 25 B) shows a side view, and FIG. 25 C) shows a cross-sectional view along the section C-C according to FIG. 23 A).

The plates consist of titanium or a titanium alloy, tantalum or a tantalum alloy or can be fabricated from another elastic biocompatible material. The plates are produced through a CAM procedure and/or a 3D printing procedure, for example through selective electron beam melting (EBM). Other rapid prototyping methods and/or computer-aided generative production methods can also be used for producing the plates.

The plates each comprise a plate-shaped planar structure 71 that bears the entire plates and connects them in itself. The planar structure 71 is flexible and can be deformed elastically such that surfaces other than planes can be formed with the planar structure 71. A multitude of pins 72 extend away from the planar structure 71 of each plate, projecting perpendicularly away from the plane of the planar structure 71. A multitude of through-going recesses 73 are arranged between the pins 72 in the planar structure 71, which can cause the three-dimensional body to possess an open porosity in a direction perpendicular to the planar structures 71 when the plates are connected to each other to form a three-dimensional body and when the neighbouring plates do not touch and thus cover the recesses 73.

FIGS. 22 to 25 show two different types of plates, namely, firstly, base plates that comprise a flat bottom side and in which the pins 72 extend from the planar structure 71 only on one side of the planar structures 71, and, secondly, build-up plates, in which the pins 72 extend from both sides of the planar structure 71. The base plates are shown on the bottom in FIG. 22, on the bottom in FIG. 23 A) (in the image plane), on the bottom in FIG. 23 B), and on the right in FIG. 23 C) as well as on the bottom in FIG. 24, on the bottom in FIG. 25 A) (in the image plane), on the bottom in FIG. 25 B), and on the right in FIG. 25 C). The build-up plates are shown on the top in FIGS. 22 and 24 and above the top in FIG. 23, i.e. on the top in FIG. 23 A) (out of the image plane), on the top in FIG. 23 B), and on the left in FIG. 23 C) and/or on the top in FIG. 25 A) (out of the image plane), on the top in FIG. 25 B), and on the left in FIG. 25 C). The base plates can be attached to the bone to be treated such that large surface areas touch against it. However, the build-up plates can also be attached to the bone to be treated, although with a lesser contact surface, such that the base plates can be omitted.

The pins 72, otherwise being cylindrical, have mushrooms 74 or groups of four hooks 75 each provided as connecting elements 74, 75 on the ends of the pins 72 opposite from the planar structures 71. The mushrooms 74 are rounded towards the outside (away from the planar structure 71) and form spherical segments. However, other types of rounding, such as, for example, ellipsoidal segments, are feasible just as well. The hooks 75 are rounded towards the outside in like manner. On the side oriented towards the planar structure 71, the mushrooms 74 form undercuts 76 that are suitable for interlocking with or snap-in connection to hooks 75 of engaging plates. Accordingly, on the side oriented towards the planar structure 71, the hooks 75 form undercuts that are suitable for interlocking with or snap-in connection to other mushrooms 74 and hooks 75 of engaging plates or with the recesses 73 of engaging plates.

Moreover, grooves 77 as connecting elements 77 are provided in the pins 72 adjacent to the undercuts 76 and adjacent to the hooks 75, whereby the mushrooms 74 and hooks 75 of neighbouring plates can engage and/or snap into the grooves 77. For this purpose, the edges of the grooves 77 facing the planar structure 71 are shaped such as to be rounded such that the mushrooms 74 and hooks 75 fit and/or slide well in the grooves 77.

In the present eighth embodiment, mushrooms 74 and hooks 75 are provided on the plates as mixed connecting elements 74, 75. In the variant according to FIGS. 22 and 23, two of eleven connecting elements 74, 75 are hooks 75 and the remainder are mushrooms 74. In the variant according to FIGS. 24 and 25, eight of eleven connecting elements 74, 75 are hooks 75 and the remainder are mushrooms 74. This can be inverted just as well and the hooks 75 and mushrooms 74 can also be present at a different mixing ratio.

In order to form a bone replacement material according to the invention, the plates preferably are situated to touch against each other, without being interlocked with or snapped into each other (i.e. unlike what is shown in FIGS. 23 and 25), such that the mushrooms 74 and hooks 75 of the pins 72 of neighbouring plates do not engage each other yet. Moreover, the plates can be present in a condition wetted by a liquid. The liquid preferably contains at least one pharmaceutically active substance suitable for controlling an infection or for stimulating bone growth. Alternatively or in addition, the plates can be coated with a pharmaceutically active substance of this type.

The bone replacement material can be formed by pushing the plates into each other by means of their surfaces. By this means, the plates interlock with or snap into each other and the bone replacement material becomes reinforced as desired. Earlier, the plates can also be deformed and adapted to the treatment scenario through elastic deformation of the planar structure 71. After interlocking with or snapping into at least one further plate (which usually is also deformed), the two plates, thus connected to each other, stabilise each other to the effect that the selected shape is reinforced.

In this context, the plates become connected to each other in appropriate manner such that free gaps between the mutually connected plates remain in the regions of the pins 72, mushrooms 74, hooks 75, and grooves 77 such that the three-dimensional body formed from the plates is open-pored in the directions parallel to the plane of the plates. The plates have a cross-section and/or a thickness between 5 mm and 10 mm such that the remaining pores have a free cross-section in the range of approximately 0.5 mm and 1 mm. Said cross-section is sufficient to allow bone material to be formed in and/or to grow into the pores. The three-dimensional body with its open pores can therefore be called osteoconductive. The three-dimensional body formed from the plates is therefore well-suited as bone replacement material.

The plates should be pushed firmly into each other such that the three-dimensional body is dimensionally stable. In this context, the plates can snap into each other in a first stage by the mushrooms 74 and hooks 75 elastically deforming the pins 72 of connected plates and by the mushrooms 74 and hooks 75 and/or by the edges of the mushrooms 74 and tips of the hooks 75 being pushed into the grooves 77 by the elastic restoring force of the pins 72 and thus limiting the motion of neighbouring plates away from the planar structure 71 (see FIGS. 23 and 25). When the plates are pushed further into each other, the plates can snap into each other in a second stage by the mushrooms 74 and hooks 75 being pushed through the recesses 73 of the planar structure 71 (not shown). In this context, the mushrooms 74 and hooks 75 can get lodged in the recesses 73 which prevents the mushrooms 74 and hooks 75 from moving with respect to the neighbouring plate and thus snaps the two plates into each other. It is feasible just as well that, firstly, the edges of the mushrooms 74 and/or the tips of the hooks 75 plastically deform the pins 72, the grooves 77 or the recesses 73 or the mushrooms 74 to a small extent or, secondly, that the edges of the recesses 73 plastically deform the mushrooms 74 and/or hooks 75 of neighbouring plates to a small extent and that the plates are thus snapped into each other.

Moreover, two plates can be connected to each other by snapping the plates into each other in some areas by means of the mushrooms 74, hooks 75, and grooves 77 and by snapping them into each other in other areas by means of the mushrooms 74 and/or hooks 75 and the recesses 73. Preferably, the dimensions of the mushrooms 74, hooks 75, the depth of the recesses 73 (and/or the thickness of the planar structure 71), the shape of the grooves 77, and the length of the pins 72 between the planar structure 71 and the mushrooms 74 or hooks 75 are adapted to each other appropriately such that, upon connection of the plates, the surfaces of the mushrooms 74 and hooks 75 facing away from the planar structure 71 touch against the surface of the planar structure 71 of neighbouring plates and/or, upon connection of the plates, the surfaces of the mushrooms 74 and hooks 75 facing away from the planar structure 71 touch against the undercuts 76 of the mushrooms 74 and preferably touch the grooves 77 of the pins 72 of the neighbouring plate along at least one line. As a result, the connected plates cannot move with respect to each other without deformation.

The grooves 77 also prevent the gripping surfaces 76 or the opposite cap top sides of the mushrooms 74 or the hooks 75 from completely covering the recesses 73. For the recesses 73 to be more easily deformable by the mushrooms 74 and hooks 75, the recesses 73 can comprise multiple slits (not shown) that are distributed over the circumference of the recesses 73. The width of the slits should be sufficient to allow them to have an osteoconductive effect.

Accordingly, the eighth embodiment according to FIGS. 22 to 25 differs from the embodiment according to FIGS. 20 and 21 in that the mushrooms 74 comprise undercuts 76 that can be engaged by the hooks 75 of adjacent plates.

FIG. 26 shows a schematic perspective view of three and six pairwise mutually connected plates of the eighth alternative bone replacement material and of three particles of a bone replacement material, whereby the plates can be connected to the particles.

The particles are composed of a core that is arranged in the geometrical centre of the particles as well as twenty pins 82 that extend radially away from the core in various directions. Either mushrooms 84 or a group of four hooks 85 each are arranged as connecting elements 84, 85 on the otherwise cylindrical pins 82. The mushrooms 84 and hooks 85 correspond to the mushrooms 74 and hooks 75 of the plates and have similar dimensions. Accordingly, the mushrooms 84 and the hooks 85 are shaped to be spherically rounded towards the outside (away from the core). Other types of rounding, such as, for example, ellipsoidal segments, are feasible just as well. The mushrooms 84 have undercuts on the side oriented toward the core. Likewise, the hooks 85 comprise undercuts. The undercuts of the mushrooms 84 and the undercuts of the hooks 85 are suitable for interlocking with and/or snap-in connection to other mushrooms 84 and hooks 85 of engaging particles or for interlocking with and/or snap-in connection to the mushrooms 74 and hooks 75 of engaging plates.

Preferably, the pins 72 and connecting elements 74, 75 of the plates are matched to the pins 82 and connecting elements 84, 85 of the particles to allow uniform stability to be attained. The materials from which the particles can be made can be the same as the materials of the plates, and the same production procedures can be used.

The plates can be connected to the bone of a patient through fastening means (not shown) in the form of tips or screws. Subsequently, further plates of the bone replacement material according to the invention or the particles are fastened on the plate. In this context, the particles and the plates become appropriately connected to each other such that free gaps remain between the particles and plates that are connected to each other such that the reinforced three-dimensional body formed from the particles and plates is open-pored. The free cross-sections of the open-pored structure must still be sufficient such that bone material can form in and/or grow into the pores. The open-pored three-dimensional body formed from the plates and particles can therefore be called osteoconductive. To promote the osteoconductivity, the surface of the particles can just as well be coated with a bone growth-promoting substance. The three-dimensional body formed from the particles and plates is therefore well-suited as bone replacement material.

FIGS. 27 to 30 show plates of a ninth alternative bone replacement material according to the invention that is particularly preferred according to the invention. In this context, FIG. 27 shows a schematic perspective view of two plates snapped into each other, FIG. 28 shows a schematic perspective view of two plates according to FIG. 27 that are not snapped into each other, FIG. 29 shows two schematic views of the plates according to FIG. 27 that are snapped into each other, i.e. a top view of the top side (on the bottom in FIG. 29) and a side view (on the top in FIG. 29), and FIG. 30 shows a schematic cross-sectional view of the section A-A according to the bottom of FIG. 29 of the plates according to FIGS. 27 and 29 that are snapped into each other.

The plates consist of titanium or a titanium alloy, tantalum or a tantalum alloy or can be fabricated from another elastic biocompatible material. The plates are produced through a CAM procedure and/or a 3D printing procedure, for example through selective electron beam melting (EBM). Other rapid prototyping methods and/or computer-aided generative production methods can also be used for producing the plates.

The plates each comprise a plate-shaped planar structure 91 that bears the entire plates and connects them in itself. The planar structure 91 is flexible and can be deformed elastically such that surfaces other than planes can be formed with the planar structure 91. A multitude of pins 92 extend away from the planar structure 91 of each plate, projecting perpendicularly away from the plane of the planar structure 91. A multitude of through-going recesses 93 are arranged between the pins 92 in the planar structure 91, which can cause the three-dimensional body to possess an open porosity in a direction perpendicular to the planar structures 91 when the plates are connected to each other to form a three-dimensional body and when the neighbouring plates do not touch and thus cover the recesses 93.

FIGS. 27 to 30 show two different types of plates, namely, firstly, base plates that comprise a flat bottom side and in which the pins 92 extend from the planar structure 91 only on one side of the planar structures 91, and, secondly, build-up plates, in which the pins 92 extend from both sides of the planar structure 91. The base plates are shown on the bottom in FIG. 27 and/or below it, in FIG. 28 and on the bottom in the side view according to FIG. 29, below in the top view according to FIG. 29 (in the image plane), and on the bottom left in FIG. 30. The build-up plates are shown above the top in FIG. 27, in FIG. 28 and on the top in the side view according to FIG. 29, above in the top view according to FIG. 29 (out of the image plane), and on the top right in FIG. 30. The base plates can be attached to the bone to be treated such that large surface areas touch against it. However, the build-up plates can also be attached to the bone to be treated, although with a lesser contact surface, such that the base plates can be omitted.

The pins 92, otherwise being cylindrical, have mushrooms 94 as connecting elements 94 provided on the ends of the pins 92 opposite from the planar structures 91. The mushrooms 94 are rounded towards the outside (away from the planar structure 91) and form spherical segments. However, other types of rounding, such as, for example, ellipsoidal segments, are feasible just as well. On the side oriented towards the planar structure 91, the mushrooms 94 form a planar gripping surface 96 that is suitable for interlocking with or snap-in connection to other mushrooms 94 of engaging plates or with the recesses 93 of engaging plates.

Moreover, grooves 97 as connecting elements 97 are provided in the pins 96 and/or the gripping surfaces 96, whereby the mushrooms 94 of neighbouring plates can engage and/or snap into the grooves 97. For this purpose, the edges of the grooves 97 facing the planar structure 91 are shaped such as to be rounded such that the mushrooms 94 fit and/or slide well in the grooves 97. The shape of the grooves 97 corresponds to a negative image of the shape of the surface of the mushrooms 94 such that these can touch against a line in one of the grooves 97. The mushrooms 94 thus form snap-in means 94 and the grooves 97 form the matching opposite snap-in means 97. Further insertion of the plate is prevented by this structure.

The pins 92 with the mushrooms 94 are arranged in groups and/or islands of sixteen pins 92 and/or mushrooms 94 each. By this means, the pins 92 arranged on the edge of the groups and/or islands can be deformed outwards more easily when the mushrooms 94 of another plate are being pushed on. By this means, the plates can be connected to each other more easily since the elastic deformations of the pins 92 do not interfere with each other when the mushrooms 94 snap into the grooves 97.

In the present ninth embodiment, only mushrooms 94 and grooves 97 are provided on the plates as connecting elements 94, 97. Alternatively or in addition, hooks (not shown) can be provided on the pins 92 as connecting elements.

In order to form a bone replacement material according to the invention, the plates preferably are situated to touch against each other, without being interlocked with or snapped into each other (i.e. unlike what is shown in FIGS. 27, 29, and 30), such that the mushrooms 94 of the pins 92 of neighbouring plates do not engage each other yet. Moreover, the plates can be present in a condition wetted by a liquid. The liquid preferably contains at least one pharmaceutically active substance suitable for controlling an infection or for stimulating bone growth. Alternatively or in addition, the plates can be coated with a pharmaceutically active substance of this type.

The bone replacement material can be formed by pushing the plates into each other by means of their surfaces. By this means, the plates interlock with or snap into each other and the bone replacement material becomes reinforced as desired. Earlier, the plates can also be deformed and adapted to the treatment scenario through elastic deformation of the planar structure 91. After interlocking with or snapping into at least one further plate (which usually is also deformed), the two plates, thus connected to each other, stabilise each other to the effect that the selected shape is reinforced.

In this context, the plates become connected to each other in appropriate manner such that free gaps between the mutually connected plates remain in the regions of the pins 92, mushrooms 94, and grooves 97 such that the three-dimensional body formed from the plates is open-pored in the directions parallel to the plane of the plates. The plates have a cross-section and/or a thickness between 5 mm and 10 mm such that the remaining pores have a free cross-section in the range of approximately 0.5 mm and 1 mm. Said cross-section is sufficient to allow bone material to be formed in and/or to grow into the pores. The three-dimensional body with its open pores can therefore be called osteoconductive. The three-dimensional body formed from the plates is therefore well-suited as bone replacement material.

The plates should be pushed firmly into each other such that the three-dimensional body is dimensionally stable. In this context, the plates can interlock with each other by the mushrooms 94 elastically deforming the pins 92 of connected plates and by the mushrooms 94 and/or by the edges of the mushrooms 94 being pushed into the grooves 97 by the elastic restoring force of the pins 92 and thus limiting the motion of neighbouring plates away from the planar structure 91 (see FIGS. 27, 29, and 30). Since the shape of the grooves 97 is made to match that of the mushrooms 94 further motion of the mushrooms 94 is blocked, specifically when a large number of mushrooms 94 is snapped into a large number of grooves 97.

Preferably, the dimensions of the mushrooms 94, the thickness of the planar structure 91, the shape of the grooves 97, and the length of the pins 92 between the planar structure 91 and the mushrooms 94 are adapted to each other appropriately such that, upon connection of the plates, the surfaces of the mushrooms 94 and hooks 95 facing away from the planar structure 91 touch against the surface of the grooves 97 of neighbouring plates and, upon connection of the plates, the gripping surfaces 96 of the mushrooms 94 touch against the gripping surfaces 96 of the mushrooms 94 of the neighbouring plate. As a result, the connected plates cannot move with respect to each other without the action of a large force.

The grooves 97 also prevent the gripping surfaces 96 or the opposite cap top sides of the mushrooms 94 from completely covering the recesses 93. For the recesses 93 to be covered even less well by the mushrooms 94, the recesses 93 can comprise multiple slits (not shown) that are distributed over the circumference of the recesses 93.

Accordingly, the ninth embodiment according to FIGS. 27 to 30 differs from the embodiment according to FIGS. 1 to 7 mainly in that the mushrooms 94 comprise matching grooves 97 as additional connecting elements into which the mushrooms 94 of adjacent plates can snap, and in that the pins 92 are thicker. Moreover, the recesses 93 comprise no additional slits.

FIG. 31 shows a schematic perspective view of multiple plates of a tenth and eleventh bone replacement material according to the invention which are partly interlocked by its connecting elements 104, 114.

FIGS. 31, 33 and 36 show plates of a tenth bone replacement material according to the invention, which is especially preferred according to the present invention. In that FIG. 33 showing three schematic views of a plate of the tenth alternative bone replacement material, namely on bottom of FIG. 33 a top view of the top side, in the middle of FIG. 33 a side view and on top of FIG. 33 a cross-sectional view along the section B-B according to FIG. 33 bottom. FIG. 36 showing two schematic views of two plates of the tenth alternative bone replacement material that are connected to each other, namely on bottom of FIG. 36 a top view of the top side and on top of FIG. 36 a cross-sectional view along the section E-E according to FIG. 36 bottom.

FIGS. 31, 34 and 37 show plates of an eleventh bone replacement material according to the invention, which is especially preferred according to the present invention. In that FIG. 34 showing three schematic views of a plate of the eleventh alternative bone replacement material, namely on bottom of FIG. 34 a top view of the top side, in the middle of FIG. 34 a side view and on top of FIG. 34 a cross-sectional view along the section C-C according to FIG. 34 bottom. FIG. 37 showing two schematic views of two plates of the eleventh alternative bone replacement material that are connected to each other, namely on bottom of FIG. 37 a top view of the top side and on top of FIG. 37 a cross-sectional view along the section F-F according to FIG. 37 bottom.

FIGS. 32 and 35 show plates of a twelfth bone replacement material according to the invention, which is also especially preferred according to the present invention. In that FIG. 32 showing three schematic views of a plate of the twelfth alternative bone replacement material, namely on bottom of FIG. 32 a top view of the top side, in the middle of FIG. 32 a side view and on top of FIG. 32 a cross-sectional view along the section A-A according to FIG. 32 bottom. FIG. 35 showing two schematic views of two plates of the twelfth alternative bone replacement material that are connected to each other, namely on bottom of FIG. 35 top view of the top side and on top of FIG. 35 a cross-sectional view along the section D-D according to FIG. 35 bottom.

The three embodiments ten, eleven and twelve are very much alike and therefore can be described together in the following.

The plates consist of titanium or a titanium alloy, tantalum or a tantalum alloy or can be fabricated from another elastic biocompatible material. The plates are produced through a CAM procedure or a 3D printing procedure respectively, for example through selective electron beam melting (EBM). Other rapid prototyping methods and/or computer-aided generative production methods can also be used for producing the plates.

The plates each comprise a plate-shaped planar structure 101, 111, 121 bearing the entire plates and connecting them in themselves. The planar structure 101, 111, 121 is flexible and can be deformed elastically such that surfaces other than planes can be formed with the planar structure 101, 111, 121. A multitude of pins 102, 112, 122 extend away from the planar structure 101, 111, 121 of each plate, projecting perpendicularly away from the plane of the planar structure 101, 111, 121. A multitude of through-going recesses 103, 113, 123 are arranged between the pins 102, 112, 122 in the planar structure 101, 111, 121, which can cause the three-dimensional body to possess an open porosity in a direction perpendicular to the planar structures 101, 111, 121 when the plates are connected to each other to form a three-dimensional body and when the neighbouring plates do not touch and thus cover the recesses 103, 113, 123.

In FIGS. 31 to 37 two types of plates are shown for the tenth, eleventh and twelfth embodiment, namely firstly base plates, which provide a flat bottom side and in which the pins 102, 112, 122 extend away from the planar structure 101, 111, 121 only on one side of the planar structure 101, 111, 121 and secondly build-up plates, in which the pins 102, 112, 122 extend away from both sides of the planar structure 101, 111, 121. The base plates being shown in FIG. 31 bottom left and in all other Figures as the lower of both shown plates. Said base plates can be attached to the bone to be treated such that large surface areas touch against it. However, the build-up plates shown can also be attached to the bone to be treated, although with a lesser contact surface, such that the base plates can be omitted.

The pins 102, 112, 122, otherwise being cylindrical, each have four mushrooms 104, 114, 124 as connecting elements 104, 114, 124 provided on above one another. The mushrooms 104, 114, 124 are rounded towards the outside (away from the planar structure 101, 111, 121). The mushrooms 104, 124 of the tenth embodiment (FIGS. 31, 33 and 35) and the twelves embodiment (FIGS. 32 and 35) form spherical segments on the tips of the pins 102, 122, while the mushrooms 114 of the eleventh embodiment being slightly spikier on the tips of the pins 112. However, other types of rounding, such as, for example, ellipsoidal segments, are feasible just as well. The mushrooms 104, 114, 124 located beneath the mushrooms 104, 114, 124 on the tip of the pins 102, 112, 122, which are therefore located in between the planar structure 101, 111, 121 and the mushrooms 104, 114, 124 which are located on the pins 102, 112, 122 on the side away from the planar structure 101, 111, 121, having the shape of a truncated cone. On the side oriented towards the planar structure 101, 111, 121, the mushrooms 104, 114, 124 form a planar gripping surface 106, 116, 126 that is suitable for interlocking with or snap-in connection to other mushrooms 104, 114, 124 of engaging plates or with the recesses 103, 113, 123 of engaging plates. The pins 112 and mushrooms 114 of the eleventh embodiment (FIGS. 31, 34 and 37) have a slightly smaller diameter than that of the tenth and twelfth embodiment, whereby the gripping surfaces 116 of the eleventh embodiment are configured somewhat deeper or with a larger area than the gripping surfaces 106, 126 of the tenth and twelfth embodiments.

Moreover, grooves 107, 117, 127 as connecting elements 107, 117, 127 are provided in the pins 102, 112, 122 adjacent to the gripping surfaces 106, 116, 126, whereby the mushrooms 104, 114, 124 of neighbouring plates can engage and/or snap into the grooves 107, 117, 127. For this purpose, the grooves 107, 117, 127 are formed approximately as negative image of the shape of the curvature of the mushrooms 104, 114, 124 such that the mushrooms 104, 114, 124 match along a line to the grooves 107, 117, 127. The mushrooms 104, 114, 124 thus form snap-in means 104, 114, 124 and the grooves 107, 117, 127 form the matching opposite snap-in means 107, 117, 127. Further insertion of the plate is possible in the tenth, eleventh and twelfth embodiment, by pushing the pins 102, 112, 122 together with the mushrooms 104, 114, 124 into or respectively through the recesses 103, 113, 123.

For the twelfth embodiment the pins 122 with the mushrooms 124 are arranged in groups and/or islands of forty-six pins 122 each. By this means, the pins 122 arranged on the edge of the groups and/or islands can be deformed outwards more easily when the mushrooms 124 of another plate are being pushed on. By this means, the plates can be connected to each other more easily since the elastic deformations of the pins 122 do not interfere with each other when the mushrooms 124 snap into the grooves 127.

In order to form a bone replacement material according to the invention, the plates preferably are situated to touch against each other, without being interlocked with or snapped into each other, such that the mushrooms 104, 114, 124 of the pins 102, 112, 122 of neighbouring plates do not engage each other yet. Moreover, the plates can be present in a condition wetted by a liquid. The liquid preferably contains at least one pharmaceutically active substance suitable for controlling an infection or for stimulating bone growth. Alternatively or in addition, the plates can be coated with a pharmaceutically active substance of this type.

The bone replacement material can be formed by pushing the plates into each other by means of their surfaces. By this means, the plates interlock with or snap into each other and the bone replacement material becomes reinforced as desired. Earlier, the plates can also be deformed and adapted to the treatment scenario through elastic deformation of the planar structure 101, 111, 121. After interlocking with or snapping into at least one further plate (which usually is also deformed), the two plates, thus connected to each other, stabilise each other to the effect that the selected shape is reinforced.

In this context, the plates become connected to each other in appropriate manner such that free gaps between the mutually connected plates remain in the regions of the pins 102, 112, 122 the mushrooms 104, 114, 124 and the grooves 107, 117, 127 such that the three-dimensional body formed from the plates is open-pored in the directions parallel to the plane of the plates. The plates have a cross-section and/or a thickness of approximately 5 mm and 10 mm such that the remaining pores have a free cross-section in the range between 0.5 mm and 1 mm. Said cross-section is sufficient to allow bone material to be formed in and/or to grow into the pores. The three-dimensional body with its open pores can therefore be called osteoconductive. The three-dimensional body formed from the plates is therefore well-suited as bone replacement material.

The pins 102, 112, 122 are thinnest in between the mushrooms 104, 114, 124 and the planar structure 101, 111, 121, so the pins 102, 112, 122 may be tilted most easily, or respectively are most flexible, in the connection to the planar structure 101, 111, 121, thereby allowing the mushrooms 104, 114, 124 to interlock with or snap into the grooves 107, 117, 127 in between the mushrooms 104, 114, 124.

The plates should be pushed firmly into each other such that the three-dimensional body is dimensionally stable. In this context, the plates can interlock with each other in a first stage by the mushrooms 104, 114, 124 elastically deforming the pins 102, 112, 122 and because of the elastic restoring force of the pins 102, 112, 122 the mushrooms 104, 114, 124 or the edge of the mushrooms 104, 114, 124 respectively are pushed inside the grooves 107, 117, 127 thereby limiting the motion of neighbouring plates away from the planar structure 101, 111, 121 (see FIGS. 35 to 37). When the plates are pushed further into each other (not shown), the plates can snap into each other in a second stage by the mushrooms 104, 114, 124 being pushed through the recesses 103, 113, 123 of the planar structures 101, 111, 121. In this context, the mushrooms 104, 114, 124 can get lodged in the recesses 103, 113, 123 which prevents the mushrooms 104, 114, 124 from moving with respect to the neighbouring plate and thus snaps the two plates into each other. It is feasible just as well that, firstly, the edges of the mushrooms 104, 114, 124 plastically deform the pins 102, 112, 122, the grooves 107, 117, 127, the recesses 103, 113, 123 or the mushrooms 104, 114, 124 to a small extent or, secondly, that the edges of the recesses 103, 113, 123 plastically deform the mushrooms 104, 114, 124 of neighbouring plates to a small extent and that the plates are thus snapped into each other.

Moreover, two plates can be connected to each other through a first interlocking of the plates in some areas by means of the mushrooms 104, 114, 124 located at the tips of the pins 102, 112, 122. Moreover, two plates can be connected to each other through interlocking the plates in some areas by means of the mushrooms 104, 114, 124 and by snapping them into each other in other areas by means of the mushrooms 104, 114, 124 and recesses 103, 113, 123. Preferably, the dimensions of the mushrooms 104, 114, 124, the depth of the recesses 103, 113, 123 (the thickness of the planar structure 101, 111, 121 respectively), and the length of the pins 102, 112, 122 between the planar structure 101, 111, 121 and the mushrooms 104, 114, 124 are adapted to each other appropriately such that, upon connection of the plates, the surfaces of the mushrooms 104, 114, 124 facing away from the planar structure 101, 111, 121 touch against the surface of the planar structure 101, 111, 121 of neighbouring plates and, upon connection of the plates, the surfaces of the mushrooms 104, 114, 124 facing away from the planar structure 101, 111, 121 touch against the gripping surface 106, 116, 126 of the mushrooms 104, 114, 124 of the neighbouring plate. As a result, the connected plates cannot move with respect to each other without deformation.

Accordingly, the tenth, eleventh and twelfth embodiments according to FIGS. 31 to 37 differ from the one according to FIGS. 1 to 7 mainly in that by the multiple mushrooms 104, 114, 124 located above on another the mushrooms 104, 114, 124 can interlock with one another in different positions, thereby allowing a bone replacement material can be built most accurate and with only small deviations in thickness. Furthermore more and more mushrooms 104, 114, 124 grab into grooves 107, 117, 127 of neighbouring plates while reducing the distance of the plates, thereby providing a more and more stable network.

The features of the invention disclosed in the preceding description and in the claims, figures, and exemplary embodiments, can be essential for the implementation of the various embodiments of the invention both alone and in any combination.

LIST OF REFERENCE NUMBERS 1, 11, 21, 31, 41, 51, 61, 71, 91, 101, 111, 121 Planar structure
2, 12, 22, 32, 42, 52, 62, 72, 92, 102, 112, 122 Pin
3, 13, 23, 33, 43, 53, 63, 73, 93, 103, 113, 123 Recess
4, 14, 24, 34, 44, 64, 74, 94, 104, 114, 124 Mushroom/connecting element
6, 16, 26, 36, 46, 66, 96, 106, 116, 126 Gripping surface
37, 47, 67, 77, 97, 107, 117, 127 Groove/connecting element
38 Screw/fastening means
39 Tip/fastening means
45, 55, 65, 75 Hook/connecting element
76 Undercut
82 Pin
84 Mushroom/connecting element
85 Hook/connecting element

The invention claimed is:

1. Planar alloplastic bone replacement material comprising at least one plate for augmentation of bone defects, wherein the bone replacement material consists of a biocompatible plastic material, a biocompatible metal and/or a biocompatible metal alloy, wherein the at least one plate comprises a planar structure and comprises a plurality of pins extending outwards from the planar structure of the at least one plate, wherein the pins each comprise at least one connecting element, wherein the pins are deformable elastically and are arranged sufficiently close to each other such that pressing the surfaces of multiple plates onto each other causes the connecting elements of different plates to interlock with and/or snap into each other and the interlocked and/or snapped-in plates form an open-pored body of mutually interlocked and/or snapped-in plates.

2. The bone replacement material according to claim 1, wherein the connecting elements are mushrooms, hooks, undercuts, snap-in elements and/or opposite snap-in means.

3. The Bone replacement material according to claim 1, wherein the distance between the connecting elements and the planar structure of the at least one plate is between 0.3 mm and 2 mm or between 0.5 mm and 1 mm.

4. The bone replacement material according to claim 1, wherein the pins of the at least one plate extend perpendicular or at an angle between 60° and 90° out of the planar structure of the at least one plate.

5. The bone replacement material according to claim 1, wherein the connecting elements are provided on the jacket surface of the pins.

6. The bone replacement material according to claim 1, wherein plates that are pressed into each other interlock with and/or snap into each other irreversibly.

7. The bone replacement material according to claim 1, wherein the thickness of the at least one plate without projecting pins is between 0.25 mm and 1.5 mm.

8. The bone replacement material according to claim 1, wherein the at least one plate is produced with a generative 3D printing procedure.

9. The bone replacement material according to claim 1, wherein at least one of the at least one connecting elements per pin has a truncated cone shape, wherein the longitudinal axes of the pins form the longitudinal axes of the cones and wherein the jacket of the cones faces toward the outer side that faces away from the planar structure of the at least one plate.

10. The bone replacement material according to claim 1, wherein at least one of the at least one connecting elements per pin is provided in the form of a hook and/or as a mushroom head.

11. The bone replacement material according to claim 1, wherein the pins contain a circumferential groove as additional connecting element between the planar structure of one plate and at least one of the at least one connecting elements, wherein connecting elements of other plates can interlock with or snap into said groove such that no further motion of the connecting elements along the pins is possible.

12. The bone replacement material according to claim 1, wherein at least two connecting elements are arranged in succession on the jacket surface of the pins.

13. The bone replacement material according to claim 1, wherein the at least one plate is provided in the shape of a square, rectangle, trapezoid, parallelepiped and/or polygon.

14. The bone replacement material according to claim 1, wherein the planar structure of the at least one plate contains through-going pores, wherein the pores comprise no sharp-edged contours, wherein the pores in the planar structure of the plate have a free cross-section between 0.25 mm and 1 mm or between 0.3 mm and 0.9 mm.

15. The bone replacement material according to claim 1, wherein the planar structure of the at least one plate contains through-going pores, wherein the depth of the pores perpendicular to the planar structure of the at least one plate is at least 0.25 mm, or at least 0.4 mm.

16. The bone replacement material according to claim 1, wherein the at least one plate is made from biocompatible plastic material, stainless steel, titanium, a titanium alloy, tantalum, a tantalum alloy or composites of said materials.

17. The bone replacement material according to claim 1, wherein neighbouring pins, that are arranged on the same side of a first plate of the at least one plate, are situated at an appropriate distance from each other such that the pins of the first plate, after elastic deformation due to interlocking and/or snapping into a connecting element of a second plate of the at least one plate, enable at least two interlocks and/or snap-in connections to at least two further connecting elements of the second plate.

18. The bone replacement material according to claim 1, wherein the plate or at least one of the plates comprises pins just on one side and is attachable in planar manner to a bone on the other side, wherein, sharp tips are provided for this purpose that can be pushed into the bone or eyelets or boreholes are provided in the planar structure of the at least one plate by means of which the at least one plate can be screwed to a bone or attached by other means.

19. The bone replacement material according to claim 1, wherein the at least one plate or at least one of the at least one plates comprises pins on both sides.

20. The bone replacement material according to claim 1, wherein the at least one plate is mixed with inorganic or organic particulate bone replacement material and/or autologous or allogenic cancellous bone.

21. The bone replacement material according to claim 1, wherein the at least one plate is coated with one or more pharmaceutical agents from the groups of antibiotics, bisphosphonates, steroids, non-steroidal anti-inflammatory drugs, growth factors, and cytostatic agents.

22. The bone replacement material according to claim 1, wherein the at least one plate or at least one of them is provided as a semi-spherical cup or domed surface or as an arc or as a trough.

23. The bone replacement material according to claim 1, wherein the pores of the open-pored body formed from multiple plates to be interconnecting and osteoconductive, wherein the pores have a free cross-section between 0.1 mm and 1 mm or between 0.25 mm and 0.9 mm.

24. The bone replacement material according to claim 1, wherein the at least one plate can be deformed plastically or elastically in the planar structure.

25. The bone replacement material according to claim 1, wherein the pins having connecting elements are arranged in rows of three or more pins each and in that a strip of unoccupied surface of the at least one plate remains between these three or more rows each or in that a grouped or nested arrangement of pins having connecting elements is provided.

26. The bone replacement material according to claim 1, wherein the bone replacement material comprises at least one particle aside from the at least one plate, wherein the at least one particle comprises a core and at least six pins extending from the core, wherein the pins each comprise at least one connecting element that is designed in analogous manner to the connecting elements of the at least one plates such that the at least one plate and the at least one particle interlock with and/or snap into each other by pressing the connecting elements of the at least one plate and of the at least one particle onto each other, and whereby the mutually interlocked and/or snapped-in plate(s) and particle(s) form an open-pored body of mutually interlocked and/or snapped-in plate(s) and particle(s).

27. A method for forming a body made of a planar alloplastic bone replacement material comprising the at least one plate according to claim 1, in which multiple plates are pushed against each other, wherein the plates interlock with and/or snap into each other and form an open-pored body.

28. The method according to claim 27, wherein at least one of the plates is being connected to a porous three-dimensional body of a second bone replacement material by snapping-in and/or interlocking the connecting elements with the pores of the second bone replacement material, and/or at least one of the plates are being connected to a particulate third bone replacement material comprising multiple particles, whereby the particles of the third bone replacement material comprise a plurality of pins that extend from a core of the particles and have connecting elements, wherein the pins and the connecting elements of the particles of the third bone replacement material comprise the features of the pins and connecting elements of the at least one plate of the bone replacement material according to claim 1.

29. Implant material, in trauma surgery, orthopaedics or veterinary medicine, comprising the bone replacement material according to claim 1.

* * * * *